United States Patent [19]

Abrecht et al.

[11] Patent Number: 5,644,024

[45] Date of Patent: Jul. 1, 1997

[54] TETRAHYDRONAPHTHALENE DERIVATIVES

[75] Inventors: Christine Abrecht, Lengnau; Klaus Müller, Münchenstein; Daniel Obrecht, Basle, all of Switzerland; Arnold Trzeciak, Schopfheim, Germany

[73] Assignee: Hoffmann-La Roche Inc., Nutley, N.J.

[21] Appl. No.: 292,128

[22] Filed: Aug. 17, 1994

[30] Foreign Application Priority Data

Aug. 27, 1993 [CH] Switzerland .................... 2552/93

[51] Int. Cl.$^6$ .................... C07K 7/54; C07K 4/00; C07D 285/00
[52] U.S. Cl. .................... 530/317; 540/455; 530/321; 544/335; 546/326; 549/79; 549/484; 562/433
[58] Field of Search .................... 530/317, 321; 540/455

[56] References Cited

PUBLICATIONS

Chen, et al., Biochemistry, 11, No. 22: pp. 4120–4131, (1972).
Chen and Kane, Biochemistry, 13, No. 16, pp. 3330–3335 (1974).
Callahan, et al, Tetrahedron, vol. 49, No. 17 pp. 3479–3488 (1993).
Callahan, et al, J. Med. Chem. vol. 35, pp. 3970–3972 (1992).

*Primary Examiner*—Robert T. Bond
*Attorney, Agent, or Firm*—George W. Johnston; Dennis P. Tramaloni; Bruce A. Pokras

[57] ABSTRACT

The present invention is concerned with tetrahydronaphthalene derivatives which are mimics of domains of peptides or proteins which can interact with other proteins or with DNA or RNA through α-helical conformation, said tetrahydronaphthalene derivatives having the formulae:

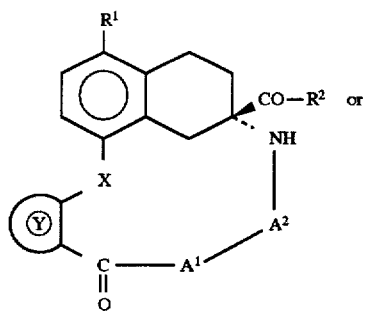

Ia

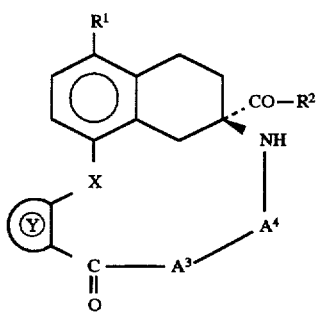

Ib are valuable aids in the determination of biologically active peptide sequences and are accordingly so-called "research tools". They are, however, also potentially suitable as medicaments.

24 Claims, 3 Drawing Sheets

5,644,024

TETRAHYDRONAPHTHALENE DERIVATIVES

SUMMARY OF THE INVENTION

The present invention is concerned with tetrahydronaphthalene derivatives which are mimetics of domains of peptides or proteins which can interact with other proteins or with DNA or RNA through α-helical conformation, said tetrahydronaphthalene derivatives having the formulae:

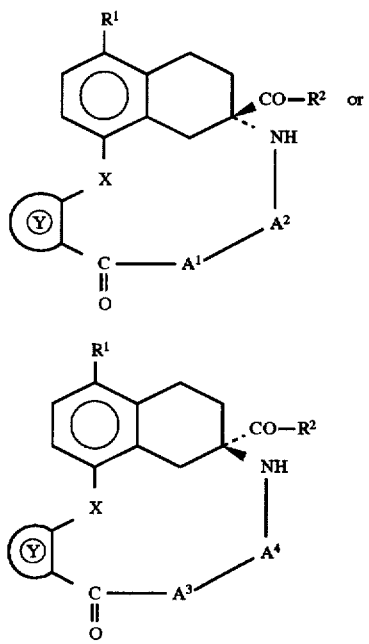

wherein $R^1$ is hydrogen, bromine, cyano, formyl, hydroxy, lower alkyl, lower alkenyl, lower alkynyl, lower alkoxy, aryloxy, lower aralkoxy or aryl;

$R^2$ is an amino acid residue or a chain of 2 to 20 amino acid residues derived from a biologically active peptide or protein;

$A^1$, $A^2$, $A^3$ and $A^4$ each are residues of α-amino acids, wherein $A^1$ or $A^2$ are in the L configuration and $A^3$ or $A^4$ are in the D configuration when the α-C atom of said α-amino acid residue is asymmetric;

X is oxygen or sulphur; and

Y is an aromatic ring selected from the group consisting of benzene, furan, thiophene, pyridine or pyrimidine, wherein said aromatic ring is substituted or unsubstituted;

as well as salts thereof.

Objects of the present invention are the compounds of general formulae Ia and Ib and salts thereof, their manufacture, intermediates for their manufacture, and the use of compounds of formulae Ia and Ib and of salts thereof as research tools.

The invention also comprises compounds of the formulae:

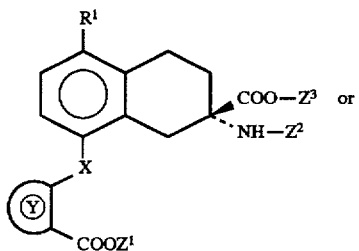

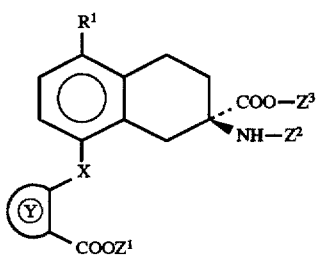

wherein $R^1$, X and Y have the above significance and $Z^1$ and $Z^3$ are carboxyl protecting groups and $Z^2$ is an amino protecting group.

DETAILED DESCRIPTION OF THE INVENTION

Figure 1:
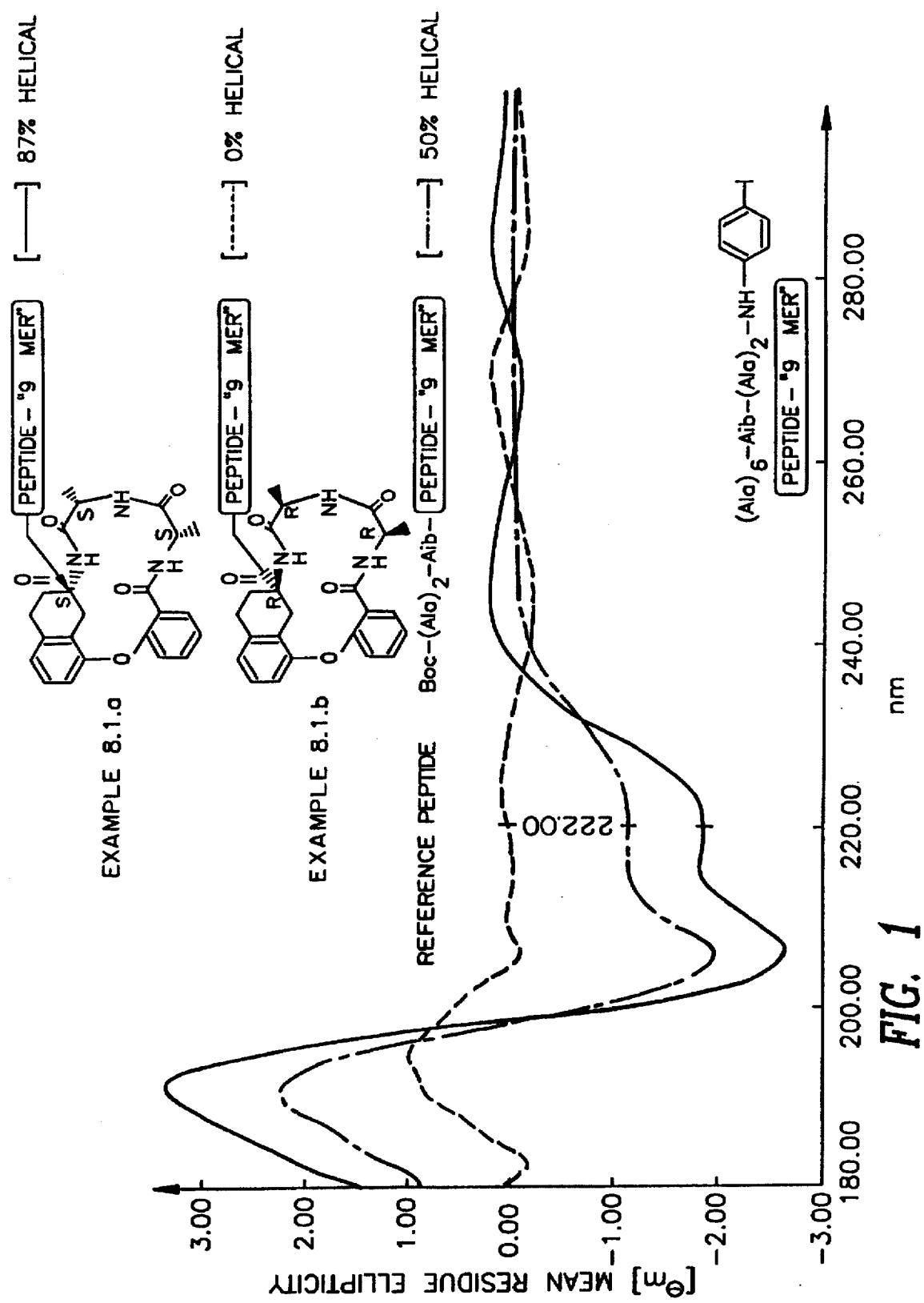
FIG. 1: shows a comparison of the helicity of a 9-residue polypeptide when that polypeptide contains an N-Cap of each of the configurations of formula Ia and Ib, and also without an N-Cap but with a Boc-(Ala)$_2$-Aib residue instead.

The present invention is concerned with tetrahydronaphthalene derivatives having the formulae:

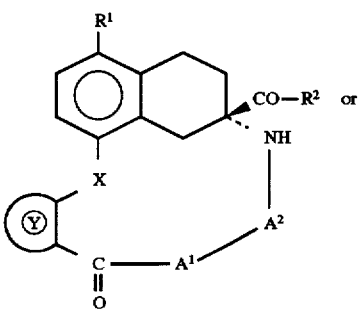

-continued

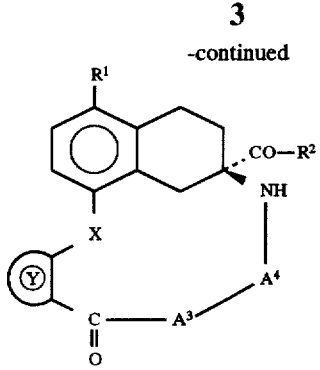

wherein

- $R^1$ is hydrogen, bromine, cyano, formyl, hydroxy, lower alkyl, lower alkenyl, lower alkynyl, lower alkoxy, aryloxy, lower aralkoxy or aryl;
- $R^2$ is an amino acid residue or a chain of 2 to 20 amino acid residues derived from a biologically active peptide or protein;
- $A^1$, $A^2$, $A^3$ and $A^4$ each are residues of α-amino acids, wherein $A^1$ or $A^2$ are in the L configuration and $A^3$ or $A^4$ are in the D configuration when the α-C atom of said α-amino acid residue is asymmetric;
- X is oxygen or sulphur; and
- Y is an aromatic ring selected from the group consisting of benzene, furan, thiophene, pyridine or pyrimidine, wherein said aromatic ring is substituted or unsubstituted;

as well as salts thereof.

The compounds of general formulae Ia and Ib and their salts are novel. The compounds of formulae Ia and Ib as a whole, including the amino acid residue or chain $R^2$, are referred to as "N-Capped peptides." Thus, the compounds, which the exception of the group $R^2$, are referred to as "N-Caps." The appropriate N-Cap which is selected from one of the configurations Ia or Ib increases the α-helicity of a peptide chain $R^2$ in comparison to the corresponding non-N-Capped peptide. The other configuration reduces the degree of α-helicity that may be present in the corresponding non-N-Capped peptide.

Thus, the N-Capped peptides of the invention and their salts, especially those which do not contain protecting group(s), are useful as mimetics of domains of peptides or proteins which can interact with other proteins or with DNA or RNA through α-helical conformation. Thus, the N-Capped polypeptides of the invention have the therapeutic utility of the biologically active peptide or protein from which the peptide chain $R^2$ is derived due to their being mimetics of that domain thereof which can interact with other proteins or with DNA or RNA through α-helical conformation.

The N-Capped peptides of the invention are also valuable aids for determining whether the α-helical region of a biologically active protein, from which the peptide chain ($R^2$) in formulae Ia and Ib is derived, is the source of the biological activity of said protein, and are therefore so-called "research tools".

"Derived" is meant to encompass $R^2$ peptide chains which are analogs of the domains of peptides or proteins which can interact with other proteins or with DNA or RNA through α-helical conformation in addition to the native amino acid sequence of said peptide or protein.

Objects of the present invention are the compounds of general formulae Ia and Ib and salts thereof, their manufacture, intermediates for their manufacture, and the use of compounds of general formulae Ia and Ib and of salts thereof as research tools.

The invention further comprises compounds of formulas Ia and Ib, and their salts, wherein X is oxygen and all other substituents are as above.

The invention further comprises compounds of formulas Ia and Ib, and their salts, wherein X is sulfur and all other substituents are as above.

The invention further comprises compounds of formulas Ia and Ib, and their salts, wherein X is oxygen and Y is benzene or pyridine which are unsubstituted or mono- or di-substituted by nitro, amino, lower alkanoylamino, hydroxy, lower alkoxy, lower alkanoyloxy, lower alkyl, fluorine, cyano, carboxy or formyl, or is condensed with a benzene ring to form a bicyclic system.

The invention further comprises compounds of formulas Ia and Ib, and their salts, wherein X is oxygen and Y is benzene, benzene substituted by alkanoylamino, or pyridine The invention further comprises compounds of formulas Ia and Ib, and there salts, wherein X is oxygen, $R^1$ is hydrogen, Y is benzene or pyridine which are unsubstituted or mono- or di-substituted by nitro, amino, lower alkanoylamino, hydroxy, lower alkoxy, lower alkanoyloxy, lower alkyl, fluorine, cyano, carboxy or formyl, or is condensed with a benzene ring to form a bicyclic system, and all other substituents are as above.

The invention further comprises compounds of formulas Ia and Ib, and their salts, wherein X is oxygen, $R^1$ is hydrogen, and Y is benzene, benzene substituted by alkanoylamino, or pyridine The invention also comprises compounds of the formulae:

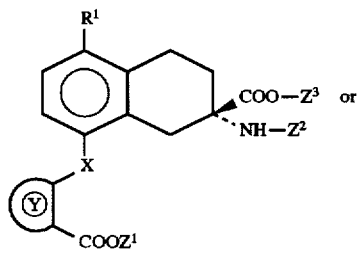

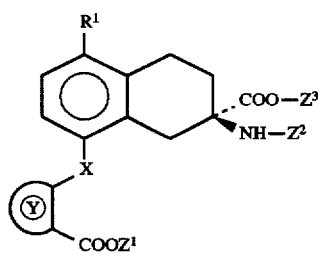

wherein $R^1$, X and Y are as defined in the corresponding embodiments of formulas Ia and Ib, above, $Z^1$ and $Z^3$ are carboxyl protecting groups and $Z^2$ is an amino protecting group.

The compounds of formulas IVa and IVb are useful for preparing the compounds of formulae Ia and Ib. The protecting groups $Z^1$, $Z^2$, and $Z^3$ are not critical. Any conventional carboxyl protecting groups may be used for $Z^1$ and $Z^3$, and any conventional amino protecting group may be used for $Z^2$. Preferably, $Z^1$ is benzyl, tert.-butyl, allyl or pentafluorophenyl, $Z^2$ is benzyloxycarbonyl, tert.-butyloxycarbonyl or 9-fluorenylmethoxycarbonyl and $Z^3$ is methyl, tert.-butyl, benzyl, trimethylsilylethyl or pentafluorophenyl.

Preferred compounds of formulas IVa and IVb are those in which $R^1$ is hydrogen, X is oxygen, and Y is benzene, benzene substituted by nitro, or pyridine.

The invention also comprises compounds of the formulae:

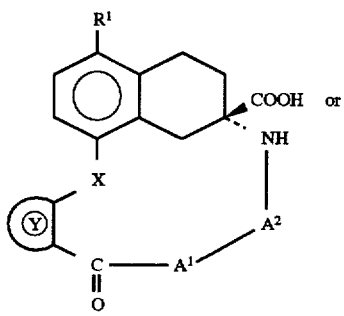

IIa

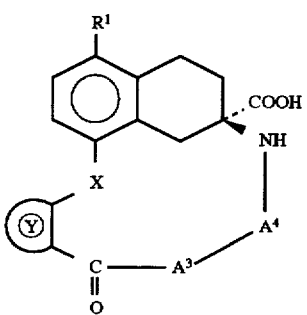

IIb wherein $R^1$, X, Y, $A^1$, $A^2$, $A^3$, and $A^4$ are as defined above for the various embodiments of the compounds of formulae Ia and Ib.

The invention also comprises compounds of the formulae:

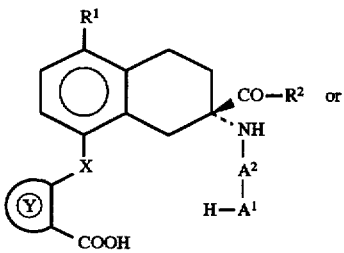

IIIa

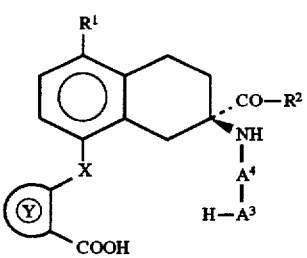

IIIb wherein $R^1$, $R^2$, $A^1$, $A^2$, $A^3$, $A^4$, X and Y are as defined above for the various embodiments of the compounds of formulae Ia and Ib.

The term "lower alkyl" embraces straight-chain or branched saturated hydrocarbon residues with up to 7, preferably up to 4, carbon atoms such as methyl, ethyl, n-propyl, isopropyl, n-butyl, isobutyl, tert.butyl and the like. In an analogous manner, the terms "lower alkenyl" and "lower alkynyl" embrace hydrocarbon residues with up to 7, preferably up to 4, carbon atoms which contain a double bond or, respectively, a triple bond, such as vinyl, ethynyl, allyl, propargyl and the like. The term "lower alkoxy" embraces alkyloxy groups in the sense of the above definition of the term "lower alkyl". The term "aryl" embraces phenyl residues optionally mono- or disubstituted by lower alkyl or lower alkoxy or optionally substituted by lower alkylenedioxy. The term "halogen" denotes the four forms fluorine, chlorine, bromine and iodine unless expressly indicated to the contrary.

As amino acid residues there primarily come into consideration those which are derived from α-amino acids, especially from natural α-amino acids; the amino acid residues can, insofar as their α-C atom is asymmetric, be present not only in the L form, but also in the D form, and they can be protected by conventional protecting groups. Hereinafter there is given a list of amino acids which, or the residues of which, are suitable for the purpose of the present invention, with the abbreviations corresponding to the relevant IUPAC rules (Biochemistry 11, 1726 (1972)) and to generally usual practice.

| | |
|---|---|
| $Ac_3c$ | 1-Aminocyclopropanecarboxylic acid |
| $Ac_4c$ | 1-Aminocyclobutanecarboxylic acid |
| $Ac_5c$ | 1-Aminocyclopentanecarboxylic acid |
| $Ac_6c$ | 1-Aminocyclohexanecarboxylic acid |
| $Ac_7c$ | 1-Aminocycloheptanecarboxylic acid |
| Aib | 2-Amino-2-methylpropionic acid |
| Ala | L-Alanine |
| D-Ala | D-Alanine |
| β-Ala | β-Alanine |
| Arg | L-Arginine |
| D-Arg | D-Arginine |
| Asn | L-Asparagine |
| D-Asn | D-Asparagine |
| Asp | L-Aspartic acid |
| D-Asp | D-Aspartic acid |
| D-Asp (ONa) | Sodium D-aspartate |
| $C_3al$ | L-3-Cyclopropylalanine |
| $C_4al$ | L-3-Cyclobutylalanine |
| $C_5al$ | L-3-Cyclopentylalanine |
| $C_6al$ | L-3-Cyclohexylalanine |
| Cys | L-Cysteine |
| D-Cys | D-Cysteine |
| Glu | L-Glutamic acid |
| D-Glu | D-Glutamic acid |
| Gln | L-Glutamine |
| D-Gln | D-Glutamine |
| Gly | Glycine |
| His | L-Histidine |
| D-His | D-Histidine |
| Hyp | 4-Hydroxy-L-proline |
| Ile | L-Isoleucine |
| alle | L-Alloisoleucine |
| D-Ile | D-Isoleucine |
| D-alle | D-Alloisoleucine |
| D-Itg | D-2-(Isothiazolyl)glycine |
| Leu | L-Leucine |
| D-Leu | D-Leucine |
| tert.-Leu | L-2-Amino-3,3-dimethylbutyric acid |
| D-tert.-Leu | D-2-Amino-3,3-dimethylbutyric acid |
| Lys | L-Lysine |
| D-Lys | D-Lysine |
| Lys (CHO) | $N^6$-Formyl-L-lysine |
| MeAla | N-Methyl-L-alanine |
| MeLeu | N-Methyl-L-leucine |
| MeMet | N-Methyl-L-methionine |
| Met | L-Methionine |
| D-Met | D-Methionine |
| Met(O) | L-Methionine sulphoxide |
| D-Met(O) | D-Methionine sulphoxide |
| $Met(O_2)$ | L-Methionine sulphone |
| $D-Met(O_2)$ | D-Methionine sulphone |
| Nal | L-3-(1-Naphthylalanine) |
| D-Nal | D-3-(1-Naphthylalanine) |
| Nle | L-Norleucine |
| D-Nle | D-Norleucine |
| Nva | L-Norvaline |
| D-Nva | D-Norvaline |
| Orn | L-Ornithine |
| D-Orn | D-Ornithine |
| Orn(CHO) | $N^5$-Formyl-L-ornithine |
| Phe | L-Phenylalanine |

-continued

| | |
|---|---|
| D-Phe | D-Phenylalanine |
| L-Phg | L-Phenylglycine |
| D-Phg | D-Phenylglycine |
| Pip | L-Pipecolinic acid |
| D-Pip | D-Pipecolinic acid |
| Pro | L-Proline |
| D-Pro | D-Proline |
| Sar | Sarcosine |
| Ser | L-Serine |
| D-Ser | D-Serine |
| Thr | L-Threonine |
| D-Thr | D-Threonine |
| Thz | L-Thiazolidine-4-carboxylic acid |
| D-Thz | D-Thiazolidine-4-carboxylic acid |
| Trp | L-Tryptophane |
| D-Trp | D-Tryptophane |
| D-Trp(CHO) | $N^{in}$-Formyl-D-tryptophane |
| D-Trp(O) | D-3-(2,3-Dihydro-2-oxoindol-3-yl)alanine |
| Tyr | L-Tyrosine |
| D-Tyr | D-Tyrosine |
| Tza | L-3-(2-Thiazolyl)alanine |
| D-Tza | D-3-(2-Thiazolyl)alanine |
| Tzg | L-2-(Thiazolyl)glycine |
| D-Tzg | D-2-(Thiazolyl)glycine |
| Val | L-Valine |
| D-Val | D-Valine |

The amino acid protecting groups used in accordance with the invention are not critical. Any conventional amino acid protecting groups may be used in accordance with the invention. Suitable protecting groups for amino acids and, respectively, their residues are, for example:

for the amino group (as is present, e.g., also in the side-chain of lysine):

| | |
|---|---|
| Z | Benzyloxycarbonyl |
| Boc | tert.-Butyloxycarbonyl |
| Fmoc | 9-Fluorenylmethoxycarbonyl |
| Alloc | Allyloxycarbonyl |
| Teoc | Trimethylsilylethoxycarbonyl |
| Tcc | Trichloroethoxycarbonyl |
| Nps | o-Nitrophenylsulphenyl; | for the carboxyl group (as is present, e.g., also in the side-chain of aspartic acid and glutamic acid) by conversion into corresponding esters with the alcohol components:

| | |
|---|---|
| tBu | tert.- Butyl |
| Bzl | Benzyl |
| Me | Methyl |
| Ph | Phenyl |
| Pac | Phenacyl |
| | Allyl |
| | Trimethylsilylethyl |
| | Trichloroethyl; | for the guanidine group (as is present, for example, in the side-chain of arginine):

| | |
|---|---|
| Pmc | 2,2,5,7,8-Pentamethylchroman-6-sulphonyl |
| Ts | Tosyl |
| Z | Benzyloxycarbonyl; | for the hydroxy group (as is present, for example, in the side-chain of threonine and serine):

| | |
|---|---|
| tBu | tert.-Butyl |
| Bzl | Benzyl |
| | Trityl; | and for the mercapto group (as is present, for example, in the side-chain of cysteine):

| | |
|---|---|
| tBu | tert.-Butyl |
| Bzl | Benzyl |
| | Trityl |
| | 2-Methoxytrityl. |

The substituent $R^1$ in is not critical to the utility of the compounds of the invention as research tools. Thus, a wide variety of substituents may be used as $R^1$, as described above. $R^1$ is preferably hydrogen. When $R^1$ is aryl, then this is preferably a phenyl residue mono- or di-substituted by lower alkyl or lower alkoxy or a phenyl residue substituted by lower alkylenedioxy.

The group $R^2$ may be an amino acid residue or any sequence of from 2 to 20 amino acid residues which is derived from a domain of a peptide or protein which can interact with other proteins or with DNA or RNA through α-helical conformation. $R^2$ preferably contains 9 to 15 α-helical amino acid residues, especially 9, 12 or 15 amino acid residues. α-amino acid residues in which the α-C atom is asymmetric are preferably in the L configuration. Such amino acids containing an asymmetric α-C atom are, for example, derived from L-alanine, L-glutamine, L-glutamic acid, L-isoleucine, L-leucine, L-lysine or 2-amino-2-methylpropionic acid.

The amino acid residue(s) of $R^2$ may be protected by any conventional amino acid protecting groups, or may be unprotected. The C-terminal amino acid residue of $R^2$ can be present as the free or protected acid or in the form of an amide. When the C-terminal amino acid residue of $R^2$ is present in the form of an amide, then the amide group can be unsubstituted or substituted at the nitrogen atom by any conventional substituent, for example by 4-iodophenyl.

The α-amino acid residues $A^1$, $A^2$, $A^3$ and $A^4$ are not critical. Preferably, $A^1$ or $A^3$ is a residue of L- or D-alanine, asparagine, aspartic acid, glutamine, glutamic acid or lysine or of 2-amino-2-methylpropionic acid, and $A^2$ or $A^4$ is a residue of L- or D-alanine, asparagine, aspartic acid, glutamine, glutamic acid or lysine. It is especially preferred that $A^1$ or $A^3$ is L- or D-alanyl or lysyl and $A^2$ or $A^4$ is D-alanyl.

The aromatic ring denoted by Y may be unsubstituted or substituted. When substituted, the aromatic ring is preferably mono- or di-substituted by nitro, amino, lower alkanoylamino, hydroxy, lower alkoxy, lower alkanoyloxy, lower alkyl, fluorine, cyano, carboxy or formyl, or is condensed with a benzene ring to form a bicyclic system.

Representative compounds of formulae Ia and Ib within the scope of the present invention are:

[(12S,15S,18S)-12,15-Dimethyl-10,13,16-trioxo-10,11, 12, 13,14,15,16,17,18,19,20,21-dodecahydro-1,18-etheno-dibenz[b,n][1,5,8,11]oxatriaza-cyclopentadecen-18-ylcarbonyl]-L-alanyl-L-alanyl-L-alanyl-L-alanyl-L-alanyl-L-alanyl-(2-amino-2-methylpropionyl)-L-alanyl-L-alanine (4-iodophenyl) amide;

[(12R, 15R,18R)-12,15-dimethyl-10,13,16-trioxo-10,11, 12, 13,14,15,16,17,18,19,20,21-dodecahydro-1,18-etheno-dibenz-[b,n][1,5,8,11]oxatriazacyclopentadecen-18-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl)amide;

[(12S,15S,18S)-12,15-dimethyl-10,13,16-trioxo-10,11, 12,13, 14,15,16,17,18,19,20,21-dodecahydro-1,18-etheno-dibenz-[b,n][1,5,8,11]oxatriaza-cyclopentadecen-18-yl-carbonyl]-L-leucyl-L-lysyl-L-alanyl-L-glutamyl-L-isoleucyl-L-alanyl-L-glutaminyl-L-lysyl-L-leucinamide trifluoroacetate;

[(12R,15R,18R)-12,15-dimethyl-10,13,16-trioxo-10,11, 12, 13,14,15,-16,17,18,19,20,21-dodecahydro-1,1 8-etheno-dibenz-[b,n][1,5,8,11]oxatriaza-cyclopentadecen-18-yl-carbonyl]-L-leucyl-L-lysyl-L-alanyl-L-glutamyl-L-isoleucyl-L-alanyl-L-glutaminyl-L-lysyl-L-leucinamide trifluoroacetate;

[(14aS, 17S,20S)-8-acetylamino-17-methyl-10,15,18-trioxo-11,12,13,14,14a,15,16,17,18,19,20,21,22,23-tetradecahydro-1,20-etheno-10H-pyrrolo[1,2-e]dibenz[b,n][1,5,8,11]oxatriazacyclopentadecen-20-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl)amide;

[(12S, 15S, 18S)-12-(2-methoxycarbonyl-ethyl)-15-methyl-10,13,16-trioxo-10,11,12,13,14,15,16,17,18, 19,20,21-dodecahydro-1,18-etheno-pyrido[2,3-b]benz[n][1,5,8,11]oxatriazacyclopentadecen-18-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl)amide;

[(12S,16S,19S)-16-methyl-10,13,17,23-tetraoxo-10,11, 12, 13,14,15,16,17,18,-19,20,21,22,23-tetradecahydro-1,19-etheno-12,15-metheno-pyrido[2,3-b]benz[o][1,5, 9,12]oxatriazacyclohexadecen-19-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl)amide;

[(12S,15S,18S)-12-(2-carboxy-ethyl)-15-methyl-10,13, 16-trioxo-10,11,12,13,14,15,16,17,18,19,20,21-dodecahydro-1,18-etheno-pyrido[2,3-b]benz[n][1,5,8, 11]oxatriazacyclopentadecen-18-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl)amide; and

[(12S,15S,18S)-12-(2-carboxymethyl)-15-methyl-10,13, 16-trioxo-10,11,1 2,13,14,15,16,17,18,19,20,21-dodecahydro-1,18-etheno-pyrido[2,3-b]benzo[n][1,5, 8]-oxatriazacyclopentadecen-18-ylcarbonyl]-L-alanyl-L-alanyl-L-alanyl-L-alanyl-L-alanyl-L-alanyl-(2-amino-2-methyl-propionyl)-L-alanyl-L-alanyl-(4-iodophenyl)amide.

The compounds of formulae Ia and Ib as well as their salts can be manufactured in accordance with the invention by:

a) coupling a compound of the general formula

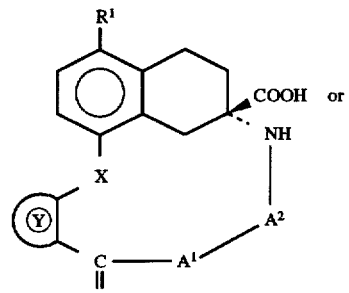

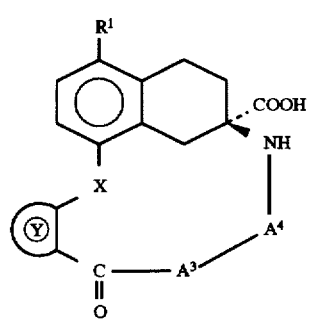

wherein $R^1$, $A^1$, $A^2$, $A^3$, $A^4$, X and Y have the above significance, with an optionally protected amino acid or chain of up to 20 amino acids, the C-terminal amino acid of which can be present as the free or protected acid or in the form of an amide; or b) cyclizing a compound of the formula:

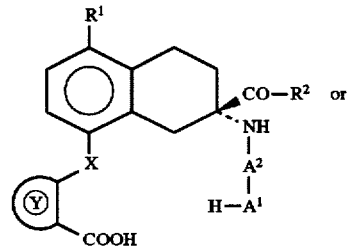

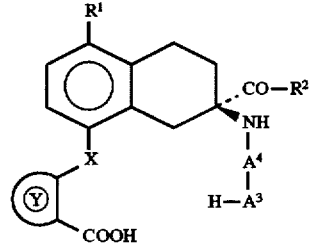

wherein $R^1$, $R^2$, $A^1$, $A^2$, $A^3$, $A^4$, X and Y have the above significance; or c) cleaving off the protecting group(s) from a compound of formula Ia or Ib which contains at least one protecting group; or d) converting a compound of formula Ia or Ib which contains a basic centre or an acidic centre into a salt using an acid or, respectively, a base.

The compounds of formulae IIa, IIb, IIIa and IIIb are novel and are likewise objects of the invention.

In accordance with process variant a), the free carboxyl group of a compound of formula IIa or IIb is coupled with an amino acid or peptide component having a N-terminal free amino group, and in the case of the cyclization of a compound of formula IIIa or IIIb a free carboxyl group and a free amino group are coupled with one another with the formation of an amide bond.

Methods which are generally used in peptide chemistry and which will be familiar to any person skilled in the art are used for carrying out these process variants. Solid phase synthesis methods can of course also be used; aminomethyl-polystyrene resin and the like is, for example, suitable as the carrier.

All possible activating reagents which are conventional in peptide chemistry can be used to carry out the coupling according to process variants a) and b), such as, e.g., O-benzotriazol-1-yl-N,N,N',N'-tetramethyl-uronium hexafluorophosphate (HBTU), O-(1,2-dihydro-2-oxo-1-pyridyl)-N,N,N',N'-tetramethyluronium tetrafluoroborate (TPTU), 2-(1H-benzotriazol-1-yl)-1,1,3,3-tetramethyluronium tetrafluoroborate (TBTU), 1-hydroxybenzotriazole (HOBT) in combination with N,N-dicyclohexylcarbodiimide and the like.

By cleaving off the protecting group(s) from a compound of formula Ia or Ib which contains at least one protecting group, there is obtained in accordance with process variant c) a corresponding compound of formula Ia or Ib which does not contain protecting group(s). The cleavage of the protecting group(s) is effected according to methods which are conventional in peptide chemistry and which will be familiar to any person skilled in the art, of course while taking into consideration the nature of the protecting group(s) to be removed. Thus, the protecting groups referred to above can be cleaved off, for example, as follows:

Z: Catalytic hydrogenation in the presence of Pd/C in a lower alkanol such as methanol or ethanol.

Boc: Using trifluoroacetic acid/methylene chloride (1:1) or using saturated hydrogen chloride solution in ethyl acetate.

Fmoc: Using piperidine or 1,8-diazabicyclo[5.4.0]undec-7-ene in dimethylformamide.

Alloc: Using palladium-tetrakis-triphenylphosphine in tetrahydrofuran/dimethyl sulphoxide/0.1N hydrochloric acid.

Teoc: Using caesium fluoride or tetrabutylammonium fluoride in dimethylformamide or the like.

Tcc: Using zinc in glacial acetic acid or methanol.

Nps: Using sodium rhodanide or potassium rhodanide in a slightly acidic medium.

$^t$Bu: Using trifluoroacetic acid/methylene chloride (1:1).

Bzl: By catalytic hydrogenation in the presence of Pd/C in a lower alkanol such as methanol or ethanol.

Me: Using lithium hydroxide in tetrahydrofuran/methanol/water (3:1:1).

Ph: Using sodium peroxide at pH 10.5.

Pac: Using zinc in glacial acetic acid or methanol or using sodium thiophenolate in dimethylformamide.

Allyl: Using palladium-bis-triphenylphosphine dichloride and tributyltin hydride or using palladium-tetrakis-triphenylphosphine in tetrahydrofuran/dimethyl sulphoxide/0.5N hydrochloric acid.

Trimethylsilyl ether: Using caesium fluoride or tetrabutylammonium fluoride in dimethylformamide or the like.

Trichloroethyl: Using zinc in glacial acetic acid or methanol.

PmC: Using aqueous trifluoroacetic acid.

Ts: Using sodium in liquid ammonia or liquid hydrogen fluoride.

In an analogous manner, a compound of formula Ia or Ib manufactured by solid phase synthesis on an aminomethyl-polystyrene resin or the like can be cleaved off from the carrier resin, for example using "Field's reagent", i.e., a mixture of 82.5% trifluoroacetic acid, 5% phenol, 5% water, 5% thioanisole and 2.5% 1,2-ethanedithiol.

In accordance with process variant d), a compound of formula Ia or Ib which contains a basic centre or an acidic centre can be converted into a salt using an acid or, respectively, a base, which can be effected according to conventional methods which will be familiar to any person skilled in the art. Acids which can be used are inorganic acids such as hydrochloric acid, sulphuric acid, phosphoric acid or the like, or organic acids such as trifluoroacetic acid, methanesulphonic acid, p-toluenesulphonic acid or the like. Bases which can be used are inorganic bases such as potassium hydroxide, sodium hydroxide or the like, or organic bases such as triethylamine, dimethylaminopyridine or the like.

The starting materials of formulae IIa and IIb and IIIa and IIIb which are required for process variants a) and, respectively, b) can be prepared from compounds of the formulae IVa and IVb.

The preparation of the compounds of formulae IVa and IVb and their conversion into compounds of formulae IIa or IIb and IIIa or IIIb are illustrated in more detail hereinafter, in part on the basis of Reaction Schemes.

Reaction Scheme 1

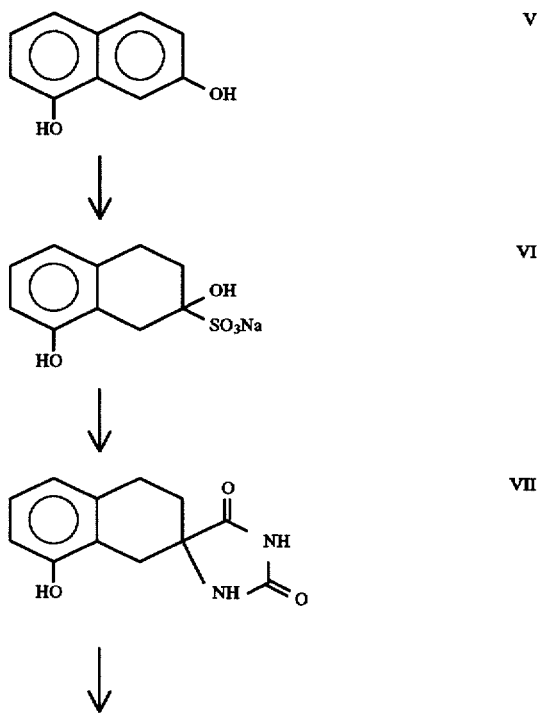

-continued
Reaction Scheme 1
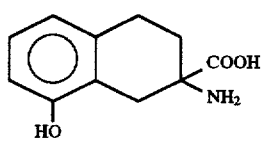
 VIII
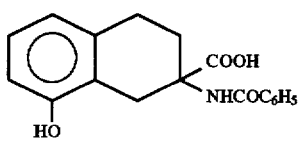
 IX
-continued
Reaction Scheme 1
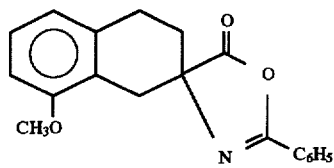 X
Reaction Scheme 2
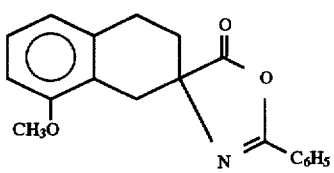
X
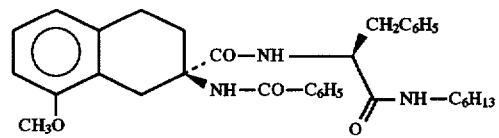
 XIb
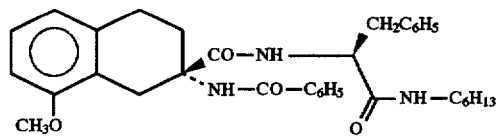
 XIa
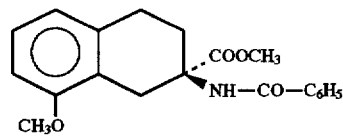
 XIIb
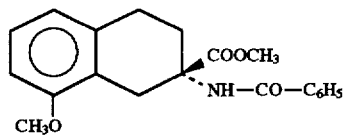
 XIIa -continued
Reaction Scheme 2

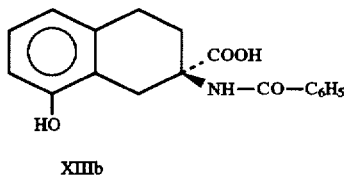

XIIIb

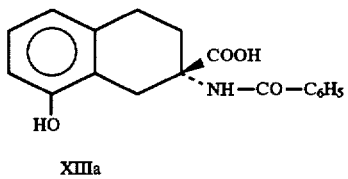

XIIIa

V→VI 1,7-Dihydroxynaphthalene (V) can be converted by means of lithium in liquid ammonia/tetrahydrofuran/tert.-butanol into 8-hydroxy-1,2,3,4-tetrahydronaphthalen-2-one, which can be converted —without the necessity of isolation—by means of sodium hydrogen sulphite into sodium (rac)-2,8-dihydroxy-1,2,3,4-tetrahydronaphthalene-2-sulphonate (VI).

VI→VII

The sodium salt of formula VI can be converted into the racemic spiro compound of formula VII by means of potassium cyanide and ammonium carbonate in ethanol/water.

VII→VIII

The spiro compound of formula VII can be converted into (rac)-2-amino-8-hydroxy-1,2,3,4-tetrahydronaphthalene-2-carboxylic acid (VIII) by heating with barium hydroxide in water and subsequent acidification, e.g. with aqueous sulphuric acid.

VIII→IX

The compound of formula VIII is firstly acylated by means of benzoyl chloride or the like, conveniently in the presence of an acid-binding agent such as sodium hydroxide or the like. By treating the acylation product with sodium hydroxide in dioxan there can be obtained (rac)-2-benzamido-8-hydroxy-1,2,3,4-tetrahydronaphthalene-2-carboxylic acid.

IX→X

By treating the compound of formula IX with dicyclohexylcarbodiimide in dichloromethane or the like and subsequent methylation, conveniently by means of dimethyl sulphate in the presence of a strong base such as sodium hydride in dioxan or the like, there can be obtained (rac)-3,4-dihydro-8-methoxy-2-phenylspiro-[naphthalene-2(1H), 4'(5'H)-oxazol]-5'-one.

X→XIa and XIb

The compound of formula X can be converted by means of L-phenylalanine cyclohexylamide into a mixture of the two diaster-eoisomeric compounds of formulae XIa and XIb, which can be separated by crystallization into its components XIa and XIb.

XIa→XIIa and XIb→XIIb

By treating the compound of formula XIa or XIb with trifluoromethanesulphonic acid there is obtained L-phenylalanine cyclohexylamide trifluoromethanesulphonate and the compound of formula XIIa or XIIb.

XIIa→XIIIa and XIIb→XIIIb

By treating the compound of formula XIIa or XIIb with boron tribromide in dichloromethane or the like there is obtained the compound of formula XIIIa or XIIIb.

Various transformations, which are illustrated in Reaction Scheme 3 hereinafter, are possible starting from the compound of formula XIIIa; the same transformations are, of course, also possible starting from the compound of formula XIIIb.

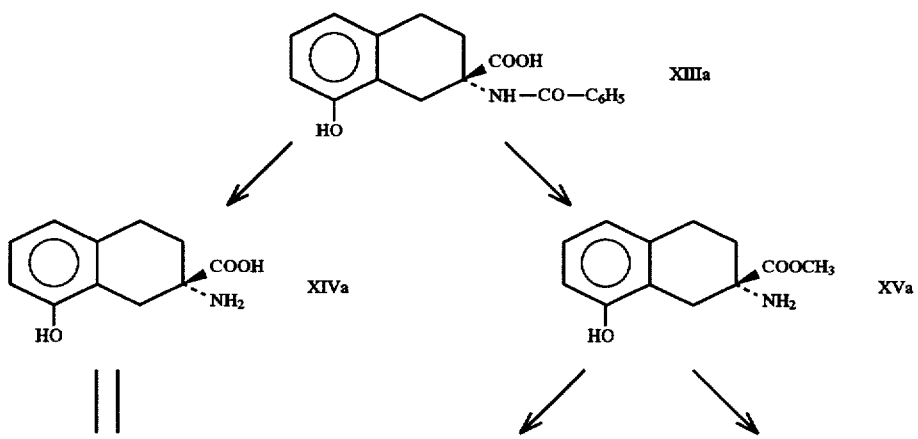

-continued
Reaction Scheme 3

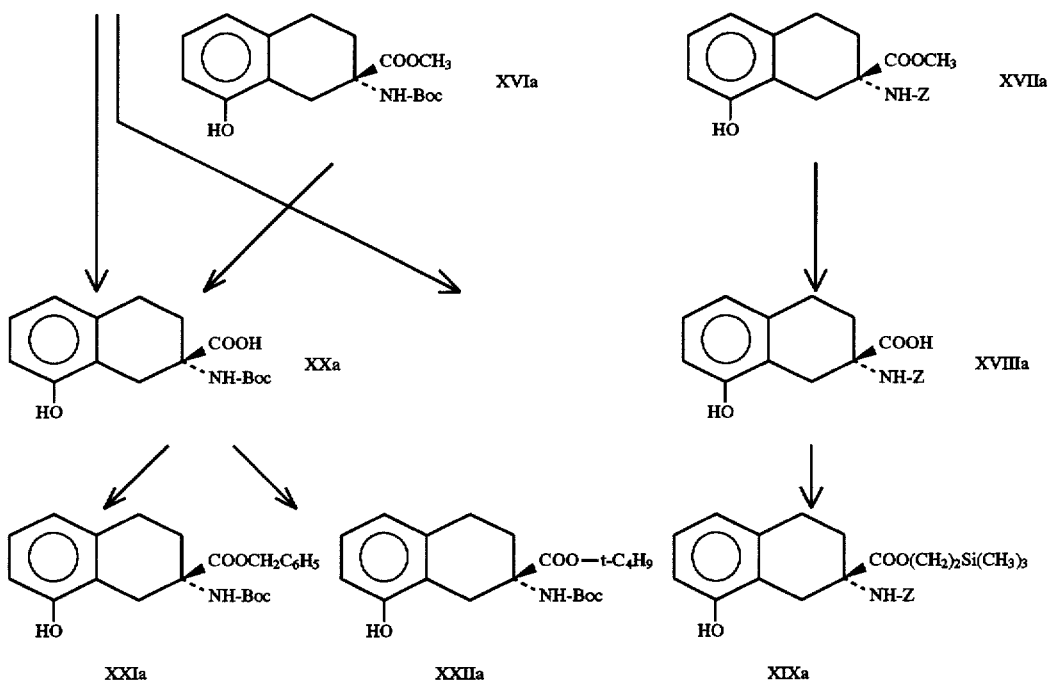

Z signifies benzyloxycarbonyl
Boc signifies tert.-butyloxycarbonyl

The various transformations according to Reaction Scheme 3 are known per se and will be familiar to any person skilled in the art, conveniently by means of the reagents referred to hereinafter.

XIIIa→XIVa
25% hydrochloric acid in dioxan at 100° (bomb tube).
XIIIa→XVa
25% hydrochloric acid in dioxan at 100° (bomb tube), then oxalyl chloride in methanolic hydrochloric acid.
XVa→XVIa
Di-tert.-butyl dicarbonate in dimethylformamide.
XVa→XVIIa
N-(Benzyloxycarbonyloxy)-succinimide and sodium hydrogen carbonate in dioxan.
XVIIa→XVIIIa
Lithium hydroxide in tetrahydrofuran/methanol/water.
XIVa→XVIIIa
N-(Benzyloxycarbonyloxy)-succinimide and sodium hydrogen carbonate in dioxan.
XVIIIa→XIXa
Trimethylsilylethanol/N-ethyl-N'-(3-dimethylaminopropyl)carbodiimide hydrochloride/1-N-hydroxybenzotriazole/ethyldiisopropylamine/N,N-dimethylaminopyridine in dimethylformamide.
XIVa→XXa
Di-tert.-butyl dicarbonate/trimethylchlorosilane/ethyldiisopropylamine in dichloromethane.
XVIa→XXa
Lithium hydroxide in tetrahydrofuran/methanol/water.
XXa→XXIa
Benzyl bromide/1,8-diazabicyclo[5.4.0]undec-7-ene in dimethylformamide or phenyldiazomethane in dichloromethane.
XXa→XXIIa
N,N-Dimethylformamide di-tert.-butyl acetal in toluene.

Compounds of type XVIa, XVIIa, XIXa, XXIa and XXIIa can be brominated in the 5-position, conveniently by means of N-bromosuccinimide in trifluoroethanol, and subsequently already at this stage certain additional variations (as described in more detail below) in the 5-position of the tetrahydronaphthalene structure are possible (see the different meanings of $R^1$ in formulae Ia and Ib), whereby the phenolic hydroxy group must be temporarily protected in certain instances. Furthermore, the phenolic hydroxyl group in compounds of type XVIa, XVIIa, XIXa, XXIa and XXIIa or in corresponding 5-bromo compounds or in transformation products thereof having other substituents in the 5-position can be replaced by a SH group, for example according to one of the following methods:

a) Reaction with N,N-diethyl-thiocarbamoyl chloride, followed by heating and then alkaline hydrolysis (see M.S. Newman, H. A. Karnes, J. Org. Chem. 31, 3980 (1966);

b) Treatment with trifluoromethanesulphonic anhydride in pyridine; then reaction of the resulting trifluoromethanesulphate with thiourea in the presence of a nickel catalyst, followed by treatment with alkali and then with acid, see K. Takagi, Chem. Lett. 1985, 1307.

Compounds of formulae IVa and IVb are obtained starting from compounds of type XVIa, XVIIa, XIXa, XXIa and XXIIa or from transformation products thereof, as previously described, or from corresponding compounds, but prepared from compound XIIIb by reaction with corresponding halo-arylcarboxylic acid esters such as benzyl 2-iodobenzoate, benzyl 3-bromothiophene-2-carboxylate, allyl 2-iodobenzoate, benzyl 2-bromo-5-nitrobenzoate, tert.-butyl 2-bromo-nicotinoate, allyl 2-bromo-nicotinoate and the like in pyridine in the presence of sodium hydride and of copper bromide-dimethyl sulphide complex.

Various transformations are possible in the compounds of formulae IVa and IVb obtained.

On the one hand, variations with respect to the protecting groups can be carried out. Thus, e.g., a tert.- butoxycarbonylamino group can be converted into a fluorenylmethoxycarbonylamino group, a tert.-butyl ester can be converted into a pentafluorophenyl ester or a benzyl ester can be converted into a pentafluorophenyl ester, which can be effected according to methods which are conventional and which will be familiar to any person skilled in the art.

On the other hand, variations with respect to the 5-position of the tetrahydronaphthalene structure are conveniently carried out at this stage; the introduction of bromine is, however, conveniently effected already at an earlier stage, namely at the stage of the compounds of type XVIa, XVIIa, XIXa, XXIa and XXIIa. Thus, compounds of formula IVa and IVb in which $R^1$ is bromine can be transformed, for example, as follows:

a) Reaction with organotin compounds in the presence of a palladium catalyst, see T. N. Mitchell, Synthesis 1992, 803–815; J. K. Stille, Angew. Chem. 98, 504–519 (1986); D. R. McKean, G. Parinello, A. F. Renaldo, J. K. Stille, J. Org. Chem. 52, 422 (1987). For example, by means of 3,4-dimethoxyphenylstannane in the presence of tetrakis-(triphenylphosphine)palladium in dioxan there is obtained a compound of formula IVa or IVb in which $R^1$ is 3,4-dimethoxyphenyl.

b) Reaction with boronates in the presence of a palladium catalyst, see X. Wang, V. Sniekus, Tetrahedron Lett. 1991, 4879; B. I. Alo, A. Kandil, P. A. Patil, M. J. Sharp, M. A. Siddiqui, V. Snieders, J. Org. Chem. 56, 3763 (1991); T.Oh-e, N. Miyaura, A. Suzuki, Synlett 1990, 221.

Methods a) and b) are suitable for the introduction of aryl, alkenyl, alkynyl and alkyl residues.

c) Reaction with carbon monoxide and an alcohol in the presence of palladium diacetate or the like and a base, see J. K. Stille, P. K. Wong, J. Org. Chem. 40,532 (1975); A. Cowell, J. K. Stille, J. Amer. Chem. Soc. 102, 4193 (1980). This method is suitable for the introduction of alkoxycarbonyl groups.

d) Reaction with carbon monoxide and hydrogen in the presence of triethylamine or the like and bis-(triphenylphosphine)palladium dichloride or the like, see A. Schoenberg, R. F. Heck, J. Amer. Chem. Soc. 96, 7761 (1974); H. Yoshida, N. Sugita, K. Kudo, Y. Takezaki, Bull. Chem. Soc. Japan 49, 1681 (1976). This method is suitable for the introduction of the formyl group.

e) Reaction with potassium cyanide in the presence of 1,1'-bis-(diphenylphosphino)-ferrocene and bis-(dibenzylideneacetone)-di-palladium in N,N-dimethylacetamide, see K. Takagi, Y. Sakakibara, Chem. Lett. 1989, 1957. This method is suitable for the introduction of the cyano group.

f) Transformation of the formyl group into an alkenyl group by Wittig reaction.

g) Treatment with tert.-butyllithium and subsequent reaction with suitable electrophiles such as e.g. N-formylpiperidine (yields formyl), chloroformic acid ester (yields alkoxycarbonyl) etc.

h) Ullmann coupling with a phenol in the presence of sodium hydride and copper bromide-dimethyl sulphide complex in pyridine, see D. L Boger, D. Yohannes, J. Org. Chem. 55, 6000 (1990); D. A. Evans, J. A. Ellmann, J. Amer. Chem. Soc. 111, 1063 (1989). This method is suitable for the introduction of aryloxy groups.

i) Reaction of alcohols, especially primary alcohols, under phase transfer catalysis (e.g. PEG-6000, KOH), see R. Neumann, Y. Sasson, Tetrahedron 39, 3437 (1983). This method is suitable for the introduction of alkoxy and aralkoxy groups.

k) Transformation of the formyl group into the hydroxy group by means of a modified Bayer-Villiger reaction (sodium percarbonate/trifluoroacetic acid), see G. Olah, Synthesis 1991, 739.

Compounds of formula IIa or IIb can be obtained starting from compounds of formula IVa or IVb by firstly liberating the amino group protected by $Z^2$, then coupling with an amino acid component yielding the residue $A^2$ or $A^4$ and thereupon coupling with an amino acid component yielding the residue $A^1$ or $A^3$, subsequently cyclizing and subsequently liberating the carboxyl group protected by $Z^3$. In the course of this synthesis certain variations can be effected at other positions of the molecule. Thus, a nitro group situated in the residue Y can be reduced to the amino group, which can be acylated.

Compounds of formula IIIa or IIIb can be obtained starting from compounds of formula IVa or IVb by firstly liberating the carboxyl group protected by $Z^3$, coupling this with a peptide component yielding the residue $R^2$, thereupon liberating the amino group protected by $Z^2$ and then coupling with an amino acid component yielding the residue $A^2$ or $A^4$ and thereupon coupling with an amino acid component yielding the residue $A^1$ or $A^3$.

The preparation of the compounds of formula IIa or IIb and of formula IIIa or IIIb from the compounds of formula IVa or IVb is effected according to methods which are conventional in peptide chemistry and which will be familiar to any person skilled in the art.

If an aspartic acid derivative is used in the course of this synthesis as the amino acid component yielding the residue $A^1$ or $A^3$, then in the resulting compound the carboxyl group of the aspartyl residue can be present not in free form, but as a member of a five-membered ring which is formed with the nitrogen atom of the amide bond linking $A^1$ or $A^3$ with $A^2$ or $A^4$; this ring can—conveniently only after the conversion into a compound of formula Ia or Ib—be opened, e.g. by means of lithium hydroxide or the like.

The compounds of formulae Ia and Ib wherein $R^2$ is a chain of amino acid residues contain amino acid sequences, whereby in the compounds of formula Ia the conformations of dextrorotating peptidic α-helices (with L-amino acid residues) are stabilized and the conformations of levorotating peptidic α-helices (with D-amino acid residues) are destabilized, whereas in the compounds of formula Ib the conformations of levorotating peptidic α-helices (with D-amino acid residues) are stabilized and the conformations of dextrorotating peptidic α-helices (with L-amino acid residues) are destabilized.

The structural elements in the compounds of formula Ia or Ib corresponding to the compounds of formula IIa or IIb can be perceived as mimetics of an α-helical winding. The stabilization or induction of the helicity in compounds of formula Ia or Ib is due to the fact that on the one hand the i→i+4 hydrogen bridge network which is characteristic of α-helices [see L. Pauling, R. B. Corey, H. R. Branson, Proc. Natl. Acad. Sci, 37, 205 (1951)] can form and that on the other hand the 2-amino-12,3,4-naphthalene-2-carboxylic acid building block induces inherent α-helical conformations at the asymmetric C-atom in the 2-position, see C. Spiegler, "Synthesis and conformational studies of peptides containing novel α,α-disubstituted amino acids," Dissertation Universität Zürich, 1993).

The calculation of α-helicity of the compounds of formulae Ia and Ib may be made by any conventional means.

The calculation is preferably performed based upon circular dichroism measurements of samples of the test compounds in solution by means well known in the art. Such measurements and calculations may be performed as described in Y.-H. Chen, J. T. Wang, H. H. Martinez, *Biochemistry*, 11, 4120 (1972)

Comparison of the induction or reduction of α-helicity in a polypeptide was performed using both configurations of the N-Cap of the invention, and without an N-Cap. As will be evident from FIG. 1, the helicity determined in trifluoroethanol/water (1:1) of the end product of Example 8.1.a is 87%, that of the end product of Example 8.1.b is 0% and that of a reference peptide of the same length is 50% [the calculation of the helicity was carried out analogously to Y.-H. Chen, supra, and G. Chi Chen, J. P. Kane, *Biochemistry*, 13, 3330 (1974)]. The results as shown in FIG. 1 demonstrate that the N-Capped polypeptides of the invention have an increased and decreased α-helicity in comparison to the non-N-Capped polypeptide.

Figure 2A:
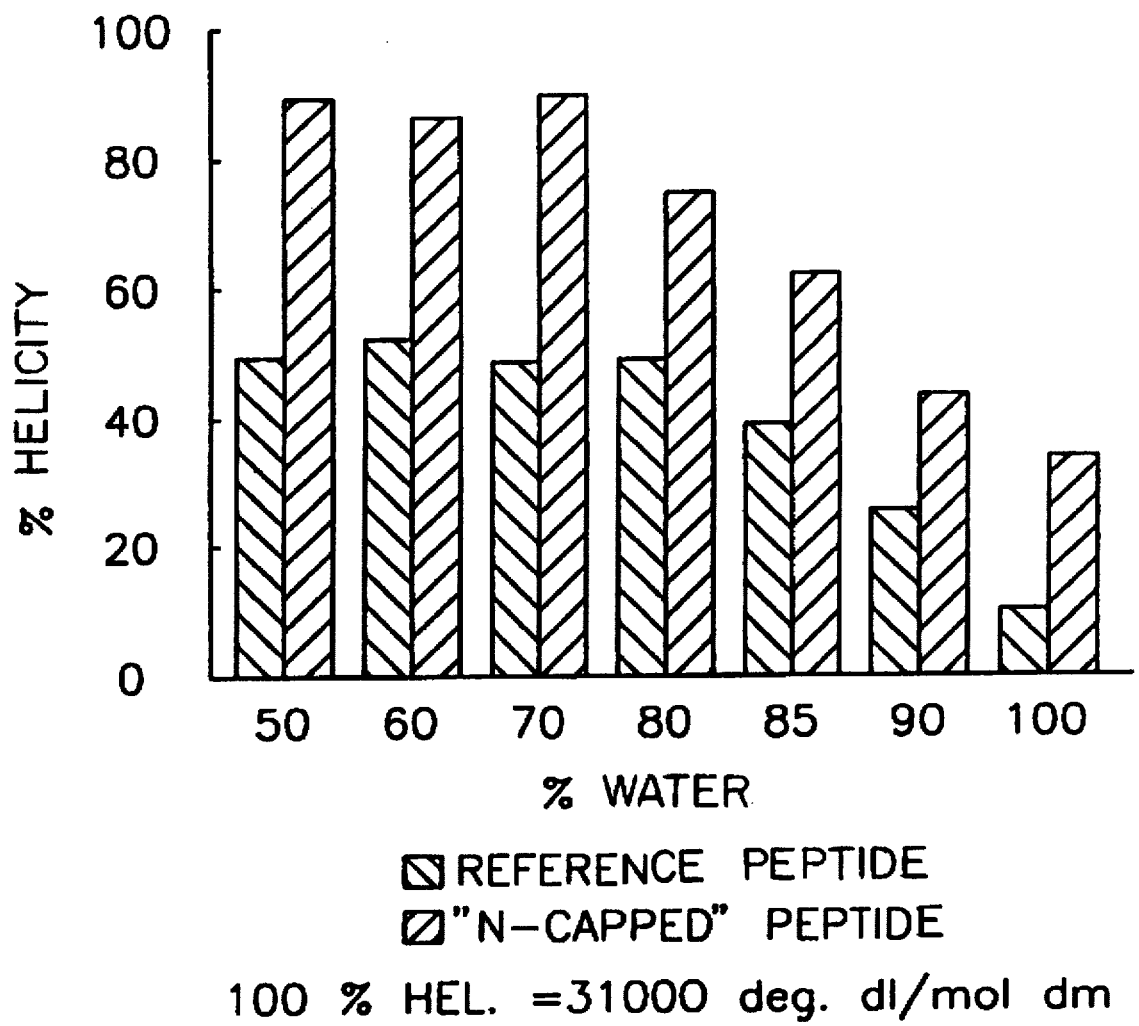
FIG. 2: shows a comparison of the helicity of a polypeptide, with an N-Cap and without an N-Cap but with an Ac-(Ala)$_3$ residue instead.
Figure 2B:
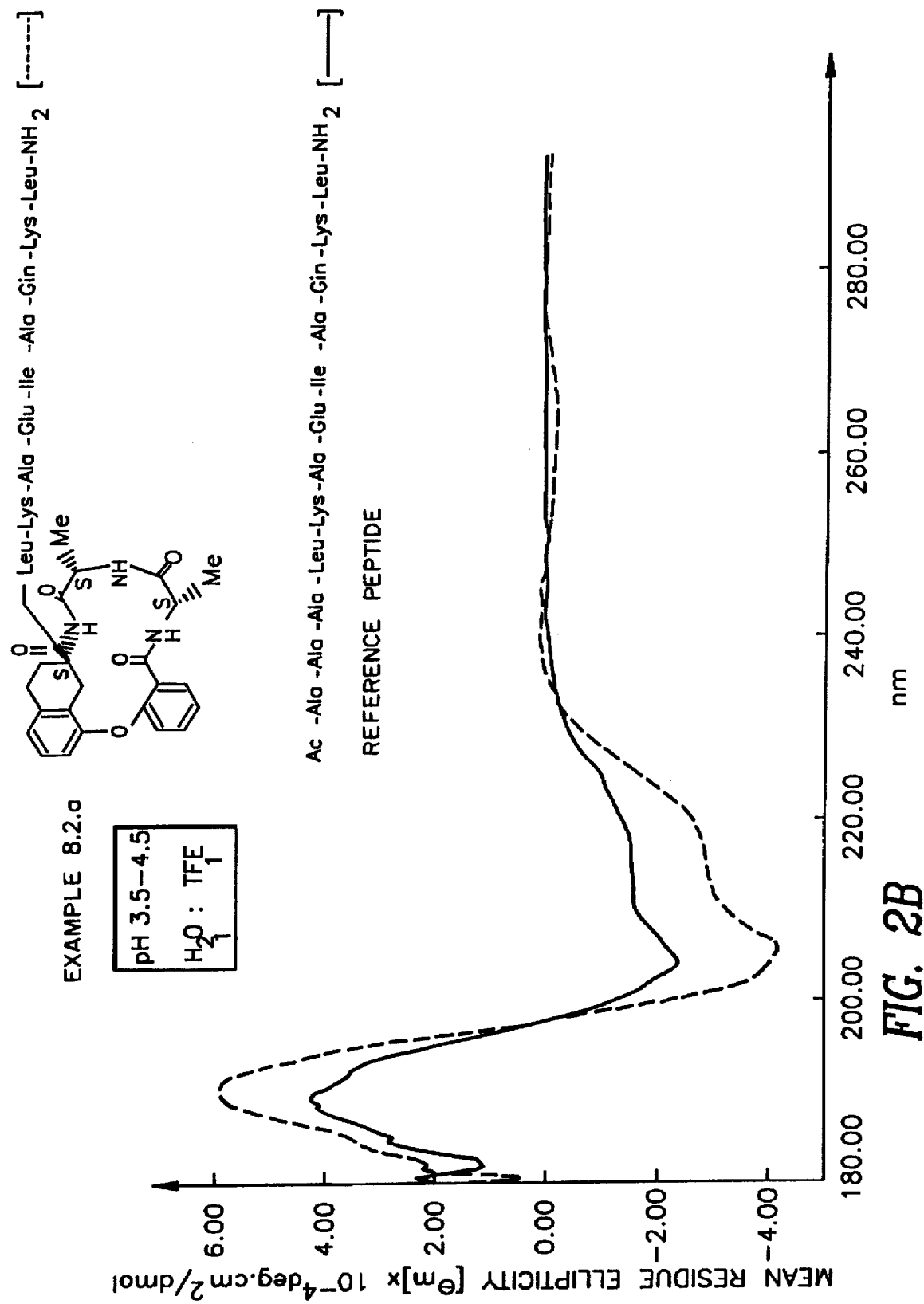

The significant stabilization of the α-helical conformation which occurs with the N-Capped polypeptides of the invention can also be observed in pure water. As will be evident from FIG. 2, the helicity of the end product of Example 8.2.a is 40%, but for the reference peptide of the same length only about 10%.

The priority of the amino acid residues $A^1$ and $A^2$ or $A^3$ and $A^4$ in the compounds of formula Ia or Ib is somewhat analogous to the compatibility to the L- and D-amino acids in peptidic α-helices, see A. Horovitz, J. M. Matthews, A. R. Fersht, *J. Mol. Biol.*, 227, 560–568 (1992).

Having regard to their properties, compounds of formula Ia or Ib are suitable as mimetics of exposed helical domains of proteins in order to clarify their rôle with respect to interactions with other proteins (receptors, enzymes or the like) or with DNA or RNA. In particular, the amino acid sequences which are the source of biological activity in a protein can be determined by means of compounds of formula Ia or Ib. The compounds of formula Ia or Ib are therefore suitable as research tools in order to identify biologically active peptide sequences. The compounds of formula Ia or Ib are, however, also potentially suitable as medicaments, with the respective therapeutic applicability depending upon their ability as mimetics of the domains of peptides or proteins which can interact with other proteins or with DNA or RNA through α-helical conformation, from which $R^2$ is derived.

In the following Examples, which illustrate the invention in more detail but are not intended to limit its scope in any manner, all temperatures are given in degrees Celsius. The designation of the Examples in which the end products have the S configuration at the asymmetric C atom in the 2 position of the 2-amino-1,2,3,4-tetrahydro-naphthalene-2-carboxylic acid building block always ends with "a", that of the Examples in which the end products have the R configuration at the C atom in question invariably ends with "b".

EXAMPLE 1.1

15.0 g of lithium metal pieces were added within 20 minutes under argon and while cooling (dry ice/acetone) analogously to D. W. Johnson, L. N. Mander, Aust. J. Chem. 1974, 27, 1277 to a solution of 120.0 g (750 mmol) of 1,7-dihydroxy-naphthalene in a mixture of 300 ml of tetrahydrofuran, 142 ml of tert-butyl alcohol and 1000 ml of liquid ammonia. The mixture was stirred for 1 hour and then treated with 400 ml of methanol, whereupon the mixture was stirred at −70° for 1 hour, the ammonia was removed under a $N_2$ stream, the residue was acidified with aqueous 10% HCl and extracted with 3×2.0 l of ethyl acetate. The organic phase was washed twice with 1.0 l of saturated sodium chloride solution, dried over $MgSO_4$ and evaporated. The residue was dissolved in 500 ml of ethyl acetate and 40 ml of ethanol, whereupon the solution was treated with 1.0 l of 38–40% sodium hydrogen sulphite solution and the mixture was shaken for 18 hours. The precipitate was filtered off, washed with dilute $NaHSO_3$ solution and ethyl acetate and dried in a vacuum over Sicapent, 96.2 g (48%) of sodium (rac)-2,8-dihydroxy-1,2,3,4-tetrahydro-naphthalene-2-sulphonate being obtained; m.p. 160°–162°.

EXAMPLE 1.2

A suspension of 48.0 g (180 mmol) of sodium (rac)-2,8-di-hydroxy-1,2,3,4-tetrahydro-naphthalene-2-sulphonate, 20.2 g (310 mmol) of potassium cyanide and 118.1 g (1 mol) of ammonium carbonate in 800 ml of ethanol/water (4:1) was stirred at 65° internal temperature for 2 hours, then cooled and poured into a mixture of ice and 1.2 l of 2N aqueous HCl. The suspension was left to stand overnight and was then filtered. The residue was washed with $H_2O$ and dried in a vacuum over Sicapent, 31.5 g (75.4%) of (rac)-3',4'-dihydroxy-8'-hydroxyspiro[imidazolidine-4,2'(1'H)-naphthalene]-2,5-dione being obtained; m.p. 232°–234° (dec.).

EXAMPLE 1.3

A suspension of 30.0 g (129 mmol) of (rac)-3',4'-dihydroxy-8'-hydroxyspiro[imidazolidine-4,2'(1'H)-naphthalene]-2,5-dione and 203.8 g of $Ba(OH)_2.8H_2O$ in 800 ml of water was stirred at 125° in a steel autoclave for 24 hours, then cooled, acidified with 4N $H_2SO_4$ solution, whereupon the mixture was heated on a water bath for 1 hour, cooled, filtered and the filter residue was washed with dilute $H_2SO_4$ solution. The acidic filtrate was concentrated to a volume of about 300 ml and neutralized with concentrated aqueous ammonia solution, whereupon a precipitate separated. The suspension was left to stand overnight and was then filtered. The residue was dried in a vacuum over Sicapent, 20.5 g (83.1%) of (rac)-2-amino-8-hydroxy-1,2,3,4-tetrahydro-naphthalene-2-carboxylic acid being obtained; m.p. >280° (dec.).

EXAMPLE 1.4

50 ml of 2N NaOH and 40.3 ml (345 mmol) of benzoyl chloride were simultaneously added dropwise from 2 dropping funnels into a solution of 19.0 g (99.4 mmol) of (rac)-2-amino-8-hydroxy-1,2,3,4-tetrahydro-naphthalene-2-carboxylic acid in 210 ml of 1N NaOH while cooling with ice and stirring in such a manner that the internal temperature did not rise above 15°. The reaction mixture was subsequently brought slowly to room temperature, stirred for 2 hours, acidified with 2N HCl and extracted twice with 250 ml of ethyl acetate. The combined organic phases were dried over $MgSO_4$ and evaporated. The residue was dissolved in 300 ml of dioxan and the solution was treated with 150 ml of 2N NaOH while cooling with ice. The reaction mixture was stirred overnight, acidified with 4N HCl and extracted three times with 300 ml of ethyl acetate. The combined organic phases were dried over $MgSO_4$ and evaporated. The residue was taken up in 500 ml of diethyl ether/hexane (4:1) and the suspension was stirred overnight and then filtered. The filter residue was dried in a high vacuum, 28.6 g (92.4%) of (rac)-2-benzamido-8-hydroxy-1,2,3,4-tetrahydro-naphthalene-2-carboxylic acid being obtained. M.p. 234–236° (dec.).

EXAMPLE 1.5

12.53 g (60.7 mmol) of N,N-dicyclohexylcarbodiimide were added portionwise while cooling to a suspension of 18.0 g (57.8 mmol) of (rac)-2-benzamido-8-hydroxy-1,2,3,4-tetrahydronaphthalene-2-carboxylic acid in 150 ml of dichloromethane. The mixture was stirred at room temperature for 2 hours and then filtered, whereupon the filter residue was washed with dichloromethane. The filtrate was evaporated and the residue was dried in a high vacuum and dissolved in 150 ml of absolute dioxan. The solution was treated portionwise with 2.80 g of sodium hydride suspension (55%) while cooling with ice and under argon, whereupon the mixture was stirred at room temperature for 30 minutes and then 16.5 ml of dimethyl sulphate were added. The suspension was stirred at 80° for 1 hour, cooled and then poured into a mixture of ice, 10% sodium hydrogen phosphate solution and ethyl acetate. The aqueous phase was extracted with ethyl acetate and the combined organic phases were dried over $MgSO_4$ and concentrated. The residue was chromatographed on 500 g of silica gel with ethyl acetate/hexane (1:4), there being obtained after crystallization from diethyl ether/hexane (1:2) and drying in a high vacuum 13.6 g (76.5%) of (rac)-3,4-dihydro-8-methoxy-2'-phenyl-spiro[naphthalen-2(H),4'(5'H)-oxazol]-5'-one. M.p. 108–109°.

EXAMPLE 1.6

A mixture of 12.6 g (41 mmol) of (rac)-3,4-dihydro-8-methoxy-2'-phenyl-spiro[naphthalen-2(H),4'(5'H)-oxazol]-5'-one and 15.15 g (61.5 mmol) of L-phenylalanine cyclohexylamide in 120 ml of N-methylpyrrolidone was stirred at 60° for 18 hours, then cooled and subsequently poured into a mixture of 300 ml of water and 500 ml of ethyl acetate. The organic phase was extracted twice with 250 ml of 0.5N HCl and the combined aqueous phases were extracted with ethyl acetate. The combined organic phases were washed with saturated sodium chloride solution, dried over $MgSO_4$ and evaporated. The residue was suspended in 300 ml of ethyl acetate for 2 hours, whereupon the suspension was filtered and the residue was washed with ethyl acetate, recrystallized from ethyl acetate/hexane (6:1) and dried. There were obtained 10.44 g (46%) of $N^2$-[(S)-2-benzamido-8-methoxy-1,2,3,4-tetrahydro-naphthalene-2-carbonyl]-L-phenylalanine cyclohexylamide. M.p. 186°–188°. $[\alpha]_D=+12.0°$ (c=0.2, methanol).

The filtrate was concentrated and the residue was chromatographed on 1 kg of silica gel with diethyl ether/isopropanol (99.5:0.5), whereupon after recrystallization from ethyl acetate/hexane (1:1) and drying in a high vacuum 10.25 g (45.2%) of $N^2$-[(R)-2-benzamido-8-methoxy-1,2,3,4-tetrahydro-naphthalene-2-carbonyl]-L-phenylalanine cyclohexylamide were obtained. M.p. 191°–192°. $[\alpha]_D=-21.0°$ (c=0.2, methanol).

EXAMPLE 1.7.a 7.1 ml (80.74 mmol) of trifluoromethanesulphonic acid were added dropwise under argon and while cooling with ice to a suspension of 7.5 g (13.54 mmol) of $N^2$-[(R)-2-benzamido-8-methoxy-1,2,3,4-tetrahydro-naphthalene-2-carbonyl]-L-phenylalanine cyclohexylamide in 35 ml of methanol. The mixture was stirred at 80° in a bomb tube for 4 hours, then cooled and subsequently concentrated to a volume of ~20 ml. 50 ml of dichloromethane were added while stirring, the suspension was filtered and the fitter residue was washed with dichloromethane and dried, 4.48 g (83%) of L-phenylalanine cyclohexylamide trifluoromethanesulphonate being isolated. The filtrate was washed with water, dried over $MgSO_4$ and concentrated. The residue was chromatographed on 350 g of silica gel with ethyl acetate/hexane (2:3), whereupon 4.0 g (87%) of methyl (S)-2-benzamido-8-methoxy-1,2,3,4-tetrahydronaphthalene-2-carboxylate were obtained. $[\alpha]_D=+144.0°$ ($CHCl_3$, c=0.2). IR(KBr): 3366w(br.), 3062w, 2998w, 2948w, 1739s, 1647s, 1586m, 1527s, 1468s, 1437m, 1292m, 1259s, 1099m, 1047m, 774w, 713m. (D. Obrecht, Helv. Chim. Acta 1992, 75, 1666).

EXAMPLE 1.7.b

In analogy to Example 1.7.a, from 8.79 g (15.87 mmol) of $N^2$-[(R)-2-benzamido-8-methoxy-1,2,3,4-tetrahydronaphthalene-2-carbonyl]-L-phenylalanine cyclohexylamide there were obtained 4.78 g (88%) of methyl (R)-2-benzamido-8-methoxy-1,2,3,4-tetrahydronaphthalene-2-carboxylate. $[\alpha]_D=-142.5°$ (c=0.2, $CHCl_3$).

EXAMPLE 1.8.a.

28.7 ml of boron tribromide solution (1M in dichloromethane) were added dropwise under argon and while cooling with ice to a solution of 1.95 g (5.75 mmol) of methyl (S)-2-benzamido-8-methoxy-1,2,3,4-tetrahydronaphthalene-2-carboxylate in 15 ml of dichloromethane. The reaction mixture was stirred at 0° for 30 minutes and at room temperature for 3 hours and then poured into a mixture of ice, saturated ammonium chloride solution and ethyl acetate. The organic phase was separated, extracted with saturated sodium chloride solution, dried over $MgSO_4$ and concentrated. The residue was dried in a high vacuum, suspended in diethyl ether/hexane (1:4) and filtered off. The filter residue was dried, there being obtained 1.75 g (97.8%) of (S)-2-benzamido-8-hydroxy-1,2,3,4-tetrahydro-naphthalene-2-carboxylic acid. $[\alpha]_D=+84.3°$ (c=0.3, methanol). IR (KBr): 3362m(br.), 3064w, 3022w, 2976w, 2938w, 2620w, 1718s, 1644s, 1588m, 1523s, 1487m, 1467s, 1330m, 1278s, 1082w, 716m.

EXAMPLE 1.8.b

In analogy to Example 1.8.a, from 2.71 g (7.98 mmol) of methyl (R)-2-benzamido-8-methoxy-1,2,3,4-tetrahydro-naphthalene-2-carboxylate there were obtained 2.42 g (97.4%) of (R)-2-benzamido-8-hydroxy-1,2,3,4-tetrahydro-naphthalene-2-carboxylate acid. $[\alpha]_D=-85.7°$ (c=0.3, methanol).

EXAMPLE 2.1.a

A solution of 1.75 g (5.62 mmol) of (S)-2-benzamido-8-hydroxy-1,2,3,4-tetrahydro-naphthalene-2-carboxylic acid in 12 ml of 25% hydrochloric acid and 6 ml of dioxan was heated to 110° in a bomb tube for 8 hours, then cooled and subsequently evaporated to dryness. The residue was dried overnight in a high vacuum over Sicapent and then suspended in 20 ml of diethyl ether while stirring, whereupon the suspension was filtered, the filter residue was washed with diethyl ether and dried in a high vacuum and then dissolved in 3 ml of methanol and 3 ml of 15% methanolic hydrochloric acid. The solution was treated with 0.42 ml (3.89 mmol) of oxalyl chloride under argon and while cooling with ice, whereupon the mixture was stirred at 50° in a bomb tube for 20 hours, then cooled and subsequently poured into a mixture of saturated sodium hydrogen carbonate solution and chloroform. The aqueous phase was extracted with chloroform/methanol (6:1). The combined organic phases were dried over MgSO₄, filtered and concentrated. The residue was chromatographed on 150 g of silica gel with chloroform/methanol (6:1), there being obtained after recrystallization from ethyl acetate/hexane 1.05 g (84.4%) of methyl (S)-2-amino-8-hydroxy-1,2,3,4-tetrahydro-naphthalene-2-carboxylate. M.p. 183°–185°. [α]$_D$=−22.7° (c=0.15, methanol).

EXAMPLE 2.1.b

In analogy to Example 2.1.a, from 2.40 g (7.71 mmol) of (R)-2-benzamido-8-hydroxy-1,2,3,4-tetrahydro-naphthalene-2-carboxylic acid there were obtained 1.60 g (95.3%) of methyl (R)-2-amino-8-hydroxy-1,2,3,4-tetrahydro-naphthalene-2-carboxylic acid. M.p. 184°–185°.

EXAMPLE 2.2.a

A suspension of 9.2 g (29.55 mmol) of (S)-2-benzamido-8-hydroxy-1,2,3,4-tetrahydro-naphthalene-2-carboxylic acid in 45 ml of dioxan and 62 ml of 25% hydrochloric acid was heated to 100° in a bomb tube for 24 hours, then cooled, concentrated to half of the volume and extracted with ethyl acetate. The organic phase was washed with water, whereupon the combined aqueous phases were reduced to a volume of 200 ml and adjusted to pH 7 with concentrated ammonia solution. The solution obtained was filtered over MCl gel (CHP20P; 75–150 µ) (water, water/methanol (95:5) →water/methanol (9:1)), whereupon after drying over Sicapent 5.30 g (86.6%) of (S)-2-amino-8-hydroxy-,2,3,4-tetrahydro-naphthalene-2-carboxylic acid were obtained. M.p. >270° (dec.). [α]$_D$=+7.0° (c=0.2, 0.1N HCl).

EXAMPLE 2.2.b

In analogy to Example 2.2.a, from 4.50 g (14.45 mmol) of (R)-2-benzamido-8-hydroxy-1,2,3,4-tetrahydro-naphthalene-2-carboxylic acid there were obtained 2.49 g (83%) of (R)-2-amino-8-hydroxy-1,2,3,4-tetrahydro-naphthalene-2-carboxylic acid. M.p. >272° (dec.). [α]$_D$=−5.0° (c=0.2, 0.1N HCl).

EXAMPLE 2.3.a

A solution of 924 mg (4.24 mmol) of di-tert.-butyl dicarbonate in 1.5 ml of DMF was added while cooling with ice and under argon to a solution of 780 mg (3.53 mmol) of methyl (S)-2-amino-8-hydroxy-1,2,3,4-tetrahydro-naphthalene-2-carboxylate in 10 ml of DMF. The reaction mixture was stirred at 0° for 30 minutes and at room temperature for 18 hours and then poured into a mixture of water and ethyl acetate. The organic phase was separated, washed with water, dried over MgSO₄ and concentrated. The residue was chromatographed on 100 g of silica gel with ethyl acetate/hexane (1:2), whereupon after recrystallization from diethyl ether/hexane and drying 1.0 g (88.1%) of methyl (S)-2-(tert.butoxycarbonylamino)-8-hydroxy-1,2,3,4-tetrahydro-naphthalene-2-carboxylate was obtained. M.p. 186°–187°. [α]$_D$=+95.0° (c=0.2, chloroform).

EXAMPLE 2.3.b

In analogy to Example 2.3.a, from 1.46 g (6.60 mmol) of methyl (R)-2-amino-8-hydroxy-1,2,3,4-tetrahydro-naphthalene-2-carboxylate there were obtained 1.80 g (85%) of methyl (R)-2-(tert.butoxycarbonylamino)-8-hydroxy-1,2,3,4-tetrahydro-naphthalene-2-carboxylate. M.p. 186–187°. [α]$_D$=−93.5° (c=0.2, chloroform).

EXAMPLE 2.4.a

A suspension of 1.1 g (4.27 mmol) of methyl (S)-2-amino-8-hydroxy-1,2,3,4-tetrahydro-naphthalene-2-carboxylate in 22 ml of dioxan was treated at room temperature with 2.12 g (8.54 mmol) of N-(benzyloxycarbonyloxy)-succinimide and 717 mg (8.54 mmol) of sodium hydrogen carbonate. The reaction mixture was stirred at room temperature for 4 hours and then poured into a mixture of saturated sodium chloride solution and ethyl acetate. The organic phase was separated, dried over MgSO₄ and concentrated. The residue was chromatographed on 200 g of silica gel with chloroform/methanol (98:2→95:5), whereupon after drying 1.30 g (86.9%) of methyl (S)-2-benzyloxycarbonylamino-8-hydroxy-1,2,3,4-tetrahydro-naphthalene-2-carboxylate were obtained. M.p. 58°–68° (sintering). [α]$_D$=+85.0° (c=0.2, chloroform).

EXAMPLE 2.5.a

A solution of 800 mg (2.26 mmol) of methyl (S)-2-benzyl-oxycarbonylamino-8-hydroxy-1,2,3,4-tetrahydro-naphthalene-2-carboxylate in 10 ml of THF/methanol/water (3:1:1) was treated with 695 mg of lithium hydroxide.1 H₂O while cooling with ice. The reaction mixture was stirred at 0° for 1 hour and at room temperature for 3 hours and then poured into a mixture of ice, 0.5N hydrochloric acid solution and chloroform. The aqueous phase was separated and exhaustively extracted with chloroform. The combined organic fractions were dried over sodium sulphate and concentrated. After drying the residue 555 mg (72%) of (S)-2-benzyloxycarbonyl-8-hydroxy-1,2,3,4-tetrahydro-naphthalene-2-carboxylic acid were obtained as a beige powder. M.p. 68°–75° (sintering) [α]$_D$=+83.5° (c=0.2, chloroform).

EXAMPLE 2.6.a 143 mg (0.576 mmol) of N-(benzyloxycarbonyl)-succinimide and 80.6 mg (0.96 mmol) of sodium hydrogen carbonate were added to a suspension of 100 mg (0.48 mmol) of (S)-2-amino-8-hydroxy-1,2,3,4-tetrahydro-naphthalene-2-carboxylic acid in 2 ml of dioxan/water (1:1). The reaction mixture was stirred at room temperature overnight, then again treated with 40 mg (0.336 mmol) of sodium hydrogen carbonate and 83.6 mg (0.48 mmol) of N-(benzyloxycarbonyl)-succinimide, stirred at room temperature for 4 hours and then poured into a mixture of saturated sodium chloride solution and ethyl acetate. The organic phase was separated, dried over MgSO₄ and concentrated. The residue was chromatographed on 20 g of silica gel with chloroform/methanol/water (6:3:0.5), whereupon after drying 66 mg (38.7%) of (S)-2-benzyloxycarbonylamino-8-hydroxy-1,2,3,4-tetrahydro-naphthalene-2-carboxylic acid were obtained as a beige powder. M.p. 65°–75° (sintering).

EXAMPLE 2.7.a

5 A solution of 620 mg (1.82 mmol) of (S)-2-benzyloxycarbonylamino-8-hydroxy-1,2,3,4-tetrahydro-naphthalene-2-carboxylic acid in 6 ml of N,N-dimethylformamide was treated at 0° with 521 mg (2.73 mmol) of N-ethyl-N'-(3-dimethylaminopropyl)-carbodiimide hydrochloride, 489 mg (3.64 mmol) of 1-N-hydroxylbenzotriazole, 502 µl (2.91 mmol) of ethyldiisopropylamine and 627 µl (4.37 mmol) of trimethylsilylethanol. The reaction mixture was stirred at 0° for 1 hour, then treated with 50 mg of N,N-dimethylaminopyridine and a further 627 µl (4.37 retool) of trimethylsilylethanol, thereupon stirred at room temperature for 24 hours and subsequently poured into a mixture of water and dichloromethane. The aqueous phase was acidified with 0.1N hydrochloric acid and exhaustively extracted with dichloromethane. The combined organic phases were dried over MgSO$_4$ and concentrated. The residue was chromatographed on 100 g of silica gel with hexane/ethyl acetate (4:1→1:1), whereupon after drying 449 mg (56%) of trimethylsilylethyl (S)-2-benzyloxycarbonylamino-8-hydroxy-1,2,3,4-tetrahydro-naphthalene-2-carboxylate were obtained. M.p. 141°–144°.[α]$_D$=+68.0° (c=0.2, chloroform).

EXAMPLE 2.8.a 1.2 ml (9.50 mmol) of trimethylchlorosilane were added under argon and while cooling with ice to a suspension of 513 mg (2.68 mmol) of (S)-2-amino-8-hydroxy-1,2,3,4-tetrahydro-naphthalene-2-carboxylic acid in 10 ml of dichloromethane. The reaction mixture was heated at reflux for 30 minutes, cooled, treated at 0° with 1.7 ml (9.92 mmol) of ethyldiisopropylamine, subsequently stirred at room temperature for 15 minutes and under reflux for 2 hours, then cooled to 0° and finally treated with a solution of 650 mg (2.98 mmol) of di-tert.butyl dicarbonate in 0.6 ml of dichloromethane. The reaction mixture was stirred at room temperature for 40 hours and under reflux for 7 hours, then cooled and subsequently poured into a mixture of 40 ml of saturated sodium hydrogen carbonate solution and diethyl ether. The organic phase was separated and extracted twice with 30 ml of saturated sodium hydrogen carbonate solution. The combined aqueous phases were adjusted to pH 4 while cooling with ice and extracted three times with 100 ml of ethyl acetate. The combined organic phases were dried over Na$_2$SO$_4$ and concentrated, whereupon after drying in a high vacuum 820 mg (99.6%) of (S)-2-(tert.butoxycarbonylamino)-8-hydroxy-1,2,3,4-tetrahydro-naphthalene-2-carboxylic acid were obtained as an amorphous solid.

[α]$_D$=+66.0° (c=1.0, chloroform). IR (KBr): 3403m(br.), 3033w, 2979w, 2933w, 1717s, 1695s, 1589w, 1500w, 1467m, 1395m, 1368m, 1278m, 1164m, 1063w, 776w.

EXAMPLE 2.9.b

A solution of 465 mg (1.45 mmol) of methyl (R)-2-(tert.butoxycarbonylamino)-8-hydroxy-1,2,3,4-tetrahydro-naphthalene-2-carboxylate in 4.5 ml of tetrahydrofuran/methanol/water (3:1:1) was treated with 647 mg of lithium hydroxide.1H$_2$O while cooling with ice. The reaction mixture was stirred at 0° for 30 minutes and at room temperature for 2 hours and then poured into a mixture of chloroform/methanol (6:1) and 0.5N hydrochloric acid/ice. The organic phase was separated, dried over MgSO$_4$ and concentrated, whereupon after drying in a high vacuum 410 mg (92%) of (R)-2-(tert.butoxycarbonylamino)-8-hydroxy-1,2,3,4-tetrahydronaphthalene-2-carboxylic acid were obtained as an amorphous solid.

[α]$_D$=−65.4° (c=0.5, chloroform).

EXAMPLE 2.10.a

A suspension of 770 mg (250 mmol) of (S)-2-(tert.butoxycarbonylamino)-8-hydroxy-1,2,3,4-tetrahydro-naphthalene-2-carboxylic acid in 5 ml of toluene was treated with 1.80 ml (7.52 mmol) of N,N-dimethylformamide di-tert.butyl acetal. The reaction mixture was stirred at 70° for 6 hours and then cooled, whereupon a further 0.6 ml (2.50 mmol) of N,N-dimethylformamide di-tert.butyl acetal was added and the mixture was stirred at 70° for 3 hours. The reaction mixture was poured into a mixture of ice-water and ethyl acetate, whereupon saturated sodium chloride solution was added. The aqueous phase was separated and extracted with ethyl acetate. The combined organic phases were dried over Na$_2$SO$_4$ and concentrated. The residue was chromatographed on 170 g of silica gel with ethyl acetate/hexane (1:4), whereupon after drying 665 mg (73%) of tert.butyl (S)-2-(tert.butoxycarbonylamino)-8-hydroxy-1,2,3,4-tetrahydro-naphthalene-2-carboxylate were obtained as an amorphous solid. [α]$_D$=+65.5° (c=0.2, chloroform). IR (KBr): 3406m(br.), 2978m, 2932w, 1721s, 1695s, 1590m, 1497m, 1467m, 1394m, 1368s, 1303m, 1254m, 1162s, 1086m, 784w.

EXAMPLE 2.11.a

426 μl (2.86 mmol) of 1,8-diazabicyclo[5.4.2.0]undec-7-ene and 340 μl (2.86 mmol) of benzyl bromide were added while cooling with ice to a solution of 800 mg (2.60 mmol) of (S)-2-(tert.butoxycarbonylamino)-8-hydroxy-1,2,3,4-tetrahydro-naphthalene-2-carboxylic acid in 6 ml of N,N-dimethylformamide. The reaction mixture was stirred at room temperature for 18 hours and then poured on to ice-water, whereupon the mixture was exhaustively extracted with ethyl acetate. The combined organic phases were washed with saturated sodium chloride solution, dried over magnesium sulphate and concentrated. The residue was chromatographed on 120 g of silica gel with hexane/ethyl acetate (7:3), whereupon after drying in a high vacuum 829 mg (80.5%) of benzyl (S)-(tert.butoxycarbonylamino)-8-hydroxy-1,2,3,4-tetrahydronaphthalene- 2-carboxylate were obtained as a white foam. M.p. 51°–65° (sintering). [α]$_D$=+64.5° (c=0.2, chloroform).

EXAMPLE 2.12.b

A solution of 440 mg (1.43 mmol) of (R)-2-(tert.butoxycarbonylamino)-8-hydroxy-1,2,3,4-tetrahydro-naphthalene-2-carboxylic acid in 8 ml of dichloromethane was treated with 140 μl of phenyldiazomethane. The reaction mixture was stirred at room temperature for 1 hour and then concentrated. The residue was chromatographed on 50 g of silica gel with chloroform, whereupon 384 mg (70%) of benzyl (R)-2-(tert.butoxycarbonylamino)-8-hydroxy-1,2,3,4-tetrahydro-naphthalene-2-carboxylate were obtained as an amorphous solid. M.p. 56°–60°. [α]$_D$=−62.7° (c=1, chloroform).

EXAMPLE 3.1.a 110 mg (0.62 mmol) of N-bromosuccinimide were added portionwise under argon and while cooling with ice to a solution of 200 mg (0.62 mmol) of methyl (S)-2-(tert.butoxycarbonylamino)-8-hydroxy-1,2,3,4-tetrahydro-naphthalene-2-carboxylate in 4 ml of trifluoroethanol. The reaction mixture was stirred at 0° for 1 hour and at room temperature for 1 hour and then poured into a mixture of saturated sodium hydrogen carbonate solution and chloroform. The organic phase was separated, washed with sodium chloride solution, dried over MgSO$_4$ and concentrated. The residue was chromatographed on 60 g of silica gel with ethyl acetate/hexane (1:9→4:6), whereupon after drying in a high vacuum 220 mg (88.6%) of (S)-5-bromo-2-(tert.butoxycarbonylamino)-8-hydroxy-1,2,3,4-tetrahydronaphthalene-2-carboxylate were obtained. M.p. >180° (dec.). MS: 400 (M$^+$, <1), 343(2), 284, 282(100), 144(52), 57(96).

EXAMPLE 4.1.a

A solution of 1.0 g (311 mmol) of methyl (S)-2-(tert.butoxycarbonylamino)-8-hydroxy-1,2,3,4-tetrahydronaphthalene-2-carboxylate in 9 ml of pyridine was treated with 180 mg of sodium hydride dispersion (55%) while cooling with ice and under argon. The mixture was stirred at 0° for 30 minutes, treated with 966 mg (3.73 mmol) of copper bromide-dimethyl sulphide complex and with 3.06 g (9.33 mmol) of benzyl 2-iodobenzoate, brought to room temperature, stirred at 120° for 2 hours, cooled and poured into a mixture of ice, 0.5N hydrochloric acid and ethyl acetate. The organic phase was separated, washed with 0.5N hydrochloric acid and saturated sodium chloride solution, dried over $MgSO_4$ and concentrated. The residue was chromatographed on 140 g of silica gel with ethyl acetate/hexane (1:3), whereupon after drying in a high vacuum 1.47 g (87%) of methyl (S)-8-(2-benzyloxycarbonyl-phenoxy)-2-(tert.butoxycarbonylamino)-1,2,3,4-tetrahydro-naphthalene-2-carboxylate were obtained as an amorphous solid. $[\alpha]_D$=+47.0° (c=0.2, chloroform). IR (KBr): 3392w (br.), 3065w, 3035w, 2976w, 2949w, 1740s, 1714s, 1604w, 1484m, 1455m, 1367w, 1295m, 1250s, 1165m, 1081 m, 777w, 698w.

EXAMPLE 4.1.b

In analogy to Example 4.1.a, from 250 mg (0.78 mmol) of methyl (R)-2-(tert.butoxycarbonylamino)-8-hydroxy-1,2,3,4-tetrahydronaphthalene-2-carboxylate in 2 ml of pyridine with 40 mg of sodium hydride dispersion, 226 mg (1.09 mmol) of copper bromide-dimethyl sulphide complex and 510 mg (1.56 mmol) of benzyl 2-iodobenzoate there were obtained 350 mg (84.4%) of methyl (R)-8-(2-benzyloxycarbonyl-phenoxy)-2-(tert.butoxycarbonylamino)-1,2,3,4-tetrahydro-naphthalene-2-carboxylate as an amorphous solid. $[\alpha]_D$=−53.0° (c=0.2, chloroform).

EXAMPLE 4.2.a

In analogy to Example 4.1.a, 500 mg (1.55 mmol) of methyl (S)-2-(tert.butoxycarbonylamino)-8-hydroxy-1,2,3,4-tetrahydronaphthalene-2-carboxylate in 1.5 ml of pyridine were reacted with 124 mg of sodium hydride dispersion, 876 mg (4.26 mmol) of copper bromide-dimethyl sulphide complex and 1.36 g (4.57 mmol) of benzyl 3-bromothiophene-2-carboxylate at 130° for 3 hours. After chromatography on 450 g of silica gel with ethyl acetate/hexane (9:1→4:1) there were obtained after drying in a high vacuum 338 mg (46%) of benzyl (S)-3-(7-tert.butoxycarbonylamino-7-methoxycarbonyl- 5,6,7,8-tetrahydro-naphthalene-1-yloxy) thiophene-2-carboxylate as an amorphous solid. $[\alpha]_D$=+56.0° (c=0.2, chloroform). IR (KBr): 3392w(br.), 3965w, 2950w, 1740m, 1709s, 1537m, 1459m, 1426m, 1394m, 1273m, 1218s, 1065m, 776w.

EXAMPLE 4.2.b

In analogy to Example 4.1.a, 100 mg (0.311 mmol) of methyl (R)-2-(tert.butoxycarbonylamino)-8-hydroxy-1,2,3,4-tetrahydro- naphthalene-2-carboxylate in 0.5 ml of pyridine were reacted with 25 mg of sodium hydride dispersion, 178 mg (0.86 mmol) of copper bromide-dimethyl sulphide complex and 273 mg (0.92 mmol) of benzyl 3-bromothiophene-2-carboxylate. After chromatography and drying in a high vacuum 88 mg (52.6%) of benzyl (R)-3-(7-tert.butoxycarbonylamino-7-methoxycarbonyl-5, 6,7,8-tetrahydro-naphthalene-1-yloxy)-thiophene-2-carboxylate were obtained as an amorphous solid. $[\alpha]_D$=−49.0° (c=0.2, chloroform). MS (FAB): 560.4 ($M^+$+$Na^+$, 40), 538.4 ($M^+$+$H^+$, 25), 438.4(100).

EXAMPLE 4.3.a

Analogously to Example 4.1.a, 520 mg (1.43 mmol) of tert.butyl (S)-2-(tert.butoxycarbonylamino)-8-hydroxy-1,2, 3,4-tetrahydro-naphthalene-2-carboxylate in 2 ml of pyridine were reacted with 75 mg of sodium hydride dispersion (55%), 413 mg (2.00 mmol) of copper bromide-dimethyl sulphide complex and 825 mg (2.86 mmol) of prop-2-enyl 2-iodobenzoate. After chromatography on 70 g of silica gel with ethyl acetate/hexane (1:4) and drying 645 mg (86.1%) of tert.butyl (S)-2-(tert.butoxycarbonylamino)-8-[2-(prop-2-enyloxycarbonyl)-phenoxy]-1,2,3,4-tetrahydro-naphthalene-2-carboxylate were obtained as amorphous solid. $[\alpha]_D$=+32.0° (c=0.1, chloroform). IR (KBr): 3390w (br.), 3080w, 2977m, 2932w, 1735s, 1716s, 1604m, 1510m, 1484m, 1455m, 1366m, 1299m, 1249s, 1081 m, 848m, 779m.

EXAMPLE 4.4.a

In analogy to Example 4.1.a, 383 mg (1.19 mmol) of methyl (S)-2-(tert.butoxycarbonylamino)-8-hydroxy-1,2,3,4-tetrahydro-naphthalene-2-carboxylate in 1 ml of pyridine were reacted at 110° for 1 hour with 94 mg (1.87 mmol) of sodium hydride dispersion (55%), 409 mg (1.99 mmol) of copper bromide-dimethyl sulphide complex and 1.17 g (3.48 mmol) of benzyl 2-bromo-5-nitrobenzoate, whereupon after chromatography on 200 g of silica gel with ethyl acetate/ hexane (1:4→3:7) and drying in a high vacuum 585 mg (85%) of methyl (S)-2-(tert.butoxycarbonylamino)-8-(2-benzyloxycarbonyl-4-nitro-phenoxy)-1,2,3,4-tetrahydro-naphthalene-2-carboxylate were obtained as an amorphous solid. M.p. 70°–80°. MS (ISP): 599.4 ($M^+$+$Na^+$, 25), 594.4 ($M^+$+$NH_4^+$, 30), 577.4 ($M^+$+$H^+$, 25), 474.4 (100[$\alpha]_D$=+ 52.7° (c=0.15, chloroform).

EXAMPLE 4.5.a

In analogy to Example 4.1.a, 280 mg (0.634 mmol) of trimethylsilylethyl (S)-2-benzyloxycarbonylamino-8-hydroxy-1,2,3,4-tetrahydro-naphthalene.-2-carboxylate were reacted in 1 ml of pyridine at 120° for 1.25 hours with 34 mg (0.66 mmol) of sodium hydride dispersion (55%), 208 mg (1.014 mmol) of copper bromidedimethyl sulphide complex and 474 mg (1.84 mmol) of tert.butyl 2-bromo-nicotinate, whereupon after working up and chromatography on 18 g of silica gel with ethyl acetate/hexane (1:4) and drying in a high vacuum 344 mg (88%) of tert.butyl (S)-3-(7-benzyloxycarbonylamino-7-trimethylsilylethoxycarbonyl-5,6,7,8-tetrahydro-naphthalen-1-yloxy)-nicotinate were obtained as an amorphous solid. $[\alpha]_D$=+56.0° (c=0.2, chloroform). MS (FAB): 619.3 ($M^+$+$H^+$, 60), 535.2 (10), 91.1 (100).

EXAMPLE 4.6.a

In analogy to Example 4.1.a, 720 mg (1.80 mmol) of benzyl (S)-(tert.butoxycarbonylamino)-8-hydroxy-1,2,3,4-tetrahydro-naphthalene-2-carboxylate were reacted in 2.5 ml of pyridine with 85 mg of sodium hydride dispersion, 520 mg (2.49 mmol) of copper bromide-dimethyl sulphide complex and 1.25 g (5.22 mmol) of prop-2-enyl 2-bromo-nicotinoate. After working up and chromatography on 500 g of silica gel with hexane/ethyl acetate (4:1) there were obtained after drying in a high vacuum 853 mg (84%) of prop-2-enyl (S)-2-(7-benzyloxycarbonyl-7-tert.butoxycarbonylamino-5,6,7,8-tetrahydro-naphthalen-1-yloxy)-nicotinate. MS: 558 ($M^+$, 1), 441 (15), 323 (27), 91 (100), 57 (80), 41 (52).

EXAMPLE 4.7.a

In analogy to Example 4.1.a, 270 mg (0.678 mmol) of methyl (S)-5-bromo-2-(tert.butoxycarbonylamino)-8- hydroxy-1,2,3,4-tetrahydro-naphthalene-2-carboxylate, 34.5 mg of sodium hydride dispersion (55%), 194 mg (0.943 mmol) of copper bromide-dimethyl sulphide complex and 553 mg (1.68 mmol) of benzyl 2-iodobenzoate in 1 ml of pyridine were heated to 120° for 4 hours. After working up analogously to Example 4.1.a. the crude product was chromatographed on 150 g of silica gel with hexane/ethyl acetate (9:1→1:1), whereupon after drying in a high vacuum 294.3 mg (71.6%) of methyl (S)-8-(2-benzyloxycarbonylphenoxy)-5-bromo-2-tert.butoxycarbonylamino-1,2,3,4-tetrahydro-naphthalene-2-carboxylate were obtained as a white amorphous solid. M.p. 66–74° (sintering). $[\alpha]_D$=+25.5° (c=0.2, chloroform). MS (ISP): 680.3 ($M^+ + Na^+$, 50), 675.4 ($M^+ + NH_4^+$, 65), 658.3 ($M^+ + H^+$, 45), 558.2 (100).

EXAMPLE 4.8.a

In analogy to Example 4.1.a, 2.5 g (7.78 mmol) of methyl (S)-2-(tert.butoxycarbonylamino)-8-hydroxy-1,2,3,4-tetrahydronaphthalene-2-carboxylate in 5 ml of pyridine were reacted at 130° for 2 hours with 370 mg of sodium hydride dispersion, 2.23 g (10.9 mmol) of copper bromide-dimethyl sulphide complex and 4.48 g (15.56 mmol) of prop-2-enyl 2-iodobenzoate. After chromatography on 500 g of silica gel with ethyl acetate/hexane (1:9→1:1) there were obtained 2.98 g (80%) of methyl (S)-2-(tert.butoxycarbonylamino)-8-[2-(prop-2-enyloxycarbonyl)phenoxy]-1,2,3,4-tetrahydronaphthalene-2-carboxylate as a viscous oil. $[\alpha]_D$=−57.0° (c=0.4, chloroform IR (film): 3386w(br.), 3075w, 2977m, 2950w, 1738s, 1717s, 1604m, 1581 m, 1 511 m, 1484m, 1455m, 1366m, 1247s(br.), 1166m, 777m.

EXAMPLE 5.1.a 6 ml of trifluoroacetic acid were added while cooling with ice and under argon to a solution of 591 mg (1.13 mmol) of tert.butyl (S)-2-(tert.butoxycarbonylamino)-8-[2-(prop-2-enyloxycarbonyl)-phenoxy]-1,2,3,4-tetrahydro-naphthalene-2-carboxylate in 6 ml of dichloromethane. The reaction mixture was stirred at 0° for 3 hours, whereupon the solvent was distilled off. The residue was dried in a high vacuum and dissolved in 4 ml of chloroform, whereafter 0.36 ml (2.82 mmol) of trimethylchlorosilane was added at 0°. The reaction mixture was stirred at room temperature for 15 minutes, treated with 0.62 ml (4.13 mmol) of ethyldiisopropylamine, stirred at 50° for 1 hour, cooled, treated with 419 mg (1.24 mmol) of fluoren-9-ylmethyl-succinimidyl carbonate, stirred at room temperature for 18 hours and at 50° for 40 hours, cooled and poured into a mixture of ethyl acetate and 1M $NaH_2PO_4$ solution. The organic phase was separated, washed with saturated sodium chloride solution, dried over $MgSO_4$ and concentrated, whereupon the residue was dried in a high vacuum and dissolved in 6 ml of ethyl acetate. The solution was treated with 228 mg (1.24 mmol) of pentafluorophenol, whereafter 0.192 ml (1.24 mmol) of N,N-diisopropylcarbodiimide was added while cooling with ice. The reaction mixture was stirred at room temperature overnight and then poured into a mixture of water and dichloromethane. The organic phase was separated, dried over $MgSO_4$ and concentrated. The residue was chromatographed on 300 g of silica gel with diethyl ether/hexane (1:4), whereupon after drying in a high vacuum 450 mg (46%) of pentafluorophenyl (S)-2-(fluoren-9-ylmethoxycarbonyl)-8-[2-(prop-2-enyloxycarbonyl)-phenoxy]-1,2,3,4-tetrahydro-naphthalene-2-carboxylate were obtained as an amorphous solid.

$[\alpha]_D$=−16.0° (c=0.1, chloroform). IR (KBr): 3371w(br.), 3075w, 2949w, 1788m, 1716s, 1521 s, 1541 m, 1268m, 1242s, 1165w, 1135w, 1078m, 1047m, 1000s, 740w.

EXAMPLE 6.1.a

A mixture of 80 mg (0.13 mmol) of methyl (S)-8-(2-benzyloxycarbonyl-phenoxy)-5-bromo-2-(tert.butoxycarbonylamino)-1,2,3,4-tetrahydro-naphthalene-2-carboxylate, 43 mg (0.143 mmol) of 3,4-dimethoxyphenyl-trimethylstannane and 6.9 mg (6 µmol) of tetrakis-(triphenylphosphine)-palladium in 0.4 ml of dioxan was stirred at 80° for 18 hours, cooled, treated with a further 8.6 mg (30 µmol) of 3,4-dimethoxyphenyl-trimethylstannane and once more stirred at 80° for 4 hours, again cooled and filtered over Celite. The filter residue was washed with dioxan and the filtrate was concentrated, whereupon the residue was taken up in ethyl acetate. The solution obtained was washed with saturated sodium chloride solution, dried over magnesium sulphate and concentrated. The residue was chromatographed on 50 g of silica gel with hexane/ethyl acetate (9:1→1:1), whereupon after drying in a high vacuum 34.0 mg (39.2%) of methyl (S)-8-(2-benzyloxycarbonyl-phenoxy)-5-(3,4-dimethoxyphenyl)-2-(tert.butoxycarbonylamino)-1,2,3,4-tetrahydro-naphthalene-2-carboxylate were obtained as a beige powder. M.p. 64°–74° (sintering). $[\alpha]_D$=−13.0° (c=0.2, chloroform). MS (FAB): 668.4 ($M^+ + H^+$, 5), 568.3 (40), 217.0 (55), 109.1 (35), 91.2 (100).

EXAMPLE 6.2.a

A mixture of 90.0 mg (0.147 mmol) of methyl (S)-8-(2-benzyloxycarbonyl-phenoxy)-5-bromo-2-(tert.butoxycarbonylamino)-1,2,3,4-tetrahydro-naphthalene-2-carboxylate, 19.2 mg (0.295 mmol) of potassium cyanide, 6.5 mg (11.8 µmol) of 1,1'-bis-(diphenylphosphino)-ferrocene and 3,0 mg (2.9 µmol) of bis-(dibenzylideneacetone)-di-palladium ($Pd_2dba_3$) in 0.2 ml of N,N-dimethylacetamide was stirred at 800 under argon for 15 hours, cooled and filtered over Celite, whereupon the filtrate was evaporated. The residue was chromatographed on 30 g of silica gel with hexane/ethyl acetate (9:1→1:1), whereby firstly 71 mg (78.9%) of starting material were recovered; subsequently there were obtained about 7.0 mg (8.6%) of crude methyl (S)-8-(2-benzyloxycarbonyl-phenoxy)-2-(tert.butoxycarbonylamino)-5-cyano-1,2,3,4-tetrahydro-naphthalene-2-carboxylate which was purified by means of preparative HPLC chromatography (column: Vydac 250-10 RP-18; programme: 60% acetonitrile→100% acetonitrile in 20 minutes). 5.5 mg (6.7% based on starting material used; 31.6% based on reacted starting product) of pure product were obtained. MS: 556 ($M^+$, <1), 439 (10), 397 (20), 91 (100), 57 (24).

EXAMPLE 7.1.1.a 2 ml of trifluoroacetic acid were added dropwise under argon and while cooling with ice to a solution of 540 mg (1.02 mmol) of methyl (S)-8-(2-benzyloxycarbonyl-phenoxy)-2-tert.butoxycarbonylamino-1,2,3,4-tetrahydro-naphthalene-2-carboxylate in 2 ml of dichloromethane. The reaction mixture was stirred at 0° for 1.5 hours, whereupon the solvent was distilled off in a high vacuum. The residue was dried well and treated with 290 mg (1.53 mmol) of L-Boc-alanine, 293 mg (1.53 mmol) of N-ethyl-N'-(3-dimethylaminopropyl)-carbodiimide hydrochloride and 310 mg (2.30 mmol) of 1-hydroxybenzotriazole. The mixture was dissolved in 3 ml of DMF and the solution was treated with 0.52 ml (3.06 mmol) of ethyldiisopropylamine while cooling with ice and under argon, stirred at 0° for 30 minutes and at room temperature for 18 hours and then poured into a mixture of ice-water and ethyl acetate. The organic phase was separated, washed with water, saturated sodium hydrogen carbonate solution and sodium chloride solution, dried over $MgSO_4$ and evaporated. The residue was chromatographed on 60 g of silica gel with ethyl acetate/hexane (2:3), whereupon 570 mg (92.7%) of methyl (S)-8-(2-benzyloxycarbonyl-phenoxy)-2-[N-(tert.butoxycarbonyl-L-alanyl)]-1,2,3,4-tetrahydro-naphthalene-2-carboxylate were obtained as an amorphous solid. $[\alpha]_D$=+24.0° (c=0.1, chloroform). MS (FAB): 603 ($M^+$+H+, 25), 503 (100), 432 (20), 414 (40), 372 (20), 324 (40), 264 (50), 247 (40).

EXAMPLE 7.1.1.b

In analogy to Example 7.1.1.a, from 500 mg (0.94 mmol) of methyl (R)-8-(2-benzyloxycarbonyl-phenoxy)-2-tert.butoxycarbonyl-amino-1,2,3,4-tetrahydro-naphthalene-2-carboxylate there were obtained 450 mg (79.4%) of methyl (R)-8-(2-benzyloxycarbonylphenoxy)- 2-[N-(tert.butoxycarbonyl-D-alanyl)]-1,2,3,4-tetrahydronaphthalene-2-carboxylate as an amorphous solid. $[\alpha]_D$=−23.5 (c=0.2, chloroform). MS (FAB): 603 ($M^+$+$H^+$, 25), 503 (100).

EXAMPLE 7.1.2.a 2 ml of trifluoroacetic acid were added under argon and while cooling with ice to a solution of 550 mg (0.913 mmol) of methyl (S)-8-(2-benzyloxycarbonyl-phenoxy)-2-[N-(tert.butoxycarbonylamino-L-alanyl)]-1,2,3,4-tetrahydro-naphthalene-2-carboxylate in 2 ml of dichloromethane. The reaction mixture was stirred at 0° for 1 hour, whereupon the solvent was removed in a high vacuum. The residue was dried, treated with 260 mg (1.37 mmol) of Boc-L-alanine, 263 mg (1.37 mmol) of N-ethyl-N'-(3-dimethylaminopropyl)carbodiimide hydrochloride and 370 mg of 1-hydroxybenzotriazole, whereupon the mixture was dissolved in 3 ml of N,N-dimethylformamide and the solution was treated at 0° with 0.47 ml (2.74 mmol) of N-ethyldiisopropylamine. The reaction mixture was stirred at 0° for 30 minutes and at room temperature for 1 hour and then poured into a mixture of ice-water and ethyl acetate. The organic phase was separated, washed with water, saturated sodium hydrogen carbonate solution and sodium chloride solution, dried over $MgSO_4$ and concentrated. The residue was chromatographed on 50 g of silica gel with ethyl acetate/hexane (3:2), whereupon after drying in a high vacuum 550 mg (89.4%) of methyl (S)-8-(2-benzyloxycarbonyl-phenoxy)-2-[N-(tert.butoxycarbonyl.-L-alanyl)-L-alanyl]-1,2,3,4-tetrahydronaphthalene-2-carboxylate were obtained as an amorphous solid. $[\alpha c]_D$=+8.0° (c=0.1, chloroform). MS (ISP): 696.2 ($M^+$+$Na^+$, 50), 674.2 ($M^+$+$H^+$, 100), 618 (30), 574.1 (65), 432.1 (75).

EXAMPLE 7.1.2.b

In analogy to Example 7.1.2.a, 400 mg (0.66 mmol) of methyl (R)-8-(2-benzyloxycarbonyl-phenoxy)-2-[N-(tert.butoxycarbonyl-D-alanyl)]-1,2,3,4-tetrahydro-naphthalene-2-carboxylate were reacted with Boc-D-alanine. After chromatography on 50 g of silica gel with ethyl acetate/hexane (1:1) 390 mg (87.6%) of methyl (R)-8-(2-benzyloxycarbonyl-phenoxy)-2-[N-[(tert.butoxycarbonylamino-D-alanyl)-D-alanyl]]-1,2,3,4-tetrahydro-naphthalene-2-carboxylate were obtained as an amorphous solid. $[\alpha]_D$=−10.0° (c=0.2, chloroform). MS (FAB): 674 ($M^+$+H, 20), 574 (20), 422 (100), 414 (30), 372 (50), 342 (50), 324 (50), 282 (50), 264 (50), 247 (40).

EXAMPLE 7.1.3.a

A solution of 505 mg solution of 505 mg (0.75 mmol) of methyl (S)-8-(2-benzyloxycarbonyl-phenoxy)-2-[N-[(tert.butoxycarbonyl-L-alanyl)-L-alanyl]]-1,2,3,4-tetrahydro-naphthalene-2-carboxylate in 2 ml of trifluoroethanol was added at room temperature to a pre-hydrogenated suspension of 150 mg of palladium/charcoal (10%) in 10 ml of trifluoroethanol. The mixture was hydrogenated at atmospheric pressure for 4 hours and filtered over Celite, whereupon the solvent was distilled off. The residue was dried in a high vacuum and dissolved in dichloromethane, whereupon the solution was treated with 207 mg (1.12 mmol) of pentafluorophenol. 216 mg (1.12 mmol) of N-ethyl-N'-(3-dimethylaminopropyl)-carbodiimide hydrochloride were added portionwise to the reaction mixture while cooling with ice and under argon, whereupon the mixture was stirred at 0° for 30 minutes and at room temperature for 6 hours. The reaction mixture was poured into a mixture of ice-water, 0.1N hydrochloric acid solution and ethyl acetate. The organic phase was separated, washed with saturated sodium chloride solution, dried over $MgSO_4$ and evaporated. The residue was dried in a high vacuum and dissolved in 1.5 ml of dichloromethane, whereupon the solution was treated with 1.5 ml of trifluoroacetic acid under argon and while cooling with ice, stirred at 0° for 1.5 hours and then evaporated in a high vacuum. The residue was dried and suspended in diethyl ether/hexane (1:3), whereupon the suspension was stirred for 1 hour and filtered. The residue was washed with hexane, whereupon after drying in a high vacuum 580 mg (100%) of methyl (S)-2-[N-(L-alanyl-L-alanyl)]-1,2,3,4-tetrahydro-8-[2-(pentafluorophenoxycarbonyl)phenoxy]-naphthalene-2-carboxylate trifluoroacetate were obtained as an amorphous solid. MS (ISP): 672 ($M^+$+$Na^+$, 25), 650 ($M^+$+$H^+$, 100), 507.8 (90), 448 (30), 406 (25).

EXAMPLE 7.1.3.b

In analogy to Example 7.1.3.a, from 120 mg (0.206 mmol) of methyl (R)-8-[2-(benzyloxycarbonyl-phenoxy)]-2-[N-[(tert.butoxycarbonyl-D-alanyl)-D-alanyl]]-1,2,3,4-tetrahydro-2-naphthalenecarboxylate there are obtained 155 mg (98.5%) of methyl (R)-2-[N-(D-alanyl-D-alanyl)]-1,2,3,4-tetrahydro-8-[2-(pentafluorophenoxycarbonyl)phenoxy]-2-naphthalene carboxylate trifluoroacetate. MS (FAB): 650 ($M^+$+H, 100), 508 (30), 448 (20), 324 (20), 307 (60), 264 (50), 247 (50), 160 (40), 143 (40), 115 (70).

EXAMPLE 7.1.4.a

A solution of 573 mg (0.75 mmol) of methyl (S)-2-[N-(L-alanyl-L-alanyl)]-1,2,3,4-tetrahydro-8-[2-(pentafluorophenoxycarbonyl)phenoxy]-2-naphthalenecarboxylate trifluoroacetate in 20 ml of dioxan was added dropwise at 80° and under argon within 17 hours to a mixture of 1 l of dioxan and 10 ml of pyridine. The reaction mixture was stirred at 80° for a further 3 hours and then cooled, whereupon the solvent was removed. The residue was taken up in chloroform and 0.5N hydrochloric acid, whereupon the organic phase was separated, dried over $MgSO_4$ and concentrated. The residue was chromatographed on 30 g of silica gel with chloroform/methanol (6:1), whereupon 285 mg (81.6%) of methyl (12S,15S,18S)-12,15-dimethyl-10,13,16-trioxo-10,11,12,13,14,15,16,17,18,19,20,21-dodecahydro-1,18-etheno-dibenz[b,n][1,5,8,11]oxatriazacyclopentadecene-18-carboxylate were obtained as an amorphous solid (sic).

$[\alpha]_D$=−9.0° (c=0.1, chloroform). MS (FAB): 466 ($M^+$+$H^+$, 100), 406 (30), 264 (45), 247 (50), 232 (40), 214 (40), 197 (30), 181 (35), 126 (55), 121 (40), 105 (40).

EXAMPLE 7.1.4.b

In analogy to Example 7.1.4.a, from 160 mg (0.21 mmol) of methyl (R)-2-[N-(D-alanyl-D-alanyl)]-1,2,3,4- tetrahydro-8-[-2-(pentafluorophenoxycarbonyl)-phenoxy]-2-naphthalenecarboxylate trifluoroacetate there were obtained 76.5 mg (78.2%) of methyl (12R,15R,18R)-12,15-dimethyl-10,1 3,16-trioxo-10,11,12,13,14, 15,16,17,18,19, 20,21-dodecahydro-1,18-etheno-dibenz[b,n]-oxatriazacyclopentadecene-18-carboxylate as an amorphous solid. $[\alpha]_D=+9.0°$ (c=0.1, chloroform). MS (FAB): 466 (M$^+$+H$^+$, 100).

EXAMPLE 7.1.5.a 300 mg of lithium hydroxide monohydrate were added while cooling with ice to a solution of 340 mg (0.75 mmol) of methyl (12S,15S,18S)-12,15-dimethyl-10,13,16-trioxo-10,11,1 2,13,14,15, 16,17,18,19,20,21-dodecahydro-1,18-etheno-dibenz[b,n][1,5, 8,11]oxatriazacyclopentadecene-18-carboxylate in a mixture of 3 ml of tetrahydrofuran, 1 ml of methanol and 1 ml of water. The reaction mixture was stirred at 0° for 30 minutes and at room temperature for 1.5 hours and then poured into a mixture of water and chloroform/methanol (4:1). The aqueous phase was separated and exhaustively extracted with chloroform/methanol (4:1). The combined organic phases were dried over MgSO$_4$ and concentrated. The residue was crystallized from diethyl ether/hexane (1:1), whereupon after drying in a high vacuum 270 mg (79.7%) of (12S, 15S,18S)-12,15-dimethyl-10,13, 16-trioxo-10,11,12,13,14,15,16,17,18,19,20,21-dodecahydro-1,18-etheno-dibenz[b,n]oxatriazacyclopentadecene-18-carboxylic acid were obtained. $[\alpha]_D=-13.5°$ (c=0.1, methanol). MS (FAB): 451 (M+., 30), 450 (M$^+$-H, 100).

EXAMPLE 7.1.5.b

In analogy to Example 7.1.5.a, from 520 mg (1.12 mmol) of methyl (12R,15R,18R)-12,15-dimethyl-10,13,16-trioxo-10,11, 12,13,14,15,16,17,18,19,20,21-dodecahydro-1,18-etheno-dibenz[b,n]oxatriazacyclopentadecene-18-carboxylate there were obtained 435 mg (85%) of (12R, 15R,18R)-12,15-dimethyl-10,13,16-trioxo-10,11,12,13,14, 15,16,17,18,19,20,21-dodecahydro-1,18-etheno-dibenz[b,n] oxatriazacyclopentadecene-18-carboxylic acid. $[\alpha]_D=+14.0°$ (c=0.1, methanol). MS (FAB): 451 (M$^+$·, 30), 450 (M$^+$-H, 100).

EXAMPLE 7.2.1.a

A solution of 355 mg (0.66 mmol) of benzyl 3-[(S)-7-(tert.butoxy-carbonylamino)-7-methoxycarbonyl-5,6,7,8-tetrahydro-naphthalen-1-yloxy]-thiophene-2-carboxylate in 1 ml of dichloromethane was reacted at 0° with 1 ml of trifluoroacetic acid analogously to Example 7.1.1.a, whereupon the product was reacted with 187 mg (0.99 mmol) of Boc-L-alanine, 189 mg (0.99 mmol) of N-ethyl-N'-(3-dimethylaminopropyl)-carbodiimide hydrochloride, 225 mg (1.45 mmol) of 1-hydroxybenzotriazole and 339 μl (1.98 mmol) of ethyldiisopropylamine in 3.5 ml of N,N-dimethylformamide. After chromatography on 110 g of silica gel with ethyl acetate/hexane (3:7→4.6) there were obtained after drying in a high vacuum 336 mg (83.8%) of benzyl 3-[(S)-7-[N-(tert.-butoxycarbonyl-L-alanyl)]-7-methoxycarbonyl-5,6,7,8-tetrahydro-naphthalen-1-yloxy]-thiophene-2-carboxylate as an amorphous solid. $[\alpha]_D=+19.0°$ (c=0.2, chloroform). MS (FAB): 609 (M$^+$+H$^+$, 70), 509.1 (90), 217.1 (100), 109 (40), 91.0 (95).

EXAMPLE 7.2.2.a

A solution of 300 mg (0.493 mmol) of benzyl 3-[(S)-7-[N-(tert.butoxycarbonyl-L-alanyl)]-7-methoxycarbonyl-5,6, 7,8-tetrahydro-naphthalen-1-yloxy]-thiophene-2-carboxylate in 1 ml of dichloromethane was reacted at 0° with 1 ml of trifluoroacetic acid in analogy to Example 7.1.2.a, whereupon the product was reacted with 123 mg (0.65 mmol) of Boc-L-alanine, 124.6 mg (0.65 mmol) of N-ethyl-N'-(3-dimethylaminopropyl)-carbodiimide hydrochloride, 148 mg (0.955 mmol) of 1-hydroxybenzotriazole and 222 μl (1.302 mmol) of N-ethyldiisopropylamine in 3 ml of N,N-dimethylformamide. After chromatography on 110 g of silica gel with chloroform/methanol (98:2) and drying in a high vacuum 300 mg (92%) of benzyl 3-[(S)-7-[N-[(tert.-butoxycarbonyl-L-alanyl)-L-alanyl]]-7-methoxycarbonyl-5, 6,7,8-tetrahydronaphthalen-1-yloxy]-thiophene-2-carboxylate were obtained as an amorphous solid. $[\alpha]_D=+8.0°$ (c=0.2, chloroform). MS(FAB): 680.5 (M$^+$+H$^+$, 60), 580.4 (50), 420.3 (20), 378.1 (30), 348.1 (30), 330.1 (20), 270.0 (20), 217 (30), 91 (100).

EXAMPLE 7.2.3.a

In analogy to Example 7.1.3.a, 284 mg of benzyl 3-[(S)-7-[N-[(tert.-butoxycarbonyl-L-alanyl)-L-alanyl]]-7-methoxycarbonyl-5,6,7,8-tetrahydro-naphthalen-1-yloxy]-thiophene-2-carboxylate in 5 ml of methanol/water (9:1) were hydrogenated with 100 mg of palladium/charcoal (10%) for 48 hours at 2 bar. The product was firstly reacted with 79.2 mg (0.43 mmol) of pentafluorophenol and 82.4 mg (0.43 mmol) of N-ethyl-N'-(3-dimethylaminopropyl) carbodiimide hydrochloride in 2 ml of methylene chloride and the product, after drying in a high vacuum, was treated in analogy to Example 7.1.3.a with 2 ml of methylene chloride and 2 ml of trifluoroacetic acid, whereupon after precipitation with diethyl ether/hexane and drying in a high vacuum 240 mg (72.5%) of pentafluorophenyl 3-[(S)-7-[N-(L-alanyl-L-alanyl)]-7-methoxycarbonyl-5,6,7,8-tetrahydro-naphthalen-1-yloxy]-thiophene-2-carboxylate trifluoroacetate were obtained as an amorphous solid. MS (ISP): 678.3 (M$^+$· (free base) +Na$^+$, 50), 656.4 (M$^+$· (free base) +H$^+$, 70), 514.3 (100), 454.3 (35), 412.4 (25).

EXAMPLE 7.2.4.a

In analogy to Example 7.1.4.a, 120 mg (0.156 mmol) of pentafluorophenyl 3-[(S)-7-[N-(L-alanyl-L-alanyl)]-7-methoxycarbonyl-5,6,7,8-tetrahydro-naphthalen-1-yloxy]-thiophene-2-carboxylate trifluoroacetate in 10 ml of dioxan were added dropwise at 800 within 18 hours to a mixture of 120 ml of dioxan and 2 ml of pyridine. After chromatography of the product on 12 g of silica gel with chloroform/methanol (95:5) and drying in a high vacuum 50 mg (68%) of methyl (11S,14S,17S)-11,14-dimethyl-9,12,15-trioxo-9, 10,11,12,13,14,15,16,17,18,19,20-dodecahydro-1,17-etheno-thieno[3,2-b]benz[n][1,5,8,11]oxatriazacyclopentadecene-17-carboxylate were obtained as an amorphous solid. $[\alpha]_D=-57.30$ (c=0.15, chloroform). MS (ISP) 492.2 (M$^+$+Na$^+$, 25) 472.3 (M$^+$+H$^+$, 75), 412.6 (100).

EXAMPLE 7.2.5.a

In analogy to Example 7.1.5.a, 35 mg (76.5 μmol) of methyl (11S, 14S, 17S)-11,14-dimethyl-9,12,15-trioxo-9,10, 11,12,13,14,15,16,17,18-,19, 19,20-dodecahydro-1,17-etheno-thieno[3,2-b]benz-[n][1,5,8,1 11oxa-triazacyclopentadecene-17-carboxylate in 1.5 ml of tetrahydrofuran/methanol/water (3:1:1) were reacted with 34 mg of lithium hydroxide monohydrate, whereupon after precipitation from diethyl ether/hexane (1:1) and drying in a high vacuum 29.6 mg (87%) of (11S,14S,17S)-11,14-dimethyl-9,12, 15-trioxo-9,10,11,12,13,14,15,16,17,18,19,20-dodecahydro-1,17-etheno-thieno[3,2-b]benz[n][1,5,8,11]oxatriazacyclopentadecene-17-carboxylic acid were obtained as an amorphous solid. MS (FAB): 457.4 (M+., 20), 456.4 (M$^+$-H, 100). IR (KBr): 3380s(br), 3107w, 3087w, 2977w, 2928w, 1724m, 1643s, 1583w, 1536s, 1460m, 1420w, 1388m, 1236m, 1120w, 1019w, 775w.

EXAMPLE 7.3.1.a

A solution of 540 mg of methyl (S)-tert.-butoxycarbonylamino-8-(2-benzyloxycarbonyl-4-nitrophenoxy)-1,2,3,4-tetrahydronaphthalene-2-carboxylate in 2 ml of dichloromethane was reacted at 0° with 2 ml of trifluoroacetic acid analogously to Example 7.1.1.a and the product obtained was reacted with 266 mg (1.41 mmol) of Boc-L-alanine, 270 mg (1.41 mmol) of N-ethyl-N'-(3-dimethylaminopropyl)carbodiimide hydrochloride, 279 mg (2.1 mmol) of 1-hydroxybenzotriazole and 482 ml (2.82 mmol) of ethyldiisopropylamine in 5 ml of N,N-dimethylformamide. After chromatography on 80 g of silica gel with hexane/ethyl acetate (1:1→2:3) 468 mg (77%) of methyl (S)-8-(2-benzyloxycarbonyl-4-nitrophenoxy)-2-[N-(tert.-butoxycarbonyl-L-alanyl)]-1,2,3,4-tetrahydro-naphthalene-2-carboxylate were obtained as an amorphous foam. MS (FAB): 648.1 (M$^+$+H$^+$, 40), 548.1 (50), 217 (80), 109 (40), 91(100).

EXAMPLE 7.3.2.a

A solution of 575 mg (0.88 mmol) of methyl (S)-8-(2-benzyloxycarbonyl-4-nitrophenoxy)-2-[N-(tert.-butoxycarbonyl-L-alanyl)]-1,2,3,4-tetrahydro-naphthalene-2-carboxylate in 1 ml of dichloromethane was reacted at 0° with 1.5 ml of trifluoroacetic acid analogously to Example 7.1.1.a and the product was reacted with 287 mg (1.33 mmol) of Boc-L-proline, 255 mg (1.33 mmol) of N-ethyl-N'-(3-dimethylaminopropyl)-carbodiimide hydrochloride, 270 mg (1.99 mmol) of 1-hydroxybenzotriazole and 455 µl (2.66 mmol)of ethyldiisopropylamine in 8 ml of N,N-dimethylformamide. After chromatography on 100 g of silica gel with chloroform 572 mg (86.5%) of methyl (S)-8-(2-benzyloxycarbonyl-4-nitrophenoxy)-2-[N-[(tert.-butoxycarbonyl-L-prolyl)-L-alanyl]]-1,2,3,4,-tetrahydronaphthalene-2-carboxylate were obtained as an amorphous foam. MS (ISP): 745.5 (M$^+$+H+, 70), 689.4 (20), 645.4 (100), 477.4 (85).

EXAMPLE 7.3.3.a a) A suspension of 540 mg (0.78 mmol) of methyl (S)-8-(2-benzyloxycarbonyl-4-nitrophenoxy)-2-[N-(tert.-butoxycarbonyl-L-prolyl)-L-alanyl]-1,2,3,4-tetrahydro-naphthalene-2-carboxylate and 200 mg of palladium-charcoal (10%) in 18 ml of ethanol was hydrogenated at room temperature for 2 hours under atmospheric pressure and then filtered over Celite. The filter residue was washed with ethanol and the filtrate was evaporated. After drying the residue in a high vacuum 440 mg (97%) of methyl (S)-8-(4-amino-2-carboxyphenoxy)-2-[N-[(tert.-butoxycarbonyl-L-prolyl)-L-alanyl]]-1,2,3,4-tetrahydronaphthalene-2-carboxylate were obtained as an amorphous solid, m.p.>135°. [α]$_D$=−13.0° (MeOH, c=0.1). MS (ISP): 625.3 (M$^+$+H$^+$, 10), 525,5 (100 ).

b) 308 µl (3.26 mmol) of acetic anhydride were added at room temperature to a solution of 340 mg (0.544 mmol) of the above product in 3 ml of pyridine. The mixture was stirred for 2 hours and then concentrated. The residue was taken up in methylene chloride, the solution was washed twice with H$_2$O the aqueous phases were extracted with methylene chloride and the combined organic phases were dried over MgSO$_4$ and concentrated. The residue was dried in a high vacuum. After crystallization from diethyl ether/hexane (2:1), washing and drying in a high vacuum 320 mg (88%) of methyl (S)-8-(4-acetylamino-2-carboxyphenoxy)-2-[N-[(tert.-butoxycarbonyl-L-prolyl)-L-alanyl]-1,2,3,4-tetrahydro-naphthalene-2-carboxylate were obtained as an amorphous product [α]$_D$=−55.0° (CHCl3, c=0.2). MS (ISP): 689.6 (M$^+$+Na$^+$, 50), 684.6 (M$^+$+NH$_4^+$, 60), 667.5 (M$^+$+H$^+$, 50), 567.2 (100).

c) 138 mg (0.72 mmol) of N-ethyl-N'-(3-dimethylaminopropyl)carbodiimide hydrochloride were added portionwise at 0° to a solution of 323 mg (0.48 mmol) of the above product and 133 mg (0.72 mmol) of pentafluorophenol in 4 ml of dichloromethane, whereupon the mixture was stirred at 0° for 2 hours and then added to phosphate buffer (pH 6.8). The aqueous phase was extracted with dichloromethane and the combined organic phases were extracted with saturated sodium chloride solution, dried over MgSO$_4$ and concentrated. The residue was dried in a high vacuum and then dissolved in 2 ml of dichloromethane, whereupon 1.5 ml of trifluoroacetic acid were added at 0°. The mixture was stirred at 0° for 2.5 hours and then concentrated. The residue was dried in a high vacuum and suspended in diethyl ether, filtered off, washed with diethyl ether and dried in a high vacuum, whereupon 327 mg (80%) of methyl (S)-8-(4-acetylamino-2-pentafluorophenoxycarbonylphenoxy)-2-[N-(L-prolyl-L-alanyl)]-1,2,3,4-tetrahydro-naphthalene-2-carboxylate trifluoroacetate were obtained. M.p. 136°–146° (sintering). [α]$_D$=−23.0° (CHCl$_3$, c=0.2). MS (ISP): 733.4 (M$^+$+H$^+$, 100).

EXAMPLE 7.3.4.a

A solution of 227 mg (0.268 mmol) of methyl (S)-8-(4-acetylamino-2-pentafluorophenoxycarbonylphenoxy)-2-[N-(L-prolyl-L-alanyl)]-1,2,3,4-tetrahydro-naphthalene-2-carboxylate trifluoroacetate in 20 ml of dioxan was added dropwise at 80° within 18 hours under argon to a mixture of 300 ml of dioxan and 4.5 ml of pyridine. The reaction mixture was stirred at 80° for 2 hours, cooled, concentrated and poured into a mixture of 0.1N HCl solution and dichloromethane. The organic phase was separated, dried over magnesium sulphate and concentrated. The residue was pre-purified on 100 g of silica gel with chloroform/methanol (98:2→9:1), whereupon after purification by means of preparative HPLC (column: Vydac C$_{18}$ 100 250–10; programme: 25% acetonitrile→60% acetonitrile), lyophilization and drying 102.4 mg (70%) of methyl (14aS,17S,20S)-8-acetylamino-17-methyl-10,15,18-trioxo-11,12,13,14,14a,15,16,17,18,19,20,21,22,23-tetradecahydro-1,20-etheno-10 H-pyrrolo[1,2-e]dibenz]b,n][1,5,8,11]oxatriazacyclopentadecene-20-carboxylate were obtained as a light yellowish amorphous solid. M.p. 180°–200° (sintering). [α]$_D$=−11.6° (CHCl$_3$, c=0.06). MS (ISP): 571.5 (M$^+$+Na$^+$, 30), 566.6 (M$^+$+NH$_4^+$100), 549.6 (M$^+$+H$^+$, 95). 13.0 mg (4.4%) of dimeric product cyclo[L-alanyl-[(S)-2-(7-amino-7-methoxycarbonyl-5,6,7,8-tetrahydronaphthalen-1-yloxy)-benzoyl]-L-prolyl-L-alanyl]-[(S)-2-(7-amino-7-methoxycarbonyl-5,6,7,8-tetrahydro-naphthalen-1-yloxy)-benzoyl]-L-prolyl-];

m.p. (dec.) >280° were also obtained.

EXAMPLE 7.3.5.a 16 mg of lithium hydroxide monohydrate were added while cooling with ice to a solution of 20 mg (0.036 mmol)

of methyl (14aS, 17S,20S)-8-acetylamino-17-methyl-10,15, 18-trioxo-11,12,13,14a,15,16,17,18,19,20,21,22,23-tetradecahydro-1,20-etheno-10H-pyrrolo[1,2-e]dibenz[b,n] [1,5,8,11]-oxatriazacyclopentadecene-20-carboxylate in 1 ml of tetrahydrofuran/methanol/water (3:1:1). The reaction mixture was stirred at room temperature for 2 hours and then poured into a mixture of ice, 0.5N HCl and chloroform. The aqueous phase was separated and extracted with chloroform. The combined organic phases were dried over sodium sulphate and evaporated. The residue was suspended in diethyl ether/hexane (1:1), filtered off and dried in a high vacuum, whereupon 18 mg (92%) of (14aS,17S,20S)-8-acetylamino-17-methyl-10,15,18-trioxo-11,12,13,14,14a, 15,16,17,18,19,20,21,22,23-tetradecahydro-1,20-etheno-10H-pyrrolo[1,2-e]dibenz[b,n][1,5,8,11]oxatriazacyclopentadecene-20-carboxylic acid were obtained as a white powder. M.p. 70°–110° (sintering). $[\alpha]_D$=−32.0° (methanol, c=0.15). MS (ISP): 533.2 ($M^+$+$H^+$, 100).

EXAMPLE 7.4.1.1.a

In analogy to Example 7.1.1.a, 816 mg of prop-2-enyl (S)-2-(7-benzyloxycarbonyl-7-tert.-butoxycarbonylamino-5,6,7,8-tetrahydronaphthalen-1-yloxy)-nicotinate were treated firstly at 0° with 1.5 ml of trifluoroacetic acid and 2 ml of dichloromethane. The product was subsequently reacted with 414 mg (2.19 mmol) of Boc-L-alanine, 444 mg (3.28 mmol) of 1-hydroxybenzotriazole, 428 mg (2.19 mmol) of N-ethyl-N'-(3-dimethylaminopropyl)-carbodiimide hydrochloride and 750 µl (4.38 mmol) of ethyldiisopropylamine in 7 ml of N,N-dimethylformamide. After working up according to Example 7.1.1.a and chromatography on 130 g of silica gel with hexane/ethyl acetate (1:1) and drying in a high vacuum 792 mg (86%) of prop-2-enyl 2-[(S)-7-benzyloxycarbonyl-7-[N-[(tert.-butoxycarbonyl-L-alanyl)]-5,6,7,8-tetrahydro-naphthalen-1-yloxy]-nicotinate were obtained as an amorphous solid. M.p. 55°–68°. $[\alpha]_D$+23.0° (chloroform, c=0.2). MS (ISP): 647.6 ($M^+$+$NH_4^+$, 29), 630.6 ($M^+$+$H^+$, 100).

EXAMPLE 7.4.1.2.a

In analogy to Example 7.1.1.a, 321 mg (0.51 mmol) of prop-2-enyl 2-[(S)-7-benzyloxycarbonyl-7-[N-[(tert.-butoxycarbonyl-L-alanyl)]-5,6,7,8-tetrahydro-naphthalen-1-yloxy]-nicotinate in 1.5 ml of dichloroethane were treated at 0° with 1.0 ml of trifluoroacetic acid. The product was dried in a high vacuum and reacted with 340 mg (0.77 mmol) of Boc-Glu(OMe)OH, 155 mg (1.15 mmol) of 1-hydroxybenzotriazole, 147 mg (0.77 mmol) of N-ethyl-N'-(3-dimethylaminopropyl)-carbodiimide hydrochloride and 290 µl (1.69 mmol) of ethyl-diisopropylamine in 4 ml of N,N-dimethylformamide. After chromatography on 120 g of silica gel with hexane/ethyl acetate (1:1→2:3) and after drying in a high vacuum 293 mg (99%) of prop-2-enyl 2-[(S)-7-benzyloxycarbonyl-7-[N-[(tert.-butoxycarbonyl-L-$O^6$-methylglutamyl)-L-alanyl]]-5,6,7,8-tetrahydronaphthalen-1-yloxy]-nicotinate were obtained. M.p. 55°–75° $[\alpha]_D$=+24° (chloroform, c=0.2). MS (ISP): 795.5 ($M^+$+$Na^+$, 25), 793.6 ($M^{++}$+$H^+$, 100).

EXAMPLE 7.4.1.3.a

Sufficient N-methylaniline was added to 5 ml of a mixture of dimethyl sulphoxide, tetrahydrofuran and 0.5N hydrochloric acid (2:2:1) until the pH of the solution had reached 7. The solution was flushed with nitrogen for 15 minutes, then treated with 287 mg (0.37 mmol) of prop-2-enyl 2-[(S)-7-benzyloxycarbonyl-7-[N-[(tert.-butoxycarbonyl-L-$O^6$-methylglutamyl)-L-alanyl]]-5,6,7,8-tetrahydronaphthalen-1-yloxy]-nicotinate and 74.5 mg (0.065 mmol) of tetrakis(triphenylphosphine)palladium and stirred for 24 hours. After concentration the residue was poured into a mixture of dichloromethane, ice and water, whereafter the pH was adjusted to 3 with 1N HCl solution. The aqueous phase was separated and extracted twice with dichloromethane. The combined Organic phases were dried over magnesium sulphate and concentrated. The residue was chromatographed on 50 g of silica gel with chloroform/methanol (95:5→4:1), whereupon after precipitation of the residue from diethyl ether/hexane, filtration and drying 229 mg (84%) of 2-[(S)-7- benzyloxycarbonyl-7-[N-[(tert-butoxycarbonyl-L-$O^6$-methylglutamyl)-L-alanyl]]-5,6,7,8-tetrahydro-naphthalen-1-yloxy]-nicotinic acid were obtained. M.p. (dec.) >145°. $[\alpha]_D$=+17.0° (chloroform, c=0.1). In analogy to Example 7.1.4.a, 256 mg (0.35 mmol) of this acid and 96 mg (0.52 mmol) of pentafluorophenol in 4 ml of dichloromethane were reacted with 100 mg (0.52 mmol) of N-ethyl-N'-(3-dimethylaminopropyl)-carbodiimide hydrochloride, whereupon the product was reacted at 0° with 1.5 ml of trifluoroacetic acid and 2 ml of dichloromethane. After precipitation from diethyl ether/hexane (1:1), filtration and drying 315 mg (90%) of pentafluorophenyl 2-[(S)-7-benzyloxycarbonyl-7-[N-[(L-$O^6$-methylglutamyl)-L-alanyl]]-5,6,7,8-tetrahydro-naphthalen-1-yloxy]-nicotinate trifluoroacetate were obtained as a white powder. M.p. 95°–99°. $[\alpha]_D$=+17.0° (chloroform, c=0.2). MS (ISP): 799.3 ($M^+$+$H^+$, 100).

EXAMPLE 7.4.14.a

A solution of 187 mg (0.2 mmol) of pentafluorophenyl 2-[(S)-7-benzyloxycarbonyl-7-[N-[(L-$O^6$-methylglutamyl)-L-alanyl]]-5,6,7,8-tetrahydro-naphthalen-1-yloxy]-nicotinate trifluoroacetate in 12 ml of N,N-dimethylformamide was added at room temperature within 18 hours to a solution of 30 mg of 4-(N,N-dimethylamino)-pyridine and 3 ml of pyridine in 250 ml of N,N-dimethylformamide. The reaction mixture was stirred for 2 hours and then concentrated, whereupon the residue was taken up in a mixture of ice, 0.1N HCl and dichloromethane. The aqueous phase was separated and extracted with dichloromethane, whereupon the combined organic phases were dried over magnesium sulphate and concentrated. The residue was suspended in acetonitrile, the suspension was filtered, the filter residue (40 mg of dimeric byproduct) was discarded and the filtrate was evaporated. The residue was pre-purified on 30 g of silica gel with chloroform/methanol (99:1→98:2) and the product obtained was chromatographed by means of preparative HPLC (column: Vydac 250-10, RP18, 30% acetonitrile→100% acetonitrile in 20 minutes), whereupon after lyophilization and drying 72 mg (50%) of benzyl (12S, 15S, 18S)-12-(2-methoxycarbonyl-ethyl)-15-methyl-10,13,16-trioxo-10,11,12,13,14,15,16,17, 18,19, 20,21-dodecahydro-1,18-etheno-pyrido[2,3-b]-benz [n][1,5,8,11]-oxatriazacyclopentadecene-18-carboxylate were obtained as a white powder. M.p. 120°–123° $[\alpha]_D$=−44.6° (chloroform, c=0.15). MS (ISP): 632.4 ($M^+$+$NH_4^+$, 15), 615.3 ($M^+$+$H^+$, 20), 531.4 (70), 431.4 (100).

EXAMPLE 7.4.1.5.a

A suspension of 47.0 mg (76 mmol) of benzyl (12S,15S, 18S)-12-(2-methoxycarbonyl-ethyl)-15-methyl-10,13,16-trioxo-10,11,1 2,13,14,15,16,17,18,19,20,21-dodecahydro-1,1 8-etheno-pyrido[2,3-b]benz[n][1,5,8,11

]oxatriazocyclopentadecene-18-carboxylate and 10 mg of palladium-charcoal (10%) in 5 ml of trifluoroethanol was hydrogenated at room temperature under normal pressure for 3 hours and then filtered over Celite, whereupon the filter residue was washed with trifluoroethanol and the filtrate was concentrated. The residue was taken up in chloroform and saturated sodium chloride solution, whereupon the pH was adjusted to 1 with 0.1N HCl and the aqueous phase was separated and exhaustively extracted with chloroform. The combined chloroform phases were dried over $Na_2SO_4$ and concentrated. The residue was suspended in diethyl ether, the suspension was filtered and the filter residue was dried in a high vacuum, 28.6 mg (71%) of (12S,15S,18S)-12-(2-methoxy-carbonyl-ethyl)-15-methyl-10,13,16-trioxo-10,11, 12,13,14,15, 16,17,18,19,20,21-dodecahydro-1,18-etheno-pyrido[2,3-b]benz[n][1,5,8,11]oxatriazacyclopentadecene-18-carboxylic acid being obtained as a white powder. M.p. (dec.)>120°. IR (Kbr) 3378 m (br.), 3060w, 2945w, 173sc, 1658s, 1588w, 1539m, 1422m, 1224m, 1175m. MS (ISP): 542.2 ($M^+ + NH_4^+$, 25), 525.3 ($M^+ + H^+$, 100).

EXAMPLE 7.4.2.1.a

A solution of 298 mg (0.48 mmol) of tert.-butyl 3-[(S)-7-benzyloxycarbonylamino-7-trimethylsilylethoxycarbonyl-5,6,7,8-tetrahydro-naphthalen-1-yloxy]nicotinate in 5 ml of ethanol was hydrogenated under a hydrogen atmosphere with 80 mg of palladium-charcoal (10%) at room temperature for 1 hour, whereupon the mixture was filtered over Hyflo and the filtrate was concentrated. The residue was dried in a high vacuum and chromatographed on 50 g of silica gel with chloroform/methanol (95:5), whereupon 190 mg (81.7%) of tert.-butyl 3-[(S)-7-amino-7-trimethylsilylethoxycarbonyl-5,6,7,8-tetrahydro-naphthalen-1-yloxy]-nicotinate were obtained. MS (ISP): 485.5 ($M^+ + H^+$, 50), 429 (15), 401.3 (100).

In analogy to Example 7.1.1.a, 170 mg (0.35 mmol) of tert.-butyl 3-[(S)-7-amino-7-trimethylsilylethoxycarbonyl-5,6,7,8-tetrahydronaphthalen-1-yloxy]-nicotinate, 140 mg (0.63 mmol) of Z-L-alanine, 127 mg (0.94 mmol) of 1-hydroxybenzotriazole 120 mg (0.63 mmol) of N-ethyl-N'-(3-dimethylaminopropyl)-carbodiimide hydrochloride and 120 µl (0.7 mmol) of ethyldiisopropylamine were reacted in 2 ml of N,N-dimethylformamide. After working up according to Example 7.1.1.a and chromatography on 60 g of silica gel with hexane/ethyl acetate (1:1) 145 mg (60%) of tert.-butyl 2-[(S)-7-[N-(benzyloxycarbonyl-L-alanyl)]-7-(2-trimethylsilylethoxy-carbonyl)-5,6,7,8-tetrahydro-naphthalen-1-yloxy]-nicotinate were obtained as an amorphous foam. M.p. 57°–67°. MS (ISP): 712.4 ($M^+ + Na^+$, 30) 690.5 ($M^+ + H^+$, 100), 606.4 (20). $[α]_D$=+49.50 ($CHCl_3$, c=0.2).

EXAMPLE 7.4.2.2.a

Analogously to Example 7.4.2.1.a, 166 mg (0.204 mmol) of tert.-butyl 2-[(S)-7-[N-(benzyloxycarbonyl-L-alanyl)]-7-(2-trimethylsilylethoxycarbonyl)-5,6,7,8-tetrahydro-naphthalen-1-yloxy]-nicotinate were hydrogenated in 4 ml of methanol with 34 mg of palladium-charcoal. In analogy to Example 7.1.1.a, 160 mg (0.24 mmol) of the dried product were reacted with 106 mg (0.36 mmol) of Z-Glu(OMe)OH, 73 mg (0.54 mmol) of 1-hydroxybenzotriazole, 69 mg (0.36 mmol) of N-ethyl-N'-(3-dimethylaminopropyl)-carbodiimide hydrochloride and 82 µl (0.48 mmol) of ethyldiisopropylamine. After working up and chromatography on 30 g of silica gel with chloroform/methanol (9:1) and after drying in a high vacuum 138 mg (80.7%) of tert.-butyl 2-[(S)-7-[N-[(benzyloxycarbonyl-L-$O^6$-methylglutamyl)-L-alanyl]]-7-(2-trimethylsilylethoxycarbonyl)-5,6,7,8-tetrahydro-naphthalen-1-yloxy]-nicotinate were obtained as an amorphous solid. M.p.>60°. $[α]_D$=+30.5° (chloroform, c=0.2). MS (ISP): 833.5, ($M^+ + H^+$, 100).

EXAMPLE 7.4.2.3.a 0.5 ml of trifluoroacetic acid was added dropwise under argon and while cooling with ice to a solution of 120 mg of tert.-butyl 2-[(S)-7-[N-[(benzyloxy-carbonyl-L-$O^6$-methylglutamyl)-L-alanyl]]-7-(2-trimethylsilylethoxycarbonyl)-5,6,7,8-tetrahydro-naphthalen-1-yloxy]-nicotinate in 1 ml of dichloromethane. The mixture was stirred at 0° for 1 hour and then evaporated to dryness. The residue was dried in a high vacuum and dissolved in 1 ml of dimethylformamide, whereupon 79.5 mg (0.432 mmol) of pentafluorophenol and 83.0 mg (0.432 mmol) of N-ethyl-N'-(3-dimethylaminopropyl)carbodiimide hydrochloride were added dropwise. The mixture was stirred at room temperature for 18 hours, whereupon the solvent was drawn off in a high vacuum. The residue was dried in a high vacuum and dissolved in 4 ml of N,N-dimethylformamide, and the solution was added at room temperature within 18 hours under hydrogen at atmospheric pressure to a suspension of 50 mg of N,N-dimethylaminopyridine, 1 ml of pyridine, 50 mg of palladium-charcoal and 100 ml of N,N-dimethylformamide. The mixture was stirred for a further 1 hour and was then concentrated. The residue was taken in chloroform and water and the organic phase was separated, dried over $NaSO_4$ and evaporated. The residue was dried in a high vacuum and subsequently stirred at room temperature in 2N HCl and dioxan, whereupon chloroform was added and the organic phase was separated, dried over magnesium sulphate and concentrated. The residue was precipitated from diethyl ether, filtered off and washed with diethyl ether, whereupon 38.5 mg (51%) of (12S,15S,18S)-12-(2-methoxycarbonyl-ethyl)-15-methyl-10,13,16-trioxo-10,11,12,13,14,15,16,17,18,-19,20,21-dodecahydro-1,1 8-etheno-pyrido[2,3-b]benz[n][1,5,8,11]oxatriazacyclopentadecene-18-carboxylic acid were obtained as a white powder. MS(ISP): 542.2 ($M^+ + NH_4^+$, 25), 525.3 ($M^+ + H^+$, 100). Identical with product from Example 7.4.1.5.a.

EXAMPLE 7.5.1.a

In analogy to Example 7.1.1.a, 309 mg (0.49 mmol) of prop-2-enyl 2-[(S)-7-benzyloxycarbonyl-7-[N-(tert.-butoxycarbonyl-L-alanyl)]-5,6,7,8-tetrahydro-naphthalen-1-yloxy]-nicotinate in 1.5 ml of dichloromethane were reacted at 0° with 1.0 ml of trifluoroacetic acid, whereupon the product was reacted with 183 mg (0.74 mmol) of Boc-Asp(OMe)OH, 149 mg (1.10 mmol) of 1-hydroxybenzotriazole, 141 mg (0.74 mmol) of N-ethyl-N'-(3-dimethylaminopropyl)-carbodiimide hydrochloride and 210 µl (1.23 mmol) of ethyldiisopropylamine in 4 ml of N,N-dimethylformamide. After chromatography on 90 g of silica gel with hexane/ethyl acetate (1:1→2:3) and drying in a high vacuum 360 mg (96.5%) of prop-2-enyl 2-[(S)-7-benzyloxycarbonyl-7-[N-[(tert.-butoxycarbonyl-L-$O^5$-methylaspartyl)-L-alanyl]]-5,6,7,8-tetrahydro-naphthalen-1-yloxy]-nicotinate were obtained as an amorphous solid. M.p. 55–73°. $[α]_D$=+34.0° (chloroform, c=0.2). MS (ISP): 776.6 ($M^+ + NH_4^+$, 40), 759.5 ($M^+ + H^+$, 100).

EXAMPLE 7.5.2.a

In analogy to Example 7.4.1.3.a, 330 mg (0.43 mmol) of prop-2-enyl 2-[(S)-7-benzyloxycarbonyl-7-[N-[(tert.- butoxycarbonyl-L-O$^5$-methylaspartyl)-L-alanyl]]-5,6,7,8-tetrahydro-naphthalen-1-yloxy]-nicotinate were reacted with 74.5 mg (0.65 mmol) of tetrakis(triphenylphosphine) palladium. After chromatography on 50 g of silica gel with chloroform/methanol (95:5→4:1), precipitation of the residue with diethyl ether/hexane (1:1), filtration and drying 231 mg (74%) mg (74%) of 2-[(S)-7-benzyloxycarbonyl-L-O$^5$-methylaspartyl)-L-alanyl]]-5,6,7,8-tetrahydro-naphthalen-1-yloxy]-nicotinic acid were obtained as a white powder. M.p. 116°–120°. [α]$_D$=+32.0° (chloroform, c=0.1).

In analogy to Example 7.1.3.a, 220 mg (0.31 mmol) of this acid were reacted with 84 mg (0.46 mmol) of pentafluorophenol and 88 mg (0.46 mmol) of N'-ethyl-N-(3-dimethylaminopropyl)-carbodiimide hydrochloride in 2 ml of dichloromethane, whereupon the product was treated at 0° with 1.5 ml of trifluoroacetic acid in 2 ml of dichloromethane. After precipitation from diethyl (sic) ether/hexane (1:1), filtration and drying 255 mg (92%) of pentafluorophenyl 2-[(S)-7-benzyloxycarbonyl-7-[N-(L-O$^5$-methylaspartyl-L-alanyl)]-5,6,7,8-tetrahydro-naphthalen-1-yloxy]-nicotinate trifluoroacetate were obtained as a white powder. M.p. 171°–174°. [α]$_D$=+13.0° (chloroform, c=0.2). MS (ISP): 785.3 (M$^+$+H$^+$, free amine, 100).

EXAMPLE 7.5.3.a

In analogy to Example 7.4.1.4.a, 190 mg of pentafluorophenyl 2-[(S)-7-benzyloxycarbonyl-7-[N-(L-O$^5$-methylaspartyl-L-alanyl)]-5,6,7,8-tetrahydro-naphthalen-1-yloxy]-nicotinate trifluoroacetate in 20 ml of N,N-dimethylformamide were added within 22 hours to a solution of 300 ml of N,N-dimethylformamide, 2.5 ml of pyridine and 80 mg of 4-(N,N-dimethylamino)pyridine. After chromatography on 50 g of silica gel with chloroform/methanol (99:→195:5) there were obtained 43 mg (17%) of dimeric byproduct as a white powder (MS (ISP): 1202.5 (M$^+$+H$^+$, 100), m.p. (dec.)>180° ) and 80 mg (~67%) of crude product which was purified by means of preparative HPLC chromatography (column: Vydac 250-10, RP 18, programme: 30% acetonitrile→100% acetonitrile in 20 minutes). After lyophilization and drying 60 mg (47%) of benzyl (12S,16S,19S)-16-methyl-10,13,17,23-tetraoxo-10,11,1 2,13,14,15,16,17,18,19,20,21,22,23-tetradecahydro-1, 19-etheno-12,15-metheno-pyrido[2,3-b]benz[o]-[1,5,9,1 2]-oxatriazacyclohexadecene-19-carboxylate were obtained as a white powder. M.p. (dec.)>200°. [α]$_D$=−17.0° (chloroform, c=0.2). MS (FAB): 569.3 (M$^+$+H$^+$, 60), 217 (60), 109 (30), 91 (100).

EXAMPLE 7.5.4.a

A suspension of 50 mg (88 mmol) of benzyl (12S,16S, 19S)-16-methyl-10,13,17,23-tetraoxo-10,11,1 2,13,14,15, 16,17,18, 19,20,21,22,23-tetradecahydro-1,19-etheno-12, 15-metheno-pyrido-[2,3-b]benz[o][1,5,9,12] oxatriazacyclohexadecene-19-carboxylate and 18 mg of palladium-charcoal (10%) in trifluoroethanol was hydrogenated at room temperature under normal pressure for 2 hours and then filtered over Celite, whereupon the filter residue was washed with trifluoroethanol and the filtrate was concentrated. The residue was suspended in chloroform, the suspension was filtered and the filter residue was washed firstly with chloroform and then with diethyl ether/ethyl acetate (1:1) and subsequently dried in a high vacuum, 41 mg (97%) of (12S, 16S,19S)-16-methyl-10,13,17,23-tetraoxo-10,11,12,13,14,15, 16,17,18,19,20,21,22,23-tetradecahydro-1,19-etheno-12,15-metheno-pyrido[2,3-b] benz[o][1,5,9,12]-oxatriazacyclohexadecene-19-carboxylic acid being obtained. M.p. (dec.)>255°. [α]$_D$=−4.0° (methanol, c=0.15). MS (ISN): 477.3 (M$^+$−H$^−$, 100).

EXAMPLE 7.6.1.a

A solution of 800 mg (1.66 mmol) of methyl (S)-2-(tert.-butoxycarbonylamino)-8-[2-(prop-2-enyloxycarbonyl)-phenoxy]-1,2,3,4-tetrahydronaphthalene-2-carboxylate in 3.5 ml of dichloromethane was reacted with 6 ml of trifluoroacetic acid at 0° C. in analogy to Example 7.1.1.a, whereupon the product was reacted with 660 mg (2.49 mmol) of Boc-L-phenylalanine, 477 mg (2.49 mmol) of N-ethyl-N'-(3-dimethylaminopropyl)-carbodiimidehydrochloride, 673 mg (4.98 mmol) of 1-hydroxybenzotriazole and 710 µl (4.15 mmol) of ethyldiisopropylamine in 5 ml of N,N-dimethylformamide. After chromatography on 150 g of silica gel with ethyl acetate/hexane (7:3→1:1) and after drying in a high vacuum there were obtained 826 mg (79%) of methyl (S)-2-N-(tert.butoxycarbonyl-L-phenylalanyl)-8-[2-(prop-2-enyloxycarbonyl)-phenoxy]-1,2,3,4-tetrahydronaphthalene-2-carboxylate as an amorphous solid. [α]$_D$=52.6° (c=0.3, chloroform). M.p. 65°–75°. MS (ISP): 646.5 (M$^+$+NH$_4^+$, 40), 629.5 (M$^+$+H$^+$, 50), 315.8 (100).

EXAMPLE 7.6.2.a

In analogy to Example 7.1.2.a, 4 ml of trifluoroacetic acid were added to a solution of 556 mg (0.88 mmol) of methyl (S)-2-N-(tert.butoxycarbonyl-L-phenylalanyl)-8-[2-(prop-2-enyloxycarbonyl)-phenoxy]-1,2,3,4-tetrahydro-naphthalene-2-carboxylic acid in 6 ml of dichloromethane and the residue obtained after the first step was reacted with 488 mg (1.32 mmol) of Z-L-tyrosine tert.butyl ether, 252.5 mg (1.32 mmol) of N-ethyl-N'-(3-dimethylaminopropyl) carbodiimide hydrochloride, 270 mg (2.0 mmol) of 1-hydroxybenzotriazole and 456 µl (2.67 mmol) ethyldiisopropylamine in 6 ml of N,N-dimethylformamide. After chromatography on 200 g of silica gel with ethyl acetate/hexane 3:7→1:1) there were obtained 683 mg (86.7%) of methyl (S)-2-N-[(tert.butoxycarbonyl-L-(O-tert.butyl) tyrosyl)-L-phenylalanyl]-8-[2-(prop-2-enyloxycarbonyl)-phenoxy]-1,2,3,4-tetrahydro-naphthalene-2-carboxylate as an amorphous solid. [α]$_D$=+34.7° (c=0.3, chloroform). M.p. 80°–90° (sintering). MS (ISP): 882.7 (M$^+$+H$^+$, 80), 470.0 (100), 461.2 (70).

EXAMPLE 7.6.3.a

In analogy to Example 7.4.1.3.a, N-methylaniline was added to 6 ml of a mixture of dimethyl sulphoxide, tetrahydrofuran and 0.5N hydrochloric acid (2:2:1) until the pH of the solution had reached 7, whereupon the solution was treated with 212 mg (0.24 mmol) of methyl (S)-2-N-[(tert.butoxycarbonyl-L-(O-tert.butyl)tyrosyl)-L-phenylalanyl]-8-[2-(prop-2-enyloxycarbonyl) phenoxy]-1, 2,3,4-tetrahydro-naphthalene-2-carboxylate and 41 mg (0.036 mmol) of tetrakis(triphenylphosphine)palladium. The residue was chromatographed on 30 g of silica gel with chloroform/methanol (95:5→92:8), whereupon after drying in a high vacuum 188 mg (93%) of methyl (S)-2-N-[(tert.butoxycarbonyl-L-(O-tert.butyl)tyrosyl)-L-phenylalanyl]-8-[2-carboxy-phenoxy]-1,2,3,4-tetrahydro-naphthalene-2-carboxylate were obtained as an amorphous solid. [α]$_D$=+18.3° (c=0.3, chloroform). M.p. (dec.)>110°. MS (FAB): 842.2 (M$^+$+H$^+$, 40), 708.2 (10), 342.0 (60), 324 (30), 282.0 (40), 216.9 (40), 120.1 (40), 91.1 (100).

EXAMPLE 7.6.4.a

In analogy to the second part of Example 7.1.3.a, 164 mg (0.195 mmol) of methyl (S)-2-N-[(tert.butoxycarbonyl-L-

(O-tert.butyl)tyrosyl)-L-phenylalanyl]-8-[2-carboxyphenoxy]-1,2,3,4-tetrahydro-naphthalene-2-carboxylate in 3 ml of dichloromethane were reacted with 56 mg (0.29 mmol) of N-ethyl-N'-(3-dimethylaminopropyl)carbodiimide hydrochloride and 53.8 mg (0.29 mmol) of pentafluorophenol. After chromatography on 45 g of silica gel with chloroform and after drying in a high vacuum there were obtained 175 mg (89%) of methyl (S)-2-N-[(tert.butoxycarbonyl-L-(O-tert.butyl)tyrosyl)-L-phenylalanyl]-8-[2-pentafluorophenyloxycarbonylphenoxy)-1,2,3,4-tetrahydronaphthalene-2-carboxylate as an amorphous solid. $[\alpha]_D=+21.0°$ (c=0.2, chloroform). M.p. 90°–98° (sintering). MS (ISP): 1008.6 ($M^+ + H^+$, 30), 532.8 (100).

EXAMPLE 7.6.5.a

A solution of 92 mg (0.091 mmol) of methyl (S)-2-N-[(tert.butoxycarbonyl-L-(O-tert.butyl)tyrosyl)-L-phenylalanyl]-8-(2-pentafluorophenyloxycarbonylphenoxy)-1,2,3,4-tetrahydro-naphthalene-2-carboxylate and 8.1 ml of cyclohexene were added dropwise at 900° under argon within 2 hours to a solution of 90 ml of dioxan, 1.8 ml of ethanol, 40 mg (0.027 mmol) of 4-pyrrolidinopyridine and 319 mg of palladium-charcoal (10%). The reaction mixture was stirred at 90° for a further 30 minutes, cooled and filtered over Celite. The filtrate was concentrated and the residue was taken up in ice-water and dichloromethane. Thereafter, the pH was adjusted to 3 using 1N hydrochloric acid, whereupon the aqueous phase was separated and thereafter extracted with dichloromethane, and the combined organic phases were washed with saturated sodium carbonate solution and saturated sodium chloride solution, dried over sodium sulphate and concentrated. The residue was chromatographed on 15 g of silica gel with ethyl acetate/hexane (3:7→3:2), whereupon after drying in a high vacuum there were s obtained 38 mg (60%) of methyl (12S,15S,18S)-15-benzyl-12-(4-tert.butoxybenzyl)-10,13,16-trioxo-10,11,1 2,13,14,15,16,17,18,19,20,21-dodecahydro-1,18-etheno-dibenz[b,n][1,5,8,11]oxatriazocyclopentadecene-18-carboxylate as a white powder. MS (ISP): 707.5 ($M^+ + NH_4^+$, 40), 690.4 ($M^+ + H^+$, 100)

IR (KBr): 3416s(br.), 3030w, 2977w, 2950w, 1738m, 1655s, 1537m, 1508s, 1461 m, 1237s, 1162w.

EXAMPLE 7.6.6.a 32 mg of lithium hydroxide monohydrate were added to a solution of 34 mg (0.05 retool) of methyl (12S,15S,18S)-15-benzyl-12-(4-tert.butoxybenzyl)-10,13,16-trioxo-10,11, 12,13, 14,15,16,17,18,19,20,21-dodecahydro-1,18-etheno-dibenz[b,n]-[1,5,8,11]oxatriazocyclopentadecene-18-carboxylate in 1.5 ml of tetrahydrofuran, methanol and water (3:1:1), following which the procedure analogous to Example 7.1.5.a was followed. The crude product was washed 2× with diethyl ether/hexane (1:1) and dried in a high vacuum, whereupon 29 mg (89%) of (12S,15S, 18S)-15-benzyl-18-(4-tert.butoxybenzyl)-10,13,16-trioxo-10,11, 12,13,14,15,16,17,18,19,20,21-dodecahydro-1,18-etheno-dibenz[b,n][1,5,8,11]oxatriazacyclopentadecene-18-carboxylic acid were obtained as a white powder. M.p. (dec.)>170°. MS (ISP): 676.4 ($M^+ + H^+$, 75), 409.2 (25), 388 (100).

EXAMPLE 8.1.a 17.6 μl (0.102 mmol) of N-ethyldiisopropylamine were added at 0° under argon to a solution of 21.0 mg (0.034 mmol) of (12S,15S,18S)-12,15-dimethyl-10,13,16-trioxo-10,11,1 2,13,14, 15,16,17,18,19,20,21-dodecahydro-1,18-etheno-dibenz [b,n]oxatriazacyclopentadecene-18-carboxylic acid, 45 mg (0.044 mmol) of L-alanyl-L-alanyl-L-alanyl-L-alanyl-L-alanyl-L-alanyl-(2-amino- 2-methyl-propionyl)-L-alanyl-L-alanine (4-iodo-phenyl)amide trifluoroacetate [C. E. Spiegler, Synthesis and conformational studies of peptides containing novel α,α-disubstituted amino acids, Dissertation, Zurich (University) 1993], 98 mg (0.0513 mmol) of N-ethyl-N'-(3-dimethylaminopropyl)-carbodiimide hydrochloride and 102.7 mg (0.075 mmol) of 1-hydroxybenzotriazole in 0.5 ml of N,N-dimethylformamide. The reaction mixture was stirred at 0° for 30 minutes and at room temperature for 4 hours and then poured into a mixture of ice, 0.5N HCl and chloroform/methanol (9:1). The aqueous phase was separated and exhaustively extracted with chloroform/methanol (9:1). The combined organic phases were dried over $Na_2SO^4$ and evaporated. The residue was pre-purified on 10 g of silica gel with chloroform/methanol (6:1). The product obtained (about 45 mg) was chromatographed by means of preparative HPLC (10 Nucleosil $7C_{18\ 250/1/2}$, Macherey Nagel), whereupon after lyophilization and drying in a high vacuum 40 mg (91.8%) of [(12S, 15S,18S)-12,15-dimethyl-10,13, 16-trioxo-10,11,12,13,14,15, 16,17,18,19,20,21-dodecahydro-1,1 8-etheno-dibenz[b,n][1,5,8, 11]oxatriazacyclopentadecen-18-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl)amide were obtained. MS (ISP): 1307.6 ($M^+ + H^+$, 5), 673 (100).

EXAMPLE 8.1.b

In analogy to Example 8.1.a, from 21.7 mg (0.048 mmol) of (12R,15R,18R)-12,15-dimethyl-10,13,16-trioxo-10,11, 12,13,14, 15,16,17,18,19,20,21-dodecahydro-1,18-etheno-dibenz[b,n]-oxatriazacyclopentadecene-18-carboxylic acid, 71.0 mg (0.072 mmol) of L-alanyl-L-alanyl-L-alanyl-L-alanyl-L-alanyl-L-alanyl-(2-amino-2-methyl-propionyl)-L-alanyl-L-alanine (4-iodophenyl)amide trifluoroacetate, 13.8 mg (0.072 mmol) of N-ethyl-N'-(3-dimethylaminopropyl)-carbodiimide hydrochloride and 14.3 mg (0.105 mmol) of 1-hydroxybenzotriazole in 0.5 ml of N,N-dimethylformamide there were obtained after lyophilization and drying 55 mg (87.7%) of [(12R,15R,18R)-12,15-dimethyl-10,13,16-trioxo-10,11,12,13,14,15,16,-17,18,19, 20,21-dodecahydro-1,1 8-etheno-dibenz[b,n][1,5,8,11] oxatriazacyclopentadecen-18-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl) amide. MS (ISP): 1307.6 ($M^+ + H^+$, 10), 673 (100).

EXAMPLE 8.2.b a) 5 g of aminomethylpolystyrene resin (Novabiochem, CH-4448 Läufelfingen, product No. 01-64-0010)were pre-swollen in 50 ml of DMF and treated in succession with 6.8 g of Fmoc-2,4-dimethoxy-4'-(carboxymethyloxy)-benzhydrylamine (Bachem AG, CH-4416 Bubendorf, Q 1660), 4.75 g of HBTU and 2.13 ml of DIPEA and shaken at 200° for 18 hours. The resulting Fmoc-amino resin was filtered off, washed thoroughly with DMF, isopropanol and diethyl ether and dried in a vacuum: yield: 7.9 g.

b) 6 g of this Fmoc-amino resin (loading: about 4 mmol) were filled into a peptide synthesizer Labortec SP 650 and subjected to the following synthesis cycle:

| Step | Reagent | Time |
|---|---|---|
| 1 | DMF | 2 × 1 min. |
| 2 | 20% piperidine/DMF | 1 × 7 min. |
| 3 | DMF | 5 × 1 min. |
| 4 | 2.5 eq. Fmoc- or Z.amino acid/DMF + 2.5 eq. 1-benzotriazol-1-yl-tetra-methyluronium hexafluorophosphate [HBTU] or tetrafluoroborate [TBTU] + 2.5 eq. diisopropylethylamine | 1 × 90 min. |
| 5 | DMF | 3 × 1 min. |
| 6 | isopropyl alcohol | 2 × 1 min. |

About 50 ml of solvent were used in each step. Fmoc-Leu-OH, Fmoc-Lys(Boc)-OH, Fmoc-Gln(Trt)-OH- Fmoc-Ala-OH; Fmoc-Ile-OH, Fmoc-Glu(OBut)-OH, Fmoc-Ala-OH, Fmoc-Lys(Boc)-OH and Fmoc-Leu-OH were coupled according to the above protocol. At the conclusion of the synthesis the Fmoc protecting group was cleaved off with 20% piperidine/DMF as described in step 2 of the synthesis and the peptide resin was dried in a vacuum. 9.3 g of N-[Leu-Lys(Boc)-Ala-Glu(OBut)-Ile-Ala-Gln(Trt)-Lys-(Boc)-Leu]-amino resin were obtained.

d) 300 mg of N-[Leu-Lys(Boc)-Ala-Glu(OBut)-Ile-Ala-Gln(Trt)-Lys-(Boc)-Leu]-amino resin were pre-swollen in 2 ml of DMF and treated in succession with 32 mg of (12S,15S,18S)-12,15-dimethyl-10,13,16-trioxo-10,11,12, 13,14,15,16,17,18,19,20,21-dodecahydro-1,18-etheno-dibenz[b,n]oxatriazacyclopentadecene-18-carboxylic acid, 32 mg of TBTU and 18 µl of DIPEA. The reaction mixture was shaken for 1 hour and the resin was filtered off, washed with DMF, isopropanol and diethyl ether and suspended in 50 ml of a solution consisting of 82.5% TFA/5% phenol/5% thioanisole/2.5% 1,2-dimercaptoethanol/5% H$_2$O [Reagent K] and shaken at 20° for 2 hours. Then, the resin was filtered off and washed with trifluoroacetic acid and the combined filtrates were concentrated in a vacuum. The residue was digested with diethyl ether, dissolved in dil. trifluoroacetic acid and purified by means of HPLC (on a LiChrospher column RP-18 10µm (2.5×25 cm) in the gradiant system 0.1% trifluoroacetic acid-ethanol. After lyophilization 24.9 mg of [(12R,15R,18R)-12,15-dimethyl-10,13, 16-trioxo-10, 11,12, 13,14,15,16,17,18,19,20,21-dodecahydro-1,1 8-etheno-dibenz[b,n][1,5,8,11]-oxatriazacyclopentadecen-18-ylcarbonyl]-L-leucyl-L-lysyl-L-alanyl-L-glutamyl-L-isoleucyl-L-alanyl-L-glutaminyl-L-lysyl-L-leucinamide trifluoroacetate (1:2) were obtained. MS (ISP) 1446.0.

EXAMPLE 8.2.a

In an analogous manner to that described in Example 8.2.b, but using (12R,15R,18R)-12,15-dimethyl-10,13,16-trioxo-10,11, 12,13,14,15,16,17,18,19,20,21-dodecahydro-1,18-etheno-dibenz[b,n]oxatriazacyclopentadecene-18-carboxylic acid there was synthesized [(12S,15S,18S)-12, 15-dimethyl-10,13,16-trioxo-10, 11,1 2,13,14,15,16,17,18, 19,20,21-dodecahydro-1,18-etheno-dibenz[b,n][1,5,8,11] oxatriazacyclopentadecen-18-ylcarbonyl]-L-leucyl-L-lysyl-L-alanyl-L-glutamyl-L-isoleucyl-L-alanyl-L-glutaminyl-L-lysyl-L-leucinamide trifluoroacetate (1:2). Yield: 26 mg of lyophilizate. MS (FAB) 1445.8 MH$^+$, 100).

EXAMPLE 8.3.a

In analogy to Example 8.1.a, 16.0 mg (0.03 mmol) of (14aS, 17S,20S)-8-acetylamino-17-methyl-10,15,18-trioxo-11,12, 13,14,14a, 15,16,17,18,19,20,21,22,23-tetradecahydro-1,20-etheno-10H-pyrrolo[1,2-e]dibenz[b,n] [1,5,8,11]oxatriazacyclopentadecene-20-carboxylic acid were reacted with 44.0 mg (0.045 mmol) of L-alanyl-L-alanyl-L-alanyl-L-alanyl-L-alanyl-L-alanyl-(2-amino-2-methyl-propionyl)-L-alanyl-L-alanine (4-iodophenyl)amide trifluoroacetate, 8.6 mg (0.045 mmol) of N-ethyl-N'-(3-dimethylaminopropyl)-carbodiimide hydrochloride, 9.0 mg (0.068 mmol) of 1-hydroxybenzotriazole and 15 µl (0.09 mmol) of ethyldiisopropylamine in 1.5 ml of dimethylformamide. The product obtained was pre-purified on 6 g of silica gel with chloroform/methanol (95:5→9:1). After preparative HPLC chromatography (column: Vydac 250-19, programme: 50% acetonitrile→85% acetonitrile in 20 minutes), lyophilization and drying 34.8 mg (84%) of [(14aS,17S,20S)-8-acetylamino-17-methyl-10,15,18-trioxo-11,12,13,14,14a,15,16,17,18,19,20,21,22,23-tetradecahydro-1,20-etheno-10H-pyrrolo[1,2-e]dibenz[b,n] [1,5,8, 11]oxatriazacyclopentadecen-20-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl)amide were obtained as a while solid.

M.p. (dec.)>215°, [α]$_D$=+11.0° (chloroform, c=0.1), MS (ISP): 1411.4 (M$^+$+Na$^+$, 10), 1389.4 (M$^+$, H$^+$, 10), 714.4 (100).

EXAMPLE 8.4.a.

In analogy to Example 8.1.a., 13.0 mg (24 µmol) of (12S, 15S, 18S)-12-(2-methoxycarbonyl-ethyl)-15-methyl-10,13, 16-trioxo-10,11,12, 13,14,15,16,17,18,19,20,21-dodecahydro-1,18-etheno pyrido[2,3-b]benz[n][1,5,8,11] oxatriazacyclopentadecene-18-carboxylic acid, 7.1 mg (37 µmol) of N-ethyl-N'-(3-dimethylaminopropyl)-carbodiimide, 7.5 mg (56.0 µmol) of 1-hydroxybenzotriazole, 36.5 mg (37.0 µmol) of L-alanyl-L-alanyl-L-alanyl-L-alanyl-L-alanyl-L-alanyl-(2-amino-2-methyl-propionyl)-L-alanyl-L-alanine (4-iodophenyl)amide trifluoroacetate and 12.3 µl (72.0 µmol) of N-ethyldiisopropylamine were reacted in 1.5 ml of N,N-dimethylformamide. The residue was suspended in hot acetonitrile, filtered off, washed with acetonitrile, filtered off, washed with acetonitrile and dried in a high vacuum, a total of 24.4 mg (71%) of [(12S, 15S, 18S)-12-(2-methoxycarbonyl-ethyl)-15-methyl-10,13,16-trioxo-10,11, 12,13,14,15,16,17,18,19,20,21-dodecahydro-1,18-etheno-pyrido[2,3-b]benz-[n][1,5,8,11]oxatriazacyclopentadecen-18-ylcarbonyl]-L-alanyl- L-alanyl-L-alanyl-L-alanyl-L-alanyl-L-alanyl-(2-amino-2-methyl-propionyl)-L-alanyl-L-alanine (4-iodophenyl)amide being obtained as a white powder. M.p. (dec.)>310°. (M$^+$, +H$^+$, 10), 718.2 (20), 465.4 (30), 289.4 (65), 267.4 (100).

EXAMPLE 8.5.a

In analogy to Example 8.1.a, 15.0 mg (26.0 µmol) of (12S, 16S, 19S)-16-methyl-10,13,17,23-tetraoxo-10,11,12,13,14, 15, 16,17,18,19,20,21,22,23-tetradecahydro-1,19-etheno-12,15- metheno-pyrido[2,3-b]benz[o][1,5,9,12] oxatriazacyclohexadecene-19-carboxylic acid, 7.5 mg (39.0 µmol) of N-ethyl-N'-(3-dimethylaminopropyl)-carbodiimide hydrochloride, 7.9 mg (59.0 µmol)of 1-hydroxybenzotriazole, 38.5 mg (39.0 µmol) of L-alanyl-L-alanyl-L-alanyl-L-alanyl-L-alanyl-L-alanyl-(2-amino-2-methyl-propionyl)-L-alanyl-L-alanine-(4-iodophenyl)amide trifluoroacetate and 13.6 mg (80.0 µmol) of ethyldiisopropylamine were reacted in 1.5 ml of N,N-dimethylformamide. The residue was taken up in chloroform and water, the aqueous phase was exhaustively extracted with chloroform and the combined organic phases were dried over sodium sulphate, filtered and concentrated. The solid residue was suspended in acetonitrile and filtered off, whereupon after drying 15.0 mg (43.0%) of [(12S,16S, 19S)-16-methyl-10,13,17,23-tetraoxo-10,11,12,13,14,15, 16,17,18,19,20,21,22,23-tetradecahydro-1,19-etheno-12, 15-metheno-pyrido[2,3-b]benz[o][1,5,9,12]-oxatriazacyclohexadecen-19-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl)amide were obtained as a white powder. M.p. (dec.)>240°. MS (FAB): 1333.3 (M$^+$+H$^+$, 60), 1114.4 (70), 1043.3 (40), 972.3 (50), 887.3 (20), 816.3 (20), 745.2 (30), 674.2 (30), 532.0 (60), 433.0 (25), 324.9 (50), 216.9 (90), 91.2 (100).

EXAMPLE 8.6.a

The procedure analogous to Example 8.1.a was followed starting from a solution of 9.0 mg (13.0 µmol) of (12S,15S, 18S)-15-benzyl-18-(4-tert.butoxybenzyl)-10,13,16-trioxo-10,11,12, 13,14,15,16,17,18,19,20,21-dodecahydro-1,18-etheno-dibenz-[b,n][1,5,8,11]oxatriazacyclopentadecene-18-carboxylic acid, 19.7 mg (19.9 µmol) of L-alanyl-L-alanyl-L-alanyl-L-alanyl-L-alanyl-L-alanyl-(2-amino-2-methylpropionyl)-L-alanyl-L-alanine (4-iodophenyl)amide trifluoroacetate, 3.8 mg (19.9 µmol) of N-ethyl-N'-(3-dimethylaminopropyl)-carbodiimide hydrochloride, 3.5 mg (26.0 µmol) of 1-hydroxybenzotriazole and 4.4 µl (26.0 µmol) of ethyldiisopropylamine in 0.3 ml of N,N-dimethylformamide. The crude product was chromatographed on 4 g of silica gel with chloroform/methanol (95:5) and the product, obtained as a solid, was suspended in diethyl ether, filtered off and dried in a high vacuum, whereupon there were obtained 18 mg (89.5%) of [(12S, 15S,18S)-15-benzyl-18-(4-tert.butoxybenzyl)-10,13,16-trioxo-10,11,1 2,13,14,15,16,17,18,19,20,21-dodecahydro-1,18-etheno-dibenz[b,n][1,5,8,11]oxatriazacyclopentadecen-18-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl) amide. M.p. (dec.) 230°. MS (ISP): 1547.8 (M$^+$+NH$^+$100), 1530.6 (M$^+$+H$^+$, 20), 766 (30).

EXAMPLE 9.1.1.a 1.7 mg of sodium bicarbonate were added to a solution of 48.2 mg (63.8 µmol) of pentafluorophenyl (S)-2-(fluoren-9-ylmethoxycarbonyl)-8-[2-(prop-2-enyloxycarbonyl)-phenoxy]-1,2,3,4-tetrahydro-naphthalene-2-carboxylate and 60.0 mg (60.8 µmol) of L-alanyl-L-alanyl-L-alanyl-L-alanyl-L-alanyl-L-alanyl-(2-amino-2-methyl-propionyl)-L-alanyl-L-alanine (4-iodophenyl)amide trifluoroacetate in 1 ml of N,N-dimethylformamide. The reaction mixture was stirred at room temperature for 4 hours and then poured into a mixture of water and ethyl acetate. The organic phase was separated, washed with saturated sodium bicarbonate and sodium chloride solutions, dried over sodium sulphate and evaporated. The residue was precipitated from diethyl ether/hexane and dried in a high vacuum, whereupon 56.2 mg (61%) of [(S)-[2-(fluoren-9-ylmethoxycarbonylamino)-8-[2-[(prop-2-enyloxycarbonyl)-phenoxy]]-1,2,3,4-tetrahydro-naphthalen-2-ylcarbonyl]-L-alanyl-L-alanyl-L-alanyl-L-alanyl-L-alanyl-L-alanyl-(2-amino-2-methylpropionyl)-L-alanyl-L-alanine (4-iodophenyl)amide were obtained as a white powder. MS (ISP): 682.3 (M$^+$+Na$^+$, 25), 660.4 (M$^+$+H$^+$, 100), 441.4 (35). IR(KBr): 3325m (br), 3065w, 2983w, 2938w, 1662s, 1534s, 1453m, 1382w, 1300w, 1243m, 1081 w.

EXAMPLE 9.1.2.a

A solution of 32 mg (22.2 mmol) of [(S)-[2-(fluoren-9-yl-methoxy-carbonylamino)-8-[2-[(prop-2-enyloxy-carbonyl)-phenoxy]]-1,2,3,4-tetrahydro-naphthalen-2-ylcarbonyl]-L-alanyl-L-alanyl-L-alanyl-L-alanyl-L-alanyl-L-alanyl-(2-amino-2-methylpropionyl)-L-alanyl-L-alanine (4-iodophenyl)amide in 1 ml of 20% piperidine/N,N-dimethylformamide was stirred at room temperature for 20 hours and then evaporated. The residue was precipitated from diethyl ether, filtered off, washed with diethyl ether and dried in a high vacuum. The crude product obtained (27 mg) was dissolved in 0.5 ml of N,N-dimethylformamide, whereupon the solution was treated with 6.4 mg (33.3 µmol) of N-ethyl-N'-(3-dimethylaminopropyl)-carbodiimide hydrochloride, 6.6 mg (48.8 µmol) of 1-hydroxybenzotriazole, 6.3 mg (33.3 µmol) of Boc-L-alanine and 11.3 ml of ethyl diisopropylamine, stirred at room temperature for 17 hours under argon and then poured into a mixture of water and chloroform. The organic phase was separated, extracted with saturated sodium bicarbonate solution, dried over Na$_2$SO$_4$ and concentrated. The residue was precipitated with hexane, filtered off and dried in a high vacuum. The crude product (30 mg) was chromatographed using preparative HPLC chromatography (column: Vydac C18, programme: 50% acetonitrile→100% acetonitrile in 30 minutes), whereupon after lyophilization and drying 26.2 mg (90%) of [(S)-[2-[N-(tert.-butoxycarbonyl-L-alanyl)]-8-[2-[(prop-2-enyloxy-carbonyl)-phenoxy]]-1,2,3,4-tetrahydro-naphthalen- 2-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl)amide were obtained. MS (ISP): 1410.6 (M$^+$+Na$^+$, 15), 1393.4 (M$^+$+H+, 10), 716.6 (100), 538 (20). IR (KBr): 3324 m(br), 3065w, 2982w, 2937w, 1663s, 1534s, 1455w, 1382w, 1302w, 1247w, 1165w.

EXAMPLE 9.1.3.a

A solution of 24.0 mg (17.2 mmol) of [(S)-[2-[N-(tert.butoxycarbonyl-L-alanyl)]-8-[2-[(prop-2-enyloxycarbonyl)-phenoxy]]-1,2,3,4-tetrahydro-naphthalen-2-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl)amide in 0.5 ml of dichloromethane was treated with 0.5 ml of trifluoroacetic acid while cooing with ice, whereupon the mixture was stirred at room temperature for 28 hours and then concentrated. The residue was precipitated from diethyl ether/hexane (1:1), filtered off, dried in a high vacuum and dissolved in 0.5 ml of N,N-dimethylformamide. The solution was treated at room temperature under argon with 4.9 mg (25.8 µmol) of N-ethyl-N'-(3-dimethylaminopropyl)-carbodiimide hydrochloride, 5.1 mg (37.8 µmol) of 1-hydroxybenzotriazole, 4.5 mg (25.8 µmol) of Alloc-L-alanine and 8.8 ml (51.6 µmol) of N-ethyldiisopropylamine, whereupon the mixture was stirred at room temperature for 6 hours. After working up and preparative HPLC chromatography in analogy to Example 9.1.2.a 19.8 mg (80.2%) of [(S)-[2-[N-[[(prop-2-enyloxycarbonyl)-L-alanyl]-L-alanyl]]-8-[2-[(prop-2-enyloxy-carbonyl)-phenoxy]]-1,2,3,4-tetrahydro-naphthalen-2-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl)amide were obtained as a white powder. MS (ISP): 1448.6 (M$^+$+H+, 10), 744.0 (100). IR (KBr): 3320m (br), 3065w, 2984w, 2938w, 1661s, 1537s, 1455m, 1382w, 1302w, 1243m, 1166w.

EXAMPLE 9.1.4.a 6.8 mg of tetrakis(triphenylphosphine)palladium were added to a mixture of 110 µl of N-methyl-aniline and 600 82

1 of dimethyl sulphoxide. This mixture was stirred at room temperature and treated with a solution of 17.8 mg (12.3 μmol) of [(S)-[2-[N-[[(prop-2-enyloxycarbonyl)-L-alanyl]-L-alanyl]]-8-[2-[(prop-2-enyloxycarbonyl)-phenoxy]]-1,2, 3,4-tetrahydro-naphthalen-2-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl)amide in 1.5 ml of tetrahydrofuran/dimethyl sulphoxide/0.5N HCl (2:2:1), whereupon the reaction mixture was stirred at room temperature for 20 hours and then concentrated. The residue was purified by means of preparative HPLC chromatography (column: Vydac C18; programme: 30% acetonitrile→100% acetonitrile in 30 minutes), whereupon after lyophilization and drying 17.0 mg (96%) of [(S)-[2-[N-(L-alanyl-L-alanyl)]-8-(2-carboxy-phenoxy)-5,6,7,8-tetrahydronaphthalen-2-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl)amide were obtained as a white powder. MS (ISP): 1324.4 (M$^+$+H$^+$, 40), 663.0 (75), 553.6 (100), 518 (30(25). IR (KBr): 3318 m (br), 3060w, 2985w, 2938w, 1666s, 1532s, 1456m, 1383w, 1243m, 1202m.

EXAMPLE 9.1.5.a 2.3 μl of diphenylphosphoryl azide were added at room temperature and under argon to a suspension of 4.4 mg (3.1 μmol) of [(S)-[2-[N-(L-alanyl-L-alanyl)]-8-(2-carboxy-phenoxy)-5,6,7,8-tetrahydro-naphthalen-2-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl)amide and 1.3 mg of sodium carbonate in 10 ml of N,N-dimethylformamide, whereupon the reaction mixture was stirred for 20 hours and then concentrated. The residue was taken up in acetonitrile and purified by means of preparative HPLC chromatography (column: Vydac C18; programme: 30% acetonitrile→100% acetonitrile in 30 minutes), whereupon after lyophilization and drying 2.7 mg (67%) of [(12S,15S,18S)-12,15-dimethyl-10,13,16-trioxo-10,11,12,13,14,15,16,17,18,19, 20,21-dodecahydro-1,18-etheno-dibenz[b,n][1,5,8,11]oxatriazacyclopentadecine-18-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl)amide were obtained as a white powder. Identical with product from Example 8.1.a.

EXAMPLE 9.2.a 41 mg (0.12 mmol) of pentafluorophenyl (S)-2-(fluoren-9-ylmethoxycarbonyl)-8-[2-(prop-2-enyloxycarbonyl)-phenoxy]-1,2, 3,4-tetrahydro-naphthalene-2-carboxylate were added to a mixture of 450 mg (about 0.11 mmol) of the peptide resin obtained according to paragraph d) of Example 8.2.b. The reaction mixture was shaken for 18 hours in a peptide synthesizer Labortec SP 650, washed three times with 10 ml of N,N-dimethylformamide and treated for 20 hours with 10 ml of 20% piperidine solution in N,N-dimethylformamide. 137 mg (0.44 mmol) of Fmoc-L-alanine, 91 mg (0.40 mmol) of N-ethyl-N'-(3-dimethylaminopropyl)-carbodiimide hydrochloride, 4.9 mg (0.04 mmol) of N-hydroxypyridin-2-one and 2.5 ml of N,N-dimethylformamide were added to the resin, whereupon the mixture was shaken for 2 hours. Thereafter, the resin was filtered off and the coupling step was repeated once more with Fmoc-L-alanine, with the difference that the mixture was shaken for 18 hours. The resin was washed with N,N-dimethylformamide, whereupon the Fmoc group was cleaved off by three treatments with 20% piperidine solution in N,N-dimethylformamide for 45 minutes each time and the resin was washed analogously as described above. Subsequently, 76 mg (0.44 mmol) of Alloc-L-alanine, 91 mg (0.40 mmol) of N-ethyl-N'-(3-dimethylaminopropyl) carbodiimide hydrochloride, 4.9 mg (0.04 mmol) of N-hydroxypyridin-2-one and 2.5 ml of N,N-dimethylformamide were added to the resin, whereupon the mixture was shaken for 20 hours and washed with N,N-dimethylformamide. The coupling with Alloc-L-alanine was repeated analogously to the coupling with Fmoc-L-alanine, whereupon the resin was washed with N,N-dimethylformamide and dried. 3.5 ml of a solution of dimethyl sulphoxide, tetrahydrofuran and 0.5N hydrochloric acid (2:2:1) and 350 μl of N-methylaniline were added to the dried resin, whereupon the mixture was made oxygen-free with argon and treated with 19.0 mg (16.5 μmol) of tetrakis (triphenylphosphine)palladium. The reaction mixture was shaken under argon for 22 hours and then washed with N,N-dimethylformamide. This procedure was repeated once more. Subsequently, 125 mg (0.33 mmol) of 1-benzotriazol-1-yl-tetramethyluronium hexafluorophosphate (HBTU), 94 μl (0.55 mmol) of ethyldiisopropylamine and 1.5 ml of N,N-dimethylformamide were added to the resin, whereupon the mixture was shaken for 2 hours, filtered and washed in succession with N,N-dimethylformamide, isopropanol and diethyl ether and dried. The peptide resin was subsequently cleaved by treatment for 2 hours with a solution of trifluoroacetic acid/water (95:5), whereupon the mixture was filtered and the filtrate was evaporated. The residue was precipitated with diethyl ether and purified by means of preparative HPLC chromatography (column: Lichrosorb Select B, 10 μm (250×10 mm); programme: 30% acetonitrile→50% acetonitrile in 20 minutes; retention time of the product 11.8 minutes), whereupon 8.5 mg of pure (12S,15S, 18S)-12,15-dimethyl-10,13,16-trioxo-10,11,12, 13, 14,15,16, 17,18,19,20,21-dodecahydro-1,18-etheno-dibenz[b ,n][1,5,8,11]oxatriazacyclopentadecine-18-ylcarbonyl]-L-leucyl-L-lysyl-L-alanyl-L-glutamyl-L-isoleucyl-L-alanyl-L-glutaminyl-L-lysyl-L-leucinamide were obtained. MS (FAB): 1445.5 (M$^+$) (identical with product from Example 8.2.a.).

EXAMPLE 10.1.a

About 5 mg of LiOH. 1 H$_2$O were added while cooling with ice to a solution of 10.0 mg (7.2 μmol) of [(12S,15S, 18S)-12-(2-methoxycarbonyl-ethyl)-15-methyl-10,13,16-trioxo-10,11, 12,13,14,15,16,17,18,19,20,21-dodecahydro-1,18-etheno-pyrido[2,3-b]benz[n][1,5,8,11]oxatriaza-cyclopentadecene-18-carbonyl]-L-alanyl-L-alanyl-L-alanyl-L-alanyl-L-alanyl-L-alanyl-(2-amino-2-methyl-propionyl)-L-alanyl-L-alanine (4-iodophenyl)amide in 1 ml of tetrahydrofuran/methanol/water (3:1:1 ). The reaction mixture was stirred for 1 hour and then concentrated. The residue was taken up in acetonitrile/water (1:1), the pH was adjusted to about 4 with 1N HCl, whereupon lyophilization was carried out. The product was purified by means of HPLC chromatography (column: Select B 250-10; programme:5% acetonitrile→100% acetonitrile in 20 minutes), whereupon after lyophilization and drying 9.1 mg (94.3%) of [(12S, 15S, 18S)-12-(2-carboxy-ethyl)-15-methyl-10,13, 16-trioxo- 10,11,12,13,14,15,16,17,18,19,20,21-dodecahydro-1,18-etheno-pyrido[2,3-b]benz[n][1,5,8,11] oxatriazacyclopentadecen-18- ylcarbonyl]-L-alanyl-L-alanyl-L-alanyl-L-alanyl-L-alanyl-L-alanyl- (2-amino-2-methyl-propionyl)-L-alanyl-L-alanine (4-iodophenyl)amide were obtained as a white solid residue. MS (ISN): 681.4 [(M$^+$−2H)$^2$. 0.5, 100].

EXAMPLE 10.2.a.

5 mg of lithium hydroxide monohydrate were added while cooling with ice to a solution of 10.0 mg (7.50 µmol) of [(12S, 16S,19S)-16-methyl-10,13,17,23-tetraoxo-10,11,12, 13,14, 15,16,17,18,19,20,21,22,23-tetradecahydro-1,19-etheno-12,15-metheno-pyrido[2,3-b]benz[o][1,5,9,1 21oxatriazacyclohexadecen-19-ylcarbonyl]-L-alanyl-L-alanyl-L-alanyl-L-alanyl-L-alanyl-L-alanyl-(2-amino-2-methyl-propionyl)-L-alanyl-L-alanyl (4-iodophenyl)amide in 0.5 ml of tetrahydrofuran, methanol and water (3:1:1) and the reaction mixture was stirred at 0° for 2 hours and at room temperature for 15 minutes. Thereafter, the pH of the solution was adjusted to about 3 by means of 1N hydrochloric acid solution, the solution was concentrated and the residue was purified by means of preparative HPLC (column: Select B 250–10, programme: 10% acetonitrile→95% acetonitrile in 20 minutes). After lyophilization and drying 9.5 mg (93.3%) of [(12S,15S,18S)-12-(2-carboxymethyl)-15-methyl-10,13,16-trioxo-10,11,12,13,14,15,16,17,18,19,20, 21-dodecahydro-10,11,18-etheno-pyrido[2,3-b]benz[n][1,5,8]oxatriazacyclopentadecen-18-ylcarbonyl]-L-alanyl-L-alanyl-L-alanyl-L-alanyl-L-alanyl-L-alanyl-(2-amino-2-methyl-propionyl)-L-alanyl-L-alanyl-(4-iodophenyl)amide were obtained as a white amorphous powder. MS (ISP): 1351.4 (M$^+$+H$^+$, 20), 704.4 (40), 695.4 (100), 487.4(20), 465.4 (20).

EXAMPLE 10.3.a 0.2 ml of trifluoroacetic acid was added at 0° under argon to a solution of 15.0 mg (9.8 µmol) of [(12S,15S,18S)-15-benzyl-18-(4-tert.butoxybenzyl)-10,13,16-trioxo-10,11,12, 13,14,15,16, 17,18,19,20,21-dodecahydro-1,18-ethenodibenz[b, n][1,5,8,11]oxatriazacyclopentadecen-18-ylcarbonyl]-L-alanyl-L-alanyl-L-alanyl-L-alanyl-L-alanyl-L-alanyl-(2-amino-2-methyl-propionyl)-L-alanyl-L-alanine (4-iodophenyl)amide in 0.8 ml of dichloromethane. The reaction mixture was stirred at 0° for 2 hours, whereupon the solvent was distilled off in a high vacuum. The solid residue was washed 2× with diethyl ether, whereupon 13.0 mg (89.9%) of [(12S,15S,18S)-15-benzyl-18-(4-hydroxybenzyl)-10,13,16-trioxo-10,11,12,13,14,15,16,17, 18, 19,20,21-dodecahydro-1,18-etheno-dibenz[b,n][1,5,8, 11]oxatriazacyclopentadecen-18-ylcarbonyl]-L-alanyl-L-alanyl-L-alanyl-L-alanyl-alanyl-L-alanyl-(2-amino-2-methyl-propionyl)-L-alanyl-L-alanine (4-iodophenyl)amide were obtained as a white powder. M.p. (dec.)>215°. MS (ISP): 1513.6 (M$^+$+K$^+$, 30), 1497.5 (M$^+$+Na$^+$, 100). IR (KBr): 3311 m(br.), 3070w, 2990w, 2945w, 1691s, 1587w, 1532s, 1456w, 1305w, 1241w.

We claim:

1. A compound of the formula:

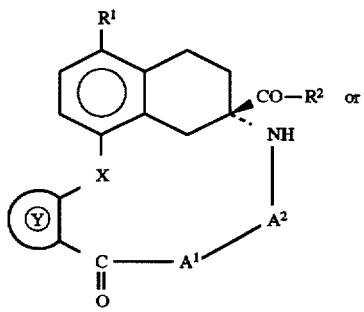

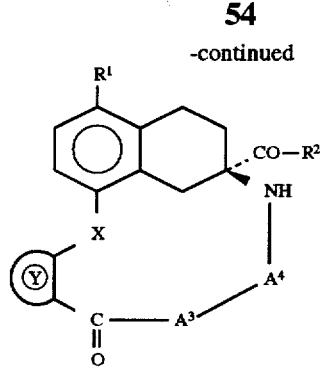

wherein

R$^1$ is hydrogen, bromine, cyano, formyl, hydroxy, lower alkyl, lower alkenyl, lower alkynyl, lower alkoxy, aryloxy, lower aralkoxy or aryl;

R$^2$ is an amino acid residue or a chain of 2 to 20 amino acid residues derived from a biologically active peptide or protein, wherein the side-chain(s) of said amino acid residue(s) is/are protected or unprotected and wherein the acid group of the C-terminal amino acid is the free acid, is protected, or is in the form of an amide A$^1$, A$^2$, A$^3$ and A$^4$ each are residues of α-amino acids, wherein A$^1$ or A$^2$ are in the L configuration and A$^3$ or A$^4$ are in the D configuration when the α-C atom of said α-amino acid residue is asymmetric;

X is oxygen or sulphur; and

Y and the two C atoms together are an aromatic ring selected from the group consisting of benzene, furan, thiophene, pyridine or pyrimidine, wherein said aromatic ring is substituted or unsubstituted;

and the salts thereof.

2. The compound of claim 1 wherein X is sulfur.

3. The compound of claim 1 wherein X is oxygen.

4. The compound of claim 3 wherein the aromatic ring is benzene or pyridine which is unsubstituted or mono- or di-substituted by nitro, amino, lower alkanoylamino, hydroxy, lower alkoxy, lower alkanoyloxy, lower alkyl, fluorine, cyano, carboxy or formyl, or is condensed with a benzene ring to form a bicyclic system.

5. The compound of claim 4 wherein R$^1$ is hydrogen.

6. The compound of claim 4 wherein the aromatic ring is benzene, benzene substituted by alkanoylamino, or pyridine.

7. The compound of claim 6 wherein R$^1$ is hydrogen.

8. The compound of claim 6 wherein A$^1$ or A$^3$ is a residue of asparagine, aspartic acid, glutamine, glutamic acid, lysine or 2-amino-2-methylpropionic acid, and A$^2$ or A$^4$ is a residue of L- or D-alanine, asparagine, aspartic acid, glutamine, glutamic acid or lysine.

9. The compound of claim 8 wherein R$^1$ is hydrogen.

10. The compound of claim 8 wherein A$^1$ or A$^3$ is a residue of L- or D-alanine or lysine, and A$^2$ or A$^4$ is a residue of L- or D-alanine.

11. The compound of claim 10 wherein R$^1$ is hydrogen.

12. The compound of claim 11 wherein R$^2$ contains 9 to 15 amino acid residues.

13. The compound of claim 12 wherein R$^2$ contains 9, 12 or 15 amino acid residues.

14. A compound of the formulae:

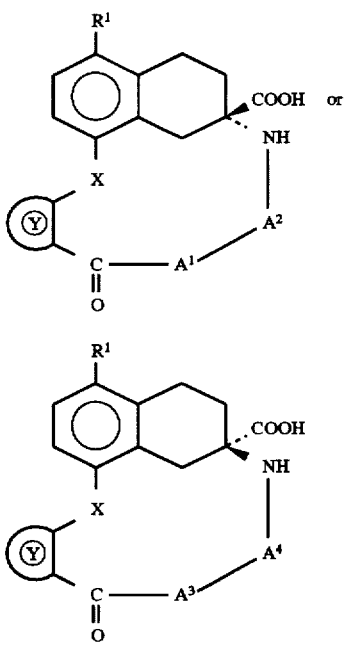

wherein

R¹ is hydrogen, bromine, cyano, formyl, hydroxy, lower alkyl, lower alkenyl, lower alkynyl, lower alkoxy, aryloxy, lower aralkoxy or aryl;

$A^1$, $A^2$, $A^3$ and $A^4$ each are residues of α-amino acids, wherein $A^1$ or $A^2$ are in the L configuration and $A^3$ or $A^4$ are in the D configuration when the α-C atom of said α-amino acid residue is asymmetric;

X is oxygen or sulphur; and

Y and the two C atoms together are an aromatic ring selected from the group consisting of benzene, furan, thiophene, pyridine or pyrimidine, wherein said aromatic ring is substituted or unsubstituted;

and the salts thereof.

15. The compound of claim 14 wherein X is sulfur.

16. The compound of claim 14 wherein X is oxygen.

17. The compound of claim 16, wherein the aromatic ring is benzene or pyridine which is unsubstituted or mono- or di-substituted by nitro, amino, lower alkanoylamino, hydroxy, lower alkoxy, lower alkanoyloxy, lower alkyl, fluorine, cyano, carboxy or formyl, or is condensed with a benzene ring to form a bicyclic system.

18. The compound of claim 17 wherein R¹ is hydrogen.

19. The compound of claim 17 wherein the aromatic ring is benzene, benzene substituted by alkanoylamino, or pyridine.

20. The compound of claim 19 wherein R¹ is hydrogen.

21. The compound of claim 9 wherein $A^1$ or $A^3$ is a residue of asparagine, aspartic acid, glutamine, glutamic acid, lysine or 2-amino-2-methylpropionic acid, and $A^2$ or $A^4$ is a residue of L- or D-alanine, asparagine, aspartic acid, glutamine, glutamic acid or lysine.

22. The compound of claim 21 wherein R¹ is hydrogen.

23. The compound of claim 21 wherein $A^1$ or $A^3$ is a residue of L- or D-alanine or lysine, and $A^2$ or $A^4$ is a residue of L- or D-alanine.

24. The compound of claim 3 wherein R¹ is hydrogen.

* * * * *

UNITED STATES PATENT AND TRADEMARK OFFICE
CERTIFICATE OF CORRECTION

PATENT NO.   : 5,644,024
DATED        : July 1, 1997
INVENTOR(S)  : Christine Abrecht, Klaus Müller, Daniel Obrecht and Arnold Trzeciak It is certified that error appears in the above-indentified patent and that said Letters Patent is hereby corrected as shown below:

Column 56, claim 21, line 1, replace "claim 9" with -- claim 19 --

Column 56, claim 24, line 1, replace "claim 3" with -- claim 23 --

Signed and Sealed this

Twenty-sixth Day of August, 1997

Attest:

BRUCE LEHMAN

*Attesting Officer*       *Commissioner of Patents and Trademarks*